(12) United States Patent
Hanson et al.

(10) Patent No.: US 7,989,482 B2
(45) Date of Patent: Aug. 2, 2011

(54) INDOLINE ANTI-CANCER AGENTS

(75) Inventors: Gunnar James Hanson, Chapel Hill, NC (US); Qi Wei, Dallas, TX (US); Charles Caldwell, Dallas, TX (US); Ming Zhou, Coppell, TX (US); Lai Wang, Dallas, TX (US); Susan Harran, Dallas, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 282 days.

(21) Appl. No.: 12/432,615

(22) Filed: Apr. 29, 2009

(65) Prior Publication Data

US 2010/0035946 A1 Feb. 11, 2010

Related U.S. Application Data

(60) Provisional application No. 61/048,869, filed on Apr. 29, 2008, provisional application No. 61/112,062, filed on Nov. 6, 2008.

(51) Int. Cl.
*A61K 31/42* (2006.01)
*C07D 291/00* (2006.01)

(52) U.S. Cl. ......... 514/375; 540/457; 540/458; 540/459

(58) Field of Classification Search ................... 540/457, 540/458, 459; 514/375
See application file for complete search history.

(56) References Cited

U.S. PATENT DOCUMENTS

| | | | |
|---|---|---|---|
| 4,261,989 A | 4/1981 | Sasaki et al. | |
| 5,387,584 A | 2/1995 | Schnur | |
| 5,624,677 A | 4/1997 | El-Rashidy et al. | |
| 5,932,566 A | 8/1999 | Schnur et al. | |
| 6,872,721 B2 | 3/2005 | Orme et al. | |
| 7,022,720 B2 | 4/2006 | Harran et al. | |
| 7,517,895 B2 | 4/2009 | Harran et al. | |
| 2006/0089397 A1 | 4/2006 | Harran et al. | |
| 2007/0149583 A1 | 6/2007 | Harran et al. | |
| 2009/0005572 A1 | 1/2009 | Hanson et al. | |

FOREIGN PATENT DOCUMENTS

| | | |
|---|---|---|
| WO | WO-02/36075 | 5/2002 |
| WO | WO-2005/028434 | 3/2005 |

OTHER PUBLICATIONS

Chattopadhyay et al., J. Chem. Soc., Perkin Trans. 1 (2000) 2415-2428.
Cheung et al., Bioorg. Med. Chem. Lett. (2005) 15:3338-3343.
Chiosis et al., ACS Chem. Biol. (2006) 1(5):279-284.
Hendrickson et al., J. Org. Chem. (1987) 52:4137-4139.
International Search Report for PCT/US09/42181, mailed on Jun. 10, 2009, 2 pages.
Konda-Yamada et al., Tetrahedron (2002) 58:7851.
Liang and Feng, Tetrahedron Letters (1996) 37:6627-6630.
Moulin et al., J. Amer. Chem. Soc. (2005) 127:6999-7004.
Schollkopf et al., Liebigs Ann. Chem. (1983) 1133-1151.
Soga et al., Curr. Cancer Drug Targets (2003) 3:359-369.
Written Opinion of the International Searching Authority for PCT/US09/42181, mailed on Jun. 10, 2009, 5 pages.
Yamamoto et al., Angew. Chem. (2003) 42:1280-1284.
Yokoyama et al., Eur. J. Org. Chem. (2004) 1244.
Yokoyama et al., Tetrahedron Letters (1999) 40:7803.

*Primary Examiner* — Bruck Kifle
(74) *Attorney, Agent, or Firm* — Richard Aron Osman

(57) ABSTRACT

Indoline compounds having anti-mitotic activity, useful for the treatment of cancer and other proliferative disorders are provided.

18 Claims, 2 Drawing Sheets

INDOLINE ANTI-CANCER AGENTS

RELATED APPLICATIONS

This application claims benefit of priority to U.S. Provisional Application Ser. No. 61/048,869, filed 29 Apr. 2008; and U.S. Provisional Application Ser. No. 61/112,062, filed 6 Nov. 2008. The contents of these documents are incorporated herein by reference in their entirety.

TECHNICAL FIELD

The invention relates to indoline compounds of formula (I), and to salts, pharmaceutical compositions, and conjugates thereof, which are useful as anti-proliferative agents.

BACKGROUND ART

Diazonamide A is a mitotic spindle-disrupting agent first isolated from the marine organism *Diazona angulata*, having the structure:

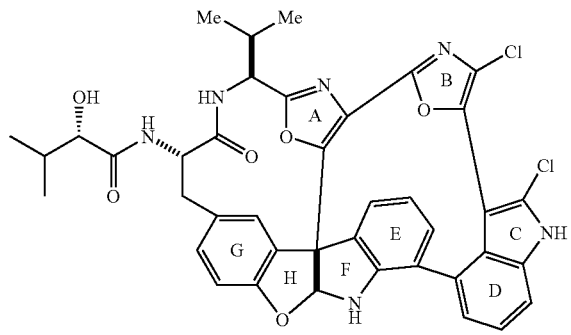

The preparation of diazonamide analogs via macrocyclic indoline intermediates bearing a carbobenzyloxy (Cbz) or o-nitrophenylsulfonyl protected amino group has been previously described. U.S. Pat. No. 7,022,720 correctly discloses the structure of diazonamide A and describes the synthesis of some of its analogs. U.S. application Ser. No. 11/264,502, a continuation-in-part of U.S. application Ser. No. 10/227,509 (now U.S. Pat. No. 7,022,720) was filed 31 Oct. 2005, and is published as US 2006/0089397. U.S. Ser. No. 11/591,016, a continuation-in-part of U.S. application Ser. No. 11/264,502, was filed 31 Oct. 2006, and is published as US 2007/0149583. U.S. application Ser. No. 12/134,984, filed 6 Jun. 2008, and published as US 2009/0005572, describes synthetic methods for the preparation of diazonamide analogs via indoline intermediates.

It has surprisingly been found that indoline compounds of formula (I), which lack the rigid macrocyclic structure bridging the A- and E-rings of the diazonamide skeleton, possess potent cytotoxic activity and are useful for the treatment of cell proliferative disorders.

DISCLOSURE OF THE INVENTION

The present invention is directed towards compounds of formula (I)

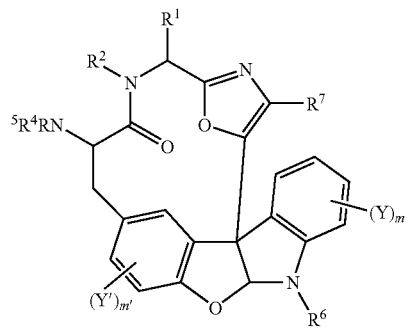

and the pharmaceutically acceptable salts and conjugates thereof. The invention is also directed towards pharmaceutical compositions comprising a compound of formula (I) and/or a salt or conjugate thereof, to modified forms of such compounds conjugated to stabilizing or targeting agents, and to methods of treating or ameliorating cell proliferative diseases using these compounds and formulations.

In one aspect, the invention provides a compound of formula (I):

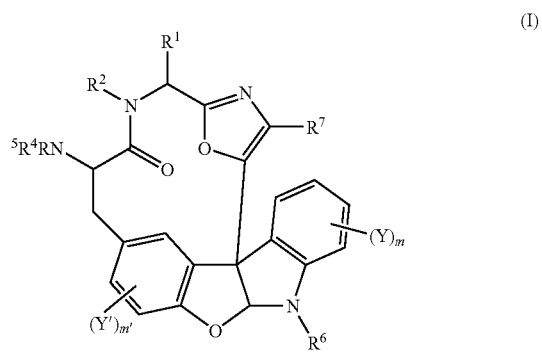

or a pharmaceutically acceptable salt or conjugate thereof;
wherein $R^1$ is H, or C1-C8 alkyl, C2-C8 alkenyl, C2-C8 alkynyl, C1-C8 heteroalkyl, C2-C8 heteroalkenyl, C2-C8 heteroalkynyl, C6-C12 aryl, C7-C14 arylalkyl, C5-C12 heteroaryl, or C6-C14 heteroarylalkyl, each of which may be optionally substituted;

$R^2$ is H, or C1-C8 alkyl, C1-C8 heteroalkyl, C7-C14 arylalkyl, C6-C14 heteroarylalkyl, each of which may be optionally substituted; or $R^1$ and $R^2$ may be taken together with the atoms to which they are attached to form an optionally substituted 5- to 7-membered azacyclic ring, optionally containing an additional heteroatom selected from N, O, and S as a ring member;

$R^4$ is H, or C1-C4 alkyl;

$R^5$ is H, or C1-C8 alkyl, C2-C12 alkenyl, C3-C8 cycloalkyl, C4-C12 cycloalkylalkyl, C2-C12 alkynyl, C6-C12 aryl, C7-C14 arylalkyl, C5-C12 heteroaryl, C6-C14 heteroarylalkyl, alkylsulfonyl, or arylsulfonyl, or a heteroform of one of these, each of which may be optionally substituted; or $R^5$ is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or $R^4$ and $R^5$ may be taken together with nitrogen to form an optionally substituted 3- to 8-membered azacyclic ring, optionally containing an additional heteroatom selected from N, O, and S as a ring member;

$R^6$ is H, or C1-C8 alkyl, C1-C8 heteroalkyl, C7-C14 arylalkyl, C6-C14 heteroarylalkyl, C1-C6 acyl, C6-C12 aroyl, alkylsulfonyl, or arylsulfonyl, each of which may be optionally substituted;

$R^7$ is H, halo, optionally substituted C6-C12 aryl, optionally substituted C5-C12 heteroaryl, optionally substituted C5-C12 heterocyclyl, —CN, —COR$^8$, —COOR$^8$, or —C(O)NR$^9_2$;

$R^8$ is H, or C1-C8 alkyl, C2-C8 alkenyl, C6-C12 aryl, or C7-C14 arylalkyl, or a heteroform of one of these, each of which may be optionally substituted; and each $R^9$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^9$ on the same N can cyclize to form an optionally substituted 3- to 8-membered azacyclic ring, optionally containing an additional heteroatom selected from N, O, and S as a ring member;

m is 0-4;

m' is 0-3; and each Y and Y' is independently halo, OH, C1-C4 alkoxy, or C1-C8 alkyl, C2-C8 alkenyl, C2-C8 alkynyl, C6-C12 aryl, or C7-C14 arylalkyl, or a heteroform of one of these, each of which may be optionally substituted.

In another aspect, the invention provides a compound of formula (II):

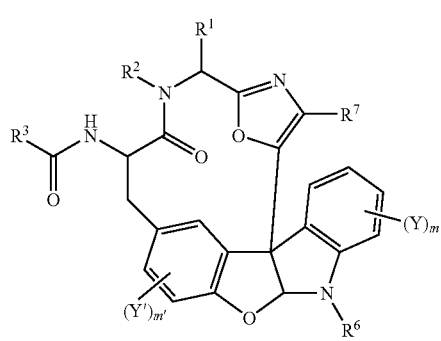

(II)

or a pharmaceutically acceptable salt or conjugate thereof, wherein $R^1$, $R^2$, $R^3$, $R^6$, $R^7$, Y, Y', m and m' are as defined for formula (I).

In further aspect, the invention provides a compound of formula (III):

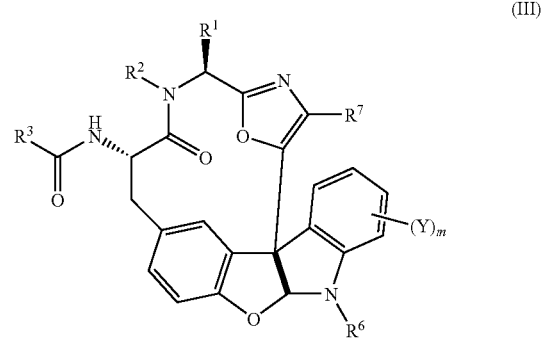

(III)

or a pharmaceutically acceptable salt or conjugate thereof, wherein $R^1$, $R^2$, $R^3$, $R^6$, $R^7$, Y, and m are as defined for formula (I).

In another aspect, the invention provides a compound of formula (IV):

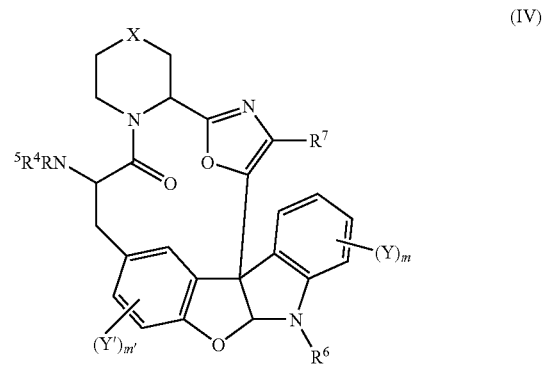

(IV)

or a pharmaceutically acceptable salt or conjugate thereof; wherein X is O, S, NR" or $(CH_2)_n$, where n is 0-2, and R" is H, C1-C8 alkyl, C5-C8 aryl, C6-C12 arylalkyl, C1-C6 acyl, C6-C12 aroyl, alkylsulfonyl, or arylsulfonyl; and $R^4$, $R^5$, $R^6$, $R^7$, Y, Y', m and m' are defined as for formula (I).

In another aspect, the invention provides a compound of formula (V) or formula (VI):

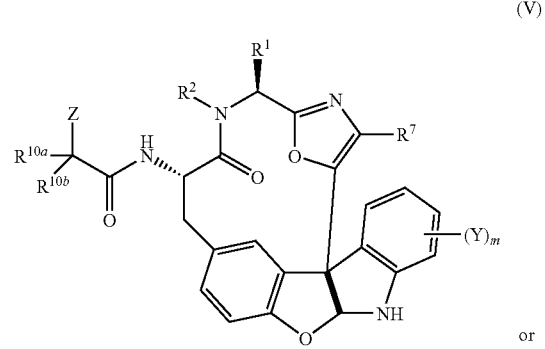

(V)

or

-continued

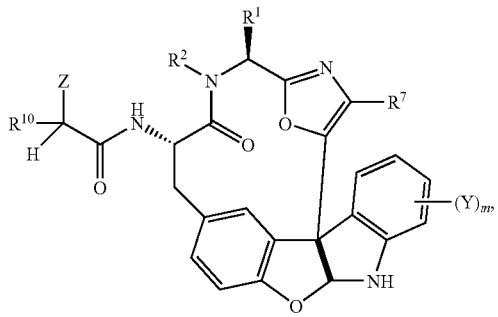

(VI)

or a pharmaceutically acceptable salt or conjugate thereof;
wherein $R^1$, $R^2$, $R^7$, Y, and m are defined as for formula (I);
Z is OH, OR, $CH_2OR$, SR, and $NR_2$, where each R is independently H, optionally fluorinated C1-C4 alkyl, or optionally fluorinated C1-C4 acyl; and
each of $R^{10}$, $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C14 arylalkyl, or a heteroform of one of these, each of which may be optionally substituted; or
$R^{10a}$ and $R^{10b}$ may be taken together with the carbon to which they are attached to form a C3-C8 cycloalkyl or a C3-C8 heterocyclyl ring, which may be optionally substituted.

In a further aspect, the invention provides a pharmaceutical composition comprising at least one compound of any of formulae (I), (II), (III), (IV), (V) or (VI) and a pharmaceutically acceptable excipient.

In another aspect, the invention provides a method for treating or ameliorating a cell proliferative disorder, comprising administering to a subject in need thereof a therapeutically effective amount of at least one compound of formulae (I), (II), (III), (IV), (V) or (VI) or a salt, conjugate, or pharmaceutical composition thereof. In some embodiments, the amount administered is sufficient to inhibit cell proliferation. In other embodiments, the amount is sufficient to slow tumor growth or reduce tumor size. In some embodiments, the compound of formulae (I)-(VI) is used in combination with another chemotherapeutic agent or approach.

Provided also are methods for inhibiting cell proliferation in a cell, comprising contacting the cell with a compound of one of the formulae described herein, or a salt, or conjugate thereof, in an amount effective to inhibit cell proliferation. In some embodiments, the cells are in a cell line, such as a cancer cell line (e.g., a cell line derived from breast, prostate, pancreatic, lung, or hematopoietic cancers, etc.). In some embodiments, the cells are in a tissue, an in some such embodiments, the tissue can be in a subject. In other embodiments, the cells are in a tumor, and sometimes are in a tumor in a subject.

Provided also are methods for treating cancer in a subject in need of such treatment, comprising: administering to the subject a therapeutically effective amount of a compound of formula (I)-(VI) or a salt or conjugate thereof, as described herein, in an amount that is effective to treat or ameliorate said cancer.

In some embodiments, the compound of formula (I)-(VI) is a compound in one of the Tables provided herein, or a pharmaceutically acceptable salt or conjugate of one of these compounds.

The invention further provides methods for treating or ameliorating a condition related to aberrant cell proliferation. For example, provided are methods of treating or ameliorating a cell proliferative disorder in a subject, comprising administering a compound of formula (I)-(VI) or a salt or conjugate thereof, as described herein, to a subject in need thereof in an amount effective to treat or ameliorate the condition.

In the methods described herein, the subject may be a research animal (e.g., rodent, dog, cat, monkey), optionally containing a tumor such as a xenograft tumor (e.g., human tumor), for example, or may be a human.

MODES OF CARRYING OUT THE INVENTION

Figure 1:
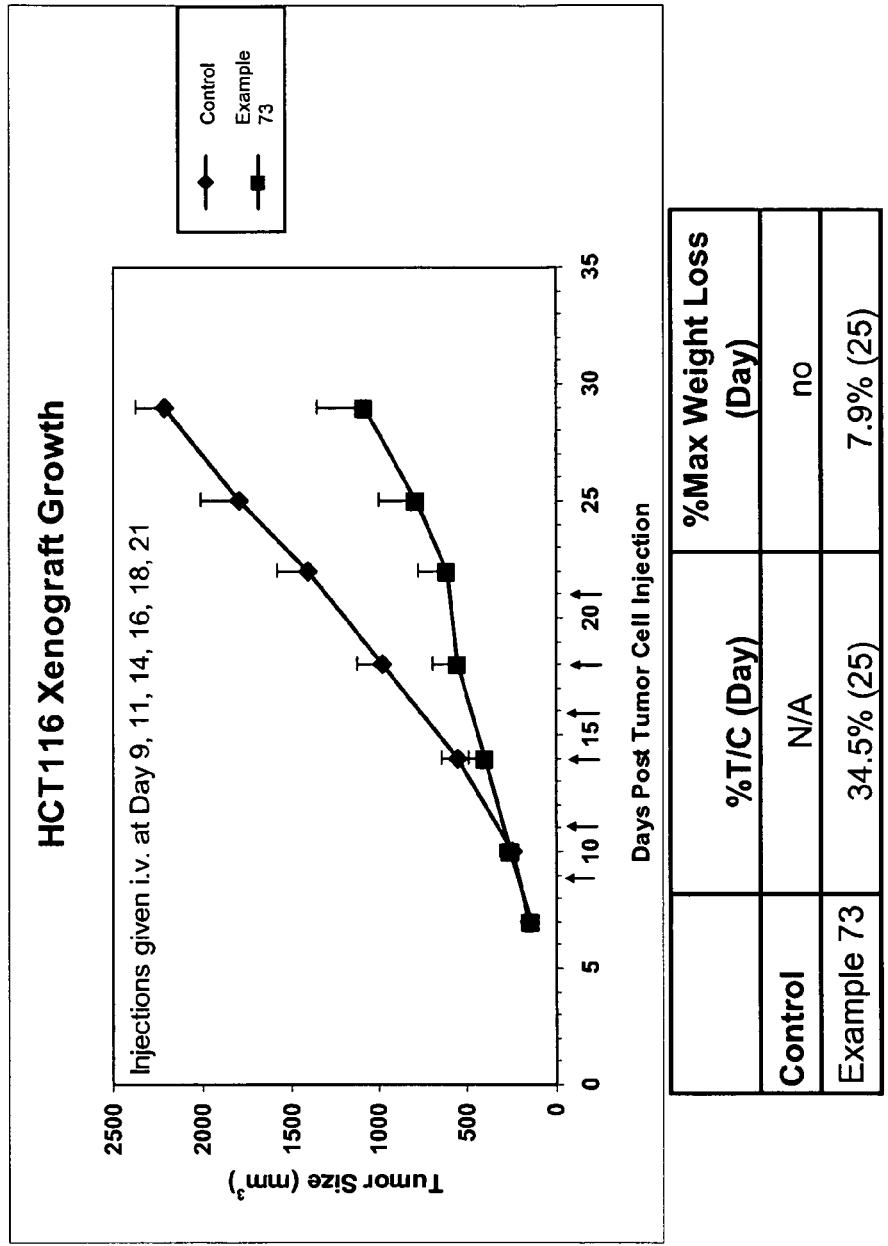
FIG. 1 shows data for compound of Example 73 in an HCT116 human colon carcinoma xenograft model in mice. Compound of Example 73 was administered at 20 mg/kg per dose. Injections were given at days 9, 11, 14, 16, 18 and 21 post tumor cell injection. At day 25, the tumor size for treated animals was 34.5% of control, and a maximum weight loss of 7.9% was observed.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular forms "a", "an", and "the" include plural references unless indicated otherwise.

As used herein, the term "subject" refers to a human or animal subject. In preferred embodiments, the subject is human.

The terms "treat", "treating" or "treatment" in reference to a particular disease or disorder include prevention of the disease or disorder, and/or lessening, improving, ameliorating, alleviating or removing the symptoms and/or pathology of the disease or disorder.

The term "therapeutically effective amount" or "effective amount" is intended to mean that amount of a drug or pharmaceutical agent that will elicit a biological or medical response of a cell, tissue, system, animal or human that is being sought by a researcher, veterinarian, medical doctor or other clinician. The terms also can refer to reducing or stopping a cell proliferation rate (e.g., slowing or halting tumor growth) or reducing the number of proliferating cancer cells (e.g., removing part or all of a tumor). Sometimes, the rate or cell proliferation is reduced by 10%, 20%, 30%, 40%, 50%, 60%, or 70% or more. Sometimes, the number of proliferating cells is reduced by 10%, 20%, 30%, 40%, 50%, 60%, or 70% or more.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isopropyl, isobutyl, tert-butyl, cyclohexyl, cyclopentylethyl, 2-propenyl, 3-butynyl, and the like. The total number of carbon atoms in each such group is sometimes described herein, e.g., when the group can contain up to twelve carbon atoms it may be described as 1-12C or as C1-C12 or as C1-12 or as $C_{1-12}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-12C (alkyl) or 2-12C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present. Exemplary heteroalkyls include alkoxyls such as O-alkyl, alkyl ethers, secondary and tertiary alkyl amines, alkyl sulfides, and the like.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than three contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a saturated or partially saturated, monocyclic or fused or spiro polycyclic, carbocycle that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. Frequently, cycloalkyl and heterocyclyl groups are C3-C8, and cycloalkylalkyl or heterocyclylalkyl groups are C4-C12. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or cycloalkylalkyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom (which may be depicted herein as —C(=O)R, —C(O)R, or COR) where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl. Also included within the definition of heteroacyl groups are thioacyl substituents, e.g., —C(=S)R, and imine groups, e.g., —C(=NH)R.

Acyl and heteroacyl groups are bonded to any group or molecule to which they are attached through the open valence of the carbonyl carbon atom. Typically, they are C1-C8 acyl groups, which include formyl, acetyl, trifluoroacetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Carbocyclic aryl rings and ring systems typically 6-12 carbon ring atoms, and may include a saturated or partially unsaturated carbocyclic ring fused to an aromatic ring, e.g., a tetrahydronaphthalene, indane or indene ring system. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. Preferably the monocyclic aryl and heteroaryl groups contain 5-6 ring members, and the bicyclic aryl and heteroaryl groups contain 8-10 ring members.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a heteroform thereof, preferably a C1-C4 alkyl. These linkers may also include a carbonyl group, thus making them able to provide substituents as an acyl or heteroacyl moieties.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl. Preferably, an arylalkyl group includes one or two optionally substituted phenyl rings and a C1-C4 alkylene that is unsubstituted or is substituted with one or two C1-C4 alkyl groups or C1-C4 heteroalkyl groups, where the alkyl or heteroalkyl groups can optionally cyclize to form a ring such as cyclopropane, dioxolane, or oxacyclopentane, and wherein the alkyl or heteroalkyl groups may be optionally fluorinated. Examples of arylalkyl groups include optionally substituted benzyl, phenylethyl, diphenylmethyl, and triphenylmethyl groups. Optional substituents when present on the aryl ring of an arylalkyl group are the same as those described herein for an aryl ring. Arylalkyl groups typically contain from 7-20 atoms, preferably 7-14 atoms.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. For example, heteroaryl groups include pyridylmethyl, pyridylethyl, —O-benzyl, and the like. Heteroarylalkyl groups typically contain from 6-20 atoms, preferably 6-14 atoms.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)— and —C(Me)$_2$— may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$— would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, cycloalkyl, alkynyl, acyl, aryl, and arylalkyl are heteroalkyl, heteroalkenyl, heterocyclyl, heteroalkynyl, heteroacyl, heteroaryl, and heteroarylalkyl, respectively. It will be understood that the heteroform of an aryl or arylalkyl moiety may contain one less "C" atom than the corresponding all carbon system, because the inclusion of a heteroatom permits aromaticity in 5-membered rings. For example, the heteroform of C6-C12 aryl is C5-C12 heteroaryl, and the heteroform of C7-C20 arylalkyl is C6-C20 heteroarylalkyl. It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

Unless otherwise indicated, the term "oxo" refers to =O.

"Halo", as used herein, includes fluoro, chloro, bromo and iodo. Fluoro, chloro, and bromo are often preferred.

"Amino" as used herein refers to NH$_2$, but where an amino is described as "substituted" or "optionally substituted", the term includes NR$_2$ wherein each R is independently H, or is an alkyl, alkenyl, alkynyl, acyl, aryl, or arylalkyl group or a heteroform of one of these groups, as further defined herein, each of which may be optionally substituted with the substituents described herein as suitable for the corresponding type of group. The term also includes forms wherein the two R groups on one nitrogen atom (i.e., NR$_2$) are linked together to form a 3-8 membered monocyclic azacyclic ring or an 8-12 membered bicyclic fused azacyclic ring system, each of which may be saturated, unsaturated or aromatic and which may contain 1-3 heteroatoms including the azacylic ring nitrogen atom independently selected from N, O and S as ring members (i.e., 0-2 heteroatoms selected from N, O and S in addition to the nitrogen atom of the azacyclic ring), and which may be optionally substituted with the substituents described as suitable for alkyl groups or, if NR$_2$ comprises an aromatic group, it may be optionally substituted with the substituents described as typical for aryl or heteroaryl groups.

Amino groups may optionally be in a protected or unprotected form. One of skill in the art would appreciate that appropriate amine protecting groups may vary depending on the functionality present in the particular molecule and the nature of the amino group. Suitably protected amines may include, for example, amines protected as carbamates (e.g., tert-butoxycarbonyl (Boc), benzyloxycarbonyl (Cbz), fluorenylmethyloxy-carbonyl (Fmoc), allyloxycarbonyl (Alloc) or (trialkylsilyl)ethoxycarbonyl), carboxamides (e.g., formyl, acyl or trifluoroacetyl, benzoyl), sulfonamides, phthalimides, succinimides, Schiff's base derivatives, and the like. Also included are alkyl or allyl amines, as well as trialkylsilyl protected amines.

Where an amine is present in protected form, it is sometimes desirable to remove the protecting group. Thus, the methods of the present invention also optionally include a step of removing any protecting groups on an amine or aminoalkyl group.

The terms "alkylsulfonyl" and "arylsulfonyl" as used herein refer to moieties of the form —SO$_2$alkyl or —SO$_2$aryl, where alkyl and aryl are defined as above. Optionally fluorinated $C_{1-4}$ alkyl, and optionally substituted phenyl groups are preferred for sulfonyl moieties. The phenyl groups of an arylsulfonyl moiety may be optionally substituted with one or more substituents suitable for an aryl ring; for example, they may be substituted by halo, methyl, nitro, alkoxy, amino, or the like. Such sulfonyl moieties, when present on oxygen form sulfonates. Such sulfonyl moieties form sulfonamides when present on nitrogen, and sulfones when present on carbon. Representative sulfonates include, e.g., —$OSO_2Me$ (mesylate), —$OSO_2CF_3$ (triflate), —$OSO_2tolyl$ (tosylate), and the like.

The term "alkoxycarbonyl" as used herein refers to a moiety of the form —COOR', where R' is C1-C8 alkyl, C2-C8 alkenyl, C5-C6 aryl, or C7-C14 arylalkyl, trialkylsilyl, or the like, each of which may be optionally substituted. When present on nitrogen, such alkoxycarbonyl moieties form carbamates, which are frequently used as nitrogen protecting groups. In some such embodiments, R' may be optionally halogenated C1-C4 alkyl (e.g., tert-butyl, methyl, ethyl, 2,2,2-trichloroethyl, 1,1-dimethyl-2,2,2-trichloroethyl), allyl, optionally substituted benzyl, fluorenylmethyl, or trialkylsilyl (e.g., triisopropylsilyl, triethylsilyl, tert-butyldimethylsilyl). When present on carbon, such moieties may also be referred to as carboxylate esters, carboalkoxy groups, or the like. In some embodiments containing a carboxylate ester functional group, R' is preferably a $C_{1-4}$ alkyl group. In some such embodiments, R' is methyl, ethyl, n-propyl, isopropyl, n-butyl, isobutyl, s-butyl or t-butyl.

The term "substituted" means that the specified group or moiety bears one or more non-hydrogen substituents. The term "unsubstituted" means that the specified group bears no such substituents.

"Optionally substituted" as used herein indicates that the particular group or groups being described may have no non-hydrogen substituents, or the group or groups may have one or more non-hydrogen substituents (i.e., the group may be substituted or unsubstituted). If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Alkyl, alkenyl and alkynyl groups are often substituted to the extent that such substitution makes sense chemically. Typical substituents include, but are not limited to, halo, OH, =O, =N—CN, =N—OR, =NR, OR, $NR_2$, SR, SOR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR', =NR', OR', $NR'_2$, SR', SOR', $SO_2R'$, $SO_2NR'_2$, $NR'SO_2R'$, $NR'CONR'_2$, $NR'COOR'$, $NR'COR'$, CN, COOR', $CONR'_2$, OOCR', COR', and $NO_2$, wherein each R' is independently H, optionally fluorinated C1-C8 alkyl, C2-C8 heteroalkyl, C1-C8 acyl, C2-C8 heteroacyl, C6-C12 aryl or C5-C12 C12 heteroaryl, C5-C20 arylalkyl, or C5-C20 heteroarylalkyl. Alkyl, alkenyl and alkynyl groups can also be substituted by C1-C8 acyl, C2-C8 heteroacyl, C6-C12 aryl or C5-C12 heteroaryl, each of which can be substituted by the substituents that are appropriate for the particular group.

Preferred substituents when present on an alkyl, alkenyl or alkynyl group, or a heteroform of one of these, include halo, OH, =O, OR, SR, and $NR_2$, where R is defined as above; sometimes, R is H, optionally fluorinated C1-C4 alkyl, or optionally fluorinated C1-C4 acyl. Particularly preferred substituents when present on $R^3$ include OH, =O, C1-C4 alkoxy, OAc, NHAc, $NH_2$, and NHMe. Sometimes, optional substituents present on an alkyl, alkenyl or alkynyl group, or a heteroform of one of these, include $NRSO_2R$, $NRCONR_2$, COOR, or $CONR_2$, where R is defined as above; preferably, each R is independently H, optionally fluorinated C1-C4 alkyl, or is C6-C12 aryl, C5-C12 heteroaryl, C7-C20 arylalkyl, or C6-C20 heteroarylalkyl, each of which may be optionally substituted.

Aryl, heteroaryl and heterocyclyl moieties may be substituted with a variety of substituents including optionally fluorinated C1-C8 alkyl, C2-C8 alkenyl, C2-C8 alkynyl, C1-C8 acyl, and heteroforms of these, C6-C12 aryl, C5-C12 for heteroaryl, C6-20 arylalkyl (C5-20 for heteroarylalkyl), each of which can itself be further substituted; other substituents for aryl and heteroaryl moieties include halo, OH, OR, $CH_2OH$, $CH_2OR$, $CH_2NR_2$, $NR_2$, SR, SOR, $SO_2R$, $SO_2NR_2$, $NRSO_2R$, $NRCONR_2$, NRCOOR, NRCOR, CN, COOR, $CONR_2$, OOCR, C(O)R, and $NO_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as described above for alkyl groups. The substituent groups on an aryl or heteroaryl group may of course be further substituted with the groups described herein as suitable for each type of group that comprises the substituent. Preferred substituents when present on an aryl, heteroaryl and heterocyclyl moieties include halo, OH, OR, $CH_2OH$, $CH_2OR$, $CH_2NR_2$, SR, $NR_2$, CN, COOR, $CONR_2$, and $NO_2$, where R is defined as above, or optionally substituted C6-C12 aryl or C5-C12 heteroaryl ring.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

In certain embodiments, the carbon atom bearing the substituent $R^1$ in formulae (I), (II), (III), (V), (VI), or the corresponding atom in formula (IV), has the (S)-configuration. In certain embodiments of formulae (I)-(VI), the carbon atom bearing the substituent $NR^4R^5$ $NHC(=O)R^3$, $NHC(=O)CH(Z)R^{10}$ or $NHC(=O)C(Z)R^{10a}R^{10b}$ has the (S)-configuration.

The present invention provides novel indoline analogs of formula (I), which are useful for the treatment or amelioration of proliferative disorders, in particular cancer.

In compounds of formula (I), $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted. In certain preferred embodiments, $R^1$ is an optionally substituted C1-C4 alkyl; in some such embodiments, $R^1$ is isopropyl.

In compounds of formula (I), $R^2$ is H, or C1-C8 alkyl, C1-C8 heteroalkyl, C7-C14 arylalkyl, C6-C14 heteroarylalkyl, each of which may be optionally substituted. In specific embodiments, $R^2$ is H or methyl. In certain preferred embodiments, $R^2$ is H.

In other embodiments, $R^1$ and $R^2$ are taken together with the atoms to which they are attached to form an optionally substituted 5- to 7-membered azacyclic ring, optionally containing an additional heteroatom selected from N, O, and S as a ring member. In specific embodiments, $R^1$ and $R^2$ are taken together to form an optionally substituted 5- to 7-membered azacyclic ring containing no additional heteroatoms, i.e., an optionally substituted pyrrolidine, piperidine or homopiperidine ring. In other embodiments, $R^1$ and $R^2$ are taken together to form an optionally substituted 5- to 7-membered azacyclic ring containing an additional heteroatom selected from N, O and S. In some such embodiments, $R^1$ and $R^2$ are taken together to form an optionally substituted morpholine, thiomorpholine, piperazine, or homopiperazine ring.

In compounds of formula (I), $R^4$ is H, or C1-C4 alkyl. In preferred embodiments, $R^4$ is H.

In certain embodiments of formula (I), $R^5$ is H, or C1-C8 alkyl, C2-C12 alkenyl, C3-C8 cycloalkyl, C4-C12 cycloalkylalkyl, C2-C12 alkynyl, C6-C12 aryl, C7-C14 arylalkyl, alkylsulfonyl, or arylsulfonyl, or a heteroform of one of these, each of which may be optionally substituted.

In compounds of the present invention, when $R^5$ is an arylsulfonyl group, it is preferably not an o-nitrophenylsulfonyl group. In particular, the present invention specifically excludes the compound of formula

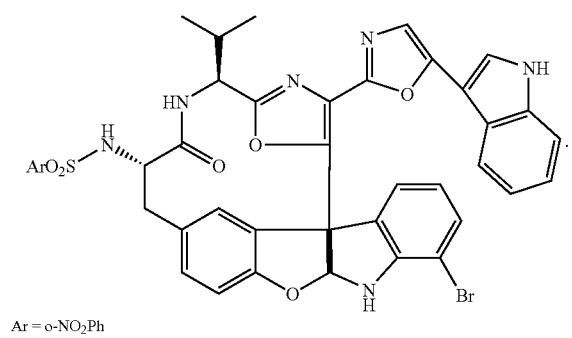

Ar = o-NO$_2$Ph

In other embodiments of formula (I), $R^5$ is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted.

In certain embodiments, $R^5$ is C(=O)$R^3$, where $R^3$ is C1-C4 alkyl, C3-C6 cycloalkyl, C4-C8 cycloalkylalkyl, or C6-C8 arylalkyl, each of which may be optionally substituted. In preferred embodiments, the alkyl group comprising part of $R^3$ is substituted with at least one substituent selected from the group consisting of OH, OMe, OAc, NH$_2$, NHMe, and NHAc.

In other embodiments, $R^5$ is C(=O)$R^3$, where $R^3$ is C1-C8 alkyl, C2-C10 alkenyl, C3-C8 cycloalkyl, C4-C9 cycloalkylalkyl, or C7-C14 arylalkyl, each of which may be optionally substituted. In preferred embodiments, the alkyl group comprising part of $R^3$ is substituted with at least one substituent selected from the group consisting of OH, OMe, OAc, NH$_2$, NHMe, CH$_2$OH and NHAc.

In specific embodiments of formula (I), when $R^5$ is —C(O)$R^3$, $R^3$ is a C1-C8 straight chain, branched, or cycloalkyl group, each of which is substituted on the carbon atom adjacent to the carbonyl group that is part of $R^5$ with OH, OMe, OAc, NH$_2$, NHMe, CH$_2$OH or NHAc.

In other embodiments of formula (I), $R^4$ and $R^5$ may be taken together with nitrogen to form an optionally substituted 3- to 8-membered azacyclic ring, optionally containing an additional heteroatom selected from N, O, and S as a ring member.

In compounds of formula (I), $R^6$ is H, or C1-C8 alkyl, C1-C8 heteroalkyl, C7-C14 arylalkyl, C6-C14 heteroarylalkyl, optionally fluorinated C1-C6 acyl, C6-C12 aroyl, alkylsulfonyl, or arylsulfonyl, each of which may be optionally substituted. In preferred embodiments of formula (I), $R^6$ is H. In some embodiments, a substituent at $R^6$ may function as a protecting group. It will be understood that the methods described herein include an optional deprotection step to remove any protecting groups present on the molecule.

In compounds of formula (I), $R^7$ is H, halo, optionally substituted C6-C12 aryl, optionally substituted C5-C12 heteroaryl, optionally substituted C5-C12 heterocyclyl, —CN, —COR$^8$, —COOR$^8$, or —C(O)NR$^9{}_2$, where $R^8$ is H, or C1-C8 alkyl, C2-C8 alkenyl, C6-C12 aryl, or C7-C14 arylalkyl, or a heteroform of one of these, each of which may be optionally substituted, and each $R^9$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^9$ on the same N can cyclize to form an optionally substituted 3- to 8-membered azacyclic ring, optionally containing an additional heteroatom selected from N, O, and S as a ring member.

In certain embodiments, $R^7$ is CONR$^9{}_2$, where each $R^9$ is defined as above. In frequent embodiments, at least one $R^9$ is H, and the other $R^9$ is H or an optionally substituted C7-C14 arylalkyl or C6-C14 heteroarylalkyl group; preferably, the alkyl portion of such a group is a C1-C4 alkyl. In specific embodiments, at least one $R^9$ is an optionally substituted benzyl, diphenylmethyl, phenethyl, tetrahydronaphthyl, or a heteroarylalkyl group, such as an indolylalkyl or pyridinylalkyl. In some embodiments, two $R^9$ groups on the same nitrogen atom can cyclize to form an optionally substituted 3- to 8-membered azacyclic ring, optionally containing an additional heteroatom selected from N, O, and S as a ring member. In specific embodiments, two $R^9$ groups on the same nitrogen atom are cyclized to form an optionally substituted pyrrolidine ring.

In other embodiments, $R^7$ is optionally substituted C6-C12 aryl, optionally substituted C5-C12 heteroaryl ring, or optionally substituted C5-C12 heterocyclyl ring. In some such embodiments, $R^7$ is an optionally substituted phenyl, naphthyl, benzimidazole, benzoxazole, benzthiazole, pyridinyl, pyrimidinyl, pyrazinyl or pyridazinyl ring. In other such embodiments, $R^7$ is an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole or tetrazole ring.

Preferred substituents when present on an optionally substituted C6-C12 aryl, C5-C12 heteroaryl, or C5-C12 heterocyclyl ring at $R^7$ include halo, nitro, cyano, or optionally fluorinated C1-C4 alkyl, optionally fluorinated C1-C4 alkoxy, COOR$^8$', CONR$^{9'}{}_2$, C6-C12 aryl or C5-C12 heteroaryl, each of which may be optionally substituted; where $R^{8'}$ is H, or C1-C8 alkyl, C2-C8 alkenyl, C6-C12 aryl, or C7-C14 arylalkyl, or a heteroform of one of these, each of which may be optionally substituted; and each $R^{9'}$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^{9'}$ on the same N can cyclize to form an optionally substituted 3- to 8-membered azacyclic ring, optionally containing an additional heteroatom selected from N, O, and S as a ring member.

In certain preferred embodiments, $R^7$ is an optionally substituted oxazole or thiazole ring. In some such embodiments, $R^7$ is an oxazole ring substituted with an optionally substituted C6-C12 aryl or C5-C12 heteroaryl ring. In some embodiments, $R^7$ is an oxazole ring substituted with one or more alkyl, halo, carboxylic acid, ester or amide substituents.

In compounds of formula (I), m is an integer from 0-4, and m' is an integer from 0-3. In certain embodiments, m is 0, 1, or 2, and m' is 0 or 1. In frequent embodiments, m' is 0.

In compounds of formula (I), each Y and Y' is independently C1-C8 alkyl, C2-C8 alkenyl, C2-C8 alkynyl, C6-C12 aryl, or C7-C14 arylalkyl, or a heteroform of one of these, each of which may be optionally substituted, or is halo, OH, or C1-C4 alkoxy.

In compounds of formula (II), $R^1$, $R^2$, $R^3$, $R^6$, $R^7$, Y, Y', m and m' are as defined for formula (I). In preferred embodiments of formula (II), $R^6$ is H, m' is 0, and m is 0 or 1. In frequent embodiments, $R^1$ is C1-C4 alkyl. In some embodiments, $R^2$ is H or methyl; preferably, $R^2$ is H.

The same groups described herein as useful for embodiments of formula (I), are also suitable for compounds of formulae (II), (III), (IV), (V) or (VI).

In certain embodiments of formula (II), $R^3$ is C1-C4 alkyl, C3-C6 cycloalkyl, C4-C8 cycloalkylalkyl, or C6-C8 arylalkyl, each of which may be optionally substituted. In other embodiments, $R^3$ is C1-C8 alkyl, C2-C10 alkenyl, C3-C8 cycloalkyl, C4-C9 cycloalkylalkyl, or C7-C14 arylalkyl, each of which may be optionally substituted. In preferred embodiments, the alkyl group comprising part of $R^3$ is substituted with at least one substituent selected from the group consisting of OH, OR, CH$_2$OR, SR, and NR$_2$, where each R is independently H, optionally fluorinated C1-C4 alkyl, or optionally fluorinated C1-C4 acyl. Sometimes, $R^3$ is substituted with at least one substituent selected from the group consisting of OH, OMe, OAc, NH$_2$, NHMe, CH$_2$OH and NHAc.

In certain embodiments of formula (II), $R^3$ is a group of the form —CH(Z)R$^{10}$, where Z is OH, OR, CH$_2$OR, SR, and NR$_2$, where each R is independently H, optionally fluorinated C1-C4 alkyl, or optionally fluorinated C1-C4 acyl, and R$^{10}$ is C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted. In some such embodiments, Z is OH, OMe, OAc, CH$_2$OH, SH, SMe, SAc, NH$_2$, NHMe, NMe$_2$, NHAc. Sometimes, Z is OH, OMe, OAc, NH$_2$, NHMe, or NHAc. In certain preferred embodiments, Z is OH.

In other embodiments of formula (II), $R^3$ is a group of the form —C(Z)R$^{10a}$R$^{10b}$, where Z is OH, OR, CH$_2$OR, SR, and NR$_2$, where each R is independently H, optionally fluorinated C1-C4 alkyl, or optionally fluorinated C1-C4 acyl, and each of R$^{10a}$ and R$^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or R$^{10a}$ and R$^{10b}$ may be taken together with the carbon to which they are attached to form a C3-C8 cycloalkyl or a C3-C8 heterocyclyl ring, which may be optionally substituted. In some such embodiments, Z is OH, OMe, OAc, CH$_2$OH, SH, SMe, SAc, NH$_2$, NHMe, NMe$_2$, NHAc. Sometimes, Z is OH, OMe, OAc, NH$_2$, NHMe, or NHAc. In certain preferred embodiments, Z is OH.

In compounds of formula (III), $R^1$, $R^2$, $R^3$, $R^6$, $R^7$, Y, and m are as defined for formula (I). In preferred embodiments of formula (III), $R^6$ is H, m' is 0, and m is 0 or 1. In frequent embodiments, $R^1$ is C1-C4 alkyl. In some embodiments, R is H or methyl; preferably, $R^2$ is H.

Embodiments described for formulae (I) or (II) are also suitable for compounds of formula (III), (IV), (V) or (VI).

In some embodiments of formula (III), $R^1$ is a C1-C8 alkyl, sometimes a C1-C4 alkyl, each of which may be optionally substituted. In certain preferred embodiments, $R^1$ is isopropyl. In some embodiments of formula (III), $R^2$ is H or methyl; in certain preferred embodiments, $R^2$ is H. In other embodiments, $R^1$ and $R^2$ are taken together to form an optionally substituted 5- to 7-membered azacyclic ring, optionally containing an additional heteroatom selected from N, O and S.

In compounds of formula (III), $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted. In some embodiments of formula (III), $R^3$ is C1-C8 alkyl, C2-C10 alkenyl, C3-C8 cycloalkyl, C4-C9 cycloalkylalkyl, or C7-C14 arylalkyl, each of which may be optionally substituted. In preferred embodiments, the alkyl group comprising part of R3 is substituted with at least one substituent selected from the group consisting of OH, OMe, OAc, NH$_2$, NHMe, CH$_2$OH and NHAc.

In certain embodiments of formula (III), $R^3$ is a group of the form —CH(Z)R$^{10}$, where Z is OH, OR, CH$_2$OR, SR, and NR$_2$, where each R is independently H, optionally fluorinated C1-C4 alkyl, or optionally fluorinated C1-C4 acyl, and R$^{10}$ is C1-C6 alkyl, C2-C6 alkenyl, C1-C6 alkynyl, C3-C8 cycloalkyl, C3-C8 cycloalkylalkyl, C6-C12 aryl, C7-C20 arylalkyl, or a heteroform of one of these, each of which may be optionally substituted. In some embodiments, Z is OH, OMe, OAc, CH$_2$OH, SH, SMe, SAc, NH$_2$, NHMe, NMe$_2$, NHAc. In preferred embodiments, Z is OH. In other embodiments, Z is OH, OMe, OAc, NH$_2$, NHMe, or NHAc, and R$^{10}$ is C1-C4 alkyl, C3-C6 cycloalkyl, or optionally substituted phenyl.

In other embodiments of formula (III), $R^3$ is a group of the form —C(Z)R$^{10a}$R$^{10b}$, where Z is OH, OR, CH$_2$OR, SR, and NR$_2$, where each R is independently H, optionally fluorinated C1-C4 alkyl, or optionally fluorinated C1-C4 acyl, and each of R$^{10a}$ and R$^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or R$^{10a}$ and R$^{10b}$ may be taken together with the carbon to which they are attached to form a C3-C8 cycloalkyl or a C3-C8 heterocyclyl ring, which may be optionally substituted. In some such embodiments, Z is OH, OMe, OAc, CH$_2$OH, SH, SMe, SAc, NH$_2$, NHMe, NMe$_2$, NHAc. Sometimes, Z is OH, OMe, OAc, NH$_2$, NHMe, or NHAc. In certain preferred embodiments, Z is OH.

In specific embodiments of formula (III), the compound has the formula:

(III-A)

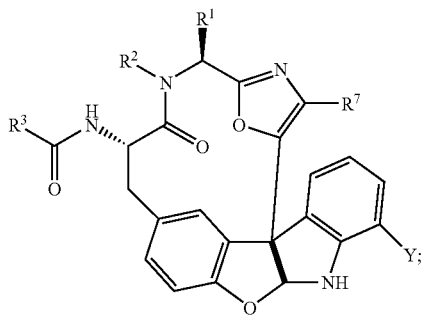

(III-B)

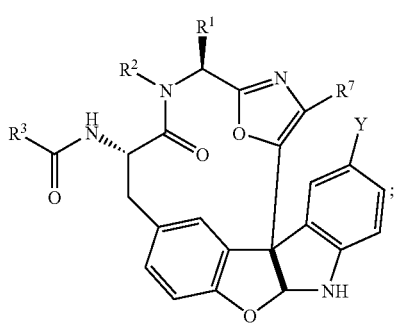

(III-C)

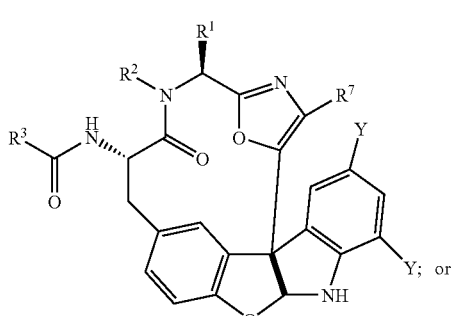

(III-D)

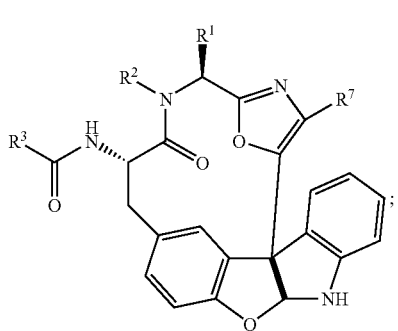

or a pharmaceutically acceptable salt or conjugate thereof.
It will be understood that references made to compounds and embodiments of formula (III) include compounds of formulae (III-A), (III-B), (III-C), and (III-D).

In some embodiments of formula (II) and formula (III), $R^7$ is —C(O)$NR^9{}_2$, where $R^9$ is defined as for formula (I). In preferred embodiments of formula (II) and formula (III), $R^7$ is an optionally substituted C6-C12 aryl, optionally substituted C5-C12 heteroaryl or optionally substituted C5-12 heterocyclyl ring. In some such embodiments, $R^7$ is an optionally substituted phenyl, naphthyl, benzimidazole, pyridinyl, pyrimidinyl, pyrazinyl or pyridazinyl ring. In other such embodiments, $R^7$ is an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole or tetrazole ring.

In compounds of formula (IV), $R^4$, $R^5$, $R^6$, $R^7$, Y, Y', m, and m' are defined as for formula (I). In compounds of formula (IV), X is O, S, NR" or $(CH_2)_n$, where n is 0-2, and R" is H, C1-C8 alkyl, C5-C8 aryl, C6-C12 arylalkyl, C1-C6 acyl, C6-C12 aroyl, alkylsulfonyl, or arylsulfonyl. In certain preferred embodiments, X is $(CH_2)_n$, where n is 0-2.

In some embodiments of formula (IV), $R^4$ is H or methyl, and $R^5$ is C(O)$R^3$, where $R^3$ is defined as for formula (I). In some such embodiments, $R^3$ is a group of the form —CH(Z)$R^{10}$ or —C(Z)$R^{10a}R^{10b}$, where Z is OH, OMe, OAc, $NH_2$, NHMe, or NHAc, and each of $R^{10}$, $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or $R^{10a}$ and $R^{10b}$ may be taken together with the carbon to which they are attached to form a C3-C8 cycloalkyl or a C3-C8 heterocyclyl ring, which may be optionally substituted.

In specific embodiments of formula (IV), the compound has the formula:

(IV-A)

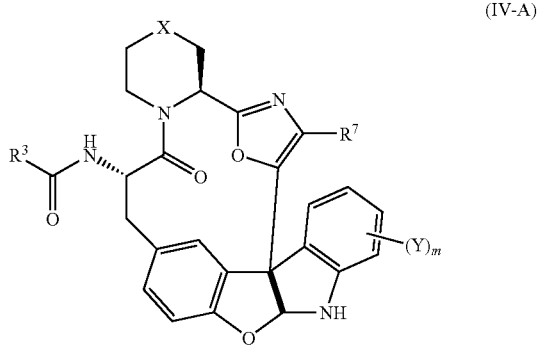

or a pharmaceutically acceptable salt or conjugate thereof; wherein $R^3$, X, $R^7$, Y, and m are defined as for formula (IV).

Specific embodiments described for formulae (I), (II) and (III) are also suitable for compounds of formula (IV), (V) or (VI).

In certain preferred embodiments, the invention provides a compound of formula (V) or formula (VI):

(V)

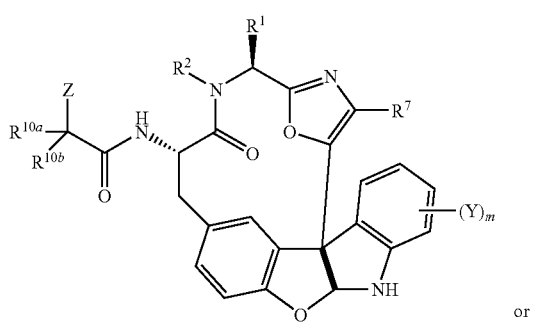

or

-continued

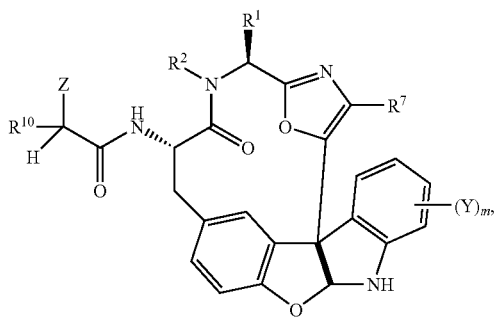

(VI)

or a pharmaceutically acceptable salt or conjugate thereof;
wherein $R^1$ is H, or C1-C8 alkyl, C2-C8 alkenyl, C2-C8 alkynyl, C1-C8 heteroalkyl, C2-C8 heteroalkenyl, C2-C8 heteroalkynyl, C6-C12 aryl, C7-C14 arylalkyl, C5-C12 heteroaryl, C6-C14 heteroarylalkyl, each of which may be optionally substituted;
$R^2$ is H, or C1-C8 alkyl, C1-C8 heteroalkyl, C7-C14 arylalkyl, C6-C14 heteroarylalkyl, each of which may be optionally substituted; or
$R^1$ and $R^2$ may be taken together with the atoms to which they are attached to form an optionally substituted 5- to 7-membered azacyclic ring, optionally containing an additional heteroatom selected from N, O, and S as a ring member;
$R^7$ is H, halo, optionally substituted C6-C12 aryl, optionally substituted C5-C12 heteroaryl, optionally substituted C5-C12 heterocyclyl, —CN, —COR$^8$, —COOR$^8$, or —C(O)NR$^9{}_2$;
$R^8$ is H, or C1-C8 alkyl, C2-C8 alkenyl, C6-C12 aryl, or C7-C14 arylalkyl, or a heteroform of one of these, each of which may be optionally substituted; and
each $R^9$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^9$ on the same N can cyclize to form an optionally substituted 3- to 8-membered azacyclic ring, optionally containing an additional heteroatom selected from N, O, and S as a ring member;
m is 0-4;
each Y is independently halo, OH, C1-C4 alkoxy, or C1-C8 alkyl, C2-C8 alkenyl, C2-C8 alkynyl, C6-C12 aryl, or C7-C14 arylalkyl, or a heteroform of one of these, each of which may be optionally substituted;
Z is OH, OR, CH$_2$OR, SR, and NR$_2$, where each R is independently H, optionally fluorinated C1-C4 alkyl, or optionally fluorinated C1-C4 acyl; and
each of $R^{10}$, $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or
$R^{10a}$ and $R^{10b}$ may be taken together with the carbon to which they are attached to form a C3-C8 cycloalkyl or a C3-C8 heterocyclyl ring, which may be optionally substituted.

In certain embodiments of formula (V) and formula (VI), $R^1$ is optionally substituted C1-C4 alkyl, C2-C4 alkenyl or C2-C4 alkynyl; in some such embodiments, $R^1$ is isopropyl.

In some embodiments, R2 is H or C1-C4 alkyl; sometimes, $R^2$ is H or methyl. In certain preferred embodiments, $R^2$ is H.

In other embodiments of formula (V) and formula (VI), $R^1$ and $R^2$ are taken together with the atoms to which they are attached to form an optionally substituted 5- to 7-membered azacyclic ring, optionally containing an additional heteroatom selected from N, O, and S as a ring member. In specific embodiments, $R^1$ and $R^2$ are taken together to form an optionally substituted 5- to 7-membered azacyclic ring containing no additional heteroatoms, i.e., an optionally substituted pyrrolidine, piperidine or homopiperidine ring. In other embodiments, $R^1$ and $R^2$ are taken together to form an optionally substituted 5- to 7-membered azacyclic ring containing an additional heteroatom selected from N, O and S. In some such embodiments, $R^1$ and $R^2$ are taken together to form an optionally substituted morpholine, thiomorpholine, piperazine, or homopiperazine ring.

In compounds of formula (V) and formula (VI), m is an integer from 0-4. In preferred embodiments, m is 0 or 1. In compounds of formula (V) and formula (VI), each Y is independently is halo, OH, or C1-C4 alkoxy, or is C1-C8 alkyl, C2-C8 alkenyl, C2-C8 alkynyl, C6-C12 aryl, or C7-C14 arylalkyl, or a heteroform of one of these, each of which may be optionally substituted. In certain embodiments, m is 1 and Y is halo, preferably chloro. In other embodiments, m is 0.

In compounds of formula (V) and formula (VI), Z is OH, OR, CH$_2$OR, SR, and NR$_2$, where each R is independently H, optionally fluorinated C1-C4 alkyl, or optionally fluorinated C1-C4 acyl. In certain embodiments, Z is OH, OMe, OAc, CH$_2$OH, SH, SMe, SAc, NH$_2$, NHMe, NMe$_2$, NHAc. In certain preferred embodiments, Z is OH.

In compounds of formula (V) each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted.

In some embodiments of formula (V), $R^{10a}$ and $R^{10b}$ are the same. In other embodiments, $R^{10a}$ and $R^{10b}$ are different. In certain preferred embodiments, each of $R^{10a}$ and $R^{10b}$ comprises at least two carbon atoms. For example, each of $R^{10a}$ and $R^{10b}$ may independently be ethyl, propyl, isopropyl, allyl, propargyl, n-butyl, s-butyl, isobutyl, t-butyl, pentyl, cyclopropyl, and the like; in some such embodiments, $R^{10a}$ and $R^{10b}$ are the same. In a preferred embodiment, each of $R^{10a}$ and $R^{10b}$ is ethyl.

In other embodiments, $R^{10a}$ and $R^{10b}$ are taken together with the carbon to which they are attached to form a C3-C8 cycloalkyl or a C3-C8 heterocyclyl ring, which may be optionally substituted. For example, $R^{10a}$ and $R^{10b}$ may be taken together to form an optionally substituted cyclopropyl, cyclobutyl, cyclopentyl, cyclopentenyl, cyclohexyl, cyclohexenyl, tetrahydrofuran, tetrahydropyran, tetrahydrothiofuran, tetrahydrothiopyran, pyrrolidine, or piperidine ring, and the like. In a preferred embodiment, each of $R^{10a}$ and $R^{10b}$ are taken together to form a cyclohexyl or a cyclopentyl ring. In some embodiments, the ring formed by $R^{10a}$ and $R^{10b}$ may be fused to a substituted or unsubstituted phenyl ring to provide, for example, and indenyl or tetrahydronaphthyl ring system.

In compounds of formula (VI), $R^{10}$ is C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted.

In compounds of formula (V) and formula (VI), $R^7$ is H, halo, optionally substituted C6-C12 aryl, optionally substituted C5-C12 heteroaryl, optionally substituted C5-C12 heterocyclyl, —CN, —COR$^8$, —COOR$^8$, or —C(O)NR$^9{}_2$.

In some embodiments, $R^7$ is $-C(O)NR^9{}_2$, where $R^9$ is defined as for formula (I). In preferred embodiments, $R^7$ comprises an optionally substituted aromatic, heteroaromatic or heterocyclic ring. In some such embodiments, $R^7$ is an optionally substituted phenyl, naphthyl, benzimidazole, pyridinyl, pyrimidinyl, pyrazinyl or pyridazinyl ring. In other such embodiments, $R^7$ is an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole or tetrazole ring.

In specific embodiments of formula (V) or formula (VI), the compound has the formula (V-A) or (VI-A), respectively:

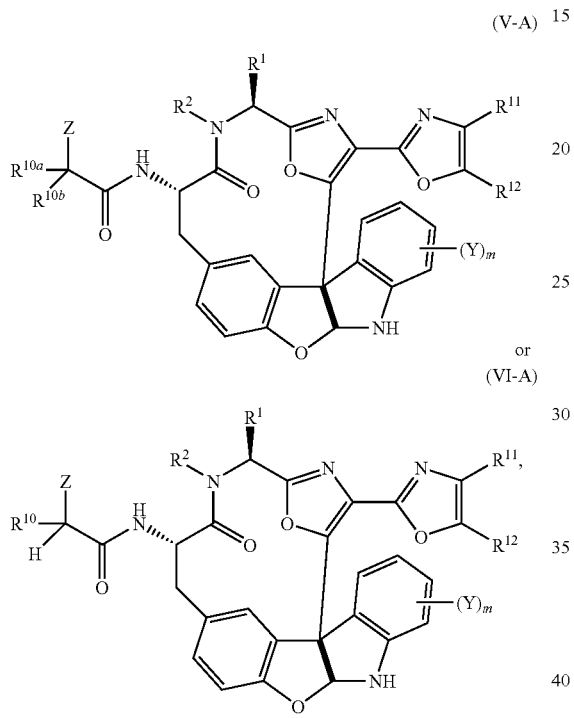

or a pharmaceutically acceptable salt or conjugate thereof;
wherein $R^1$, $R^2$, Z, Y, m, $R^{10}$, $R^{10a}$ and $R^{10b}$ are defined as for formula (V) and formula (VI); and each of $R^{11}$ and $R^{12}$ is independently H, halo, nitro, cyano, or optionally fluorinated C1-C4 alkyl, optionally fluorinated C1-C4 alkoxy, COOR$^{8'}$, CONR$^{9'}{}_2$, C6-C12 aryl or C5-C12 heteroaryl, each of which may be optionally substituted;

where $R^{8'}$ is H, or C1-C8 alkyl, C2-C8 alkenyl, C6-C12 aryl, or C7-C14 arylalkyl, or a heteroform of one of these, each of which may be optionally substituted; and each $R^{9'}$ is independently H, or C1-C12 alkyl, C1-C 12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^{9'}$ on the same N can cyclize to form an optionally substituted 3- to 8-membered azacyclic ring, optionally containing an additional heteroatom selected from N, O, and S as a ring member.

In some such embodiments, each $R^{11}$ and $R^{12}$ is independently H, halo, C1-C4 alkyl, COOR$^{8'}$, or CONR$^{9'}{}_2$; or is C6-C12 aryl or C5-C12 heteroaryl, each of which may be optionally substituted.

In specific embodiments of formulae (I)-(VI), $R^7$ is an optionally substituted heterocyclic or heteroaromatic ring of the formula:

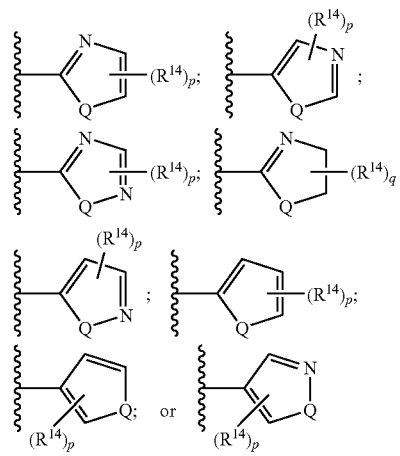

wherein Q is O, S or NR$^{13}$, where R$^{13}$ is H or C1-C4 alkyl;
each $R^{14}$ is independently halo, nitro, cyano, or optionally fluorinated C1-C4 alkyl, optionally fluorinated C1-C4 alkoxy, COOR$^{8'}$, CONR$^{9'}{}_2$, C6-C12 aryl or C5-C12 heteroaryl, each of which may be optionally substituted;
where $R^{8'}$ is H, or C1-C8 alkyl, C2-C8 alkenyl, C6-C12 aryl, or C7-C14 arylalkyl, or a heteroform of one of these, each of which may be optionally substituted; and
each $R^{9'}$ is independently H, or C1-C12 alkyl, C1-C 12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^{9'}$ on the same N can cyclize to form an optionally substituted 3- to 8-membered azacyclic ring, optionally containing an additional heteroatom selected from N, O, and S as a ring member;
p is 0-3; and
q is 0 to 4.

In certain preferred embodiments of formulae (I)-(VI), $R^7$ is

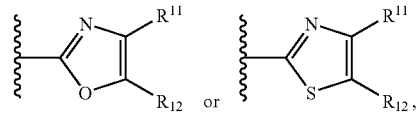

wherein each $R^{11}$ and $R^{12}$ is independently H, halo, nitro, cyano, or optionally fluorinated C1-C4 alkyl, optionally fluorinated C1-C4 alkoxy, COOR$^{8'}$, CONR$^{9'}{}_2$, C6-C12 aryl or C5-C12 heteroaryl, each of which may be optionally substituted;
where $R^{8'}$ is H, or C1-C8 alkyl, C2-C8 alkenyl, C6-C12 aryl, or C7-C14 arylalkyl, or a heteroform of one of these, each of which may be optionally substituted; and
each $R^{9'}$ is independently H, or C1-C12 alkyl, C1-C 12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^{9'}$ on the same N can cyclize to form an optionally substituted 3- to 8-membered azacyclic ring, optionally containing an additional heteroatom selected from N, O, and S as a ring member. In some such embodiments, each $R^{11}$ and $R^{12}$ is independently H, halo, C1-C4 alkyl, $COOR^{8'}$, or $CONR^{9'}_2$; or is C6-C12 aryl or C5-C12 heteroaryl, each of which may be optionally substituted.

Where chiral carbons are included in chemical structures, unless a particular orientation is depicted, both stereoisomeric forms are intended to be encompassed. Compounds of formulae (I), (II), (III), (IV), (V) and (VI) may, for example, have two or more asymmetric centers and therefore exist in different enantiomeric and/or diastereomeric forms. All optical isomers and stereoisomers of the compounds described herein, and mixtures thereof, are considered to be within the scope of the invention, including the racemate, one or more enantiomeric forms, one or more diastereomeric forms, or mixtures thereof. In particular, racemic mixtures of single diastereomers such as the ones described, diastereomers having an diastereomeric excess (d.e.) of greater than 90% or greater than about 95%, and enantiomers having an enantiomeric excess (e.e.) of greater than 90% or greater than about 95%. Similarly, where double bonds are present, the compounds can exist in some cases as either cis or trans isomers; the invention includes each isomer individually as well as mixtures of isomers. Where the compounds described may also exist in tautomeric forms, this invention relates to the use of all such tautomers and mixtures thereof.

Compounds of formulae (I), (II), (III), (IV), (V) and (VI) can be supplied in free base form, or can be supplied as a pharmaceutically acceptable salt, or as a mixture of the free base form and the corresponding salt. The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases that could be used include trimethylamine, triethylamine, pyridine, picoline, ethanolamine, diethanolamine, triethanolamine, dicyclohexylamine, N,N'-dibenzylethylenediamine, etc.

Suitable salts include those of inorganic acids such as hydrochlorides, hydrobromides, sulfates, hydrosulfates, and the like, or organic acid addition salts. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In addition, compounds of formulae (I), (II), (III), (IV), (V) and (VI) may be coupled to moieties such as targeting agents. Among such targeting agents are antibodies or immunologically active fragments thereof, including single-chain antibody forms directed against tumor antigens or against receptors or integrins associated with tumors, peptidomimetics directed against these moieties, and the like. In addition, compounds of formulae (I), (II), (III), (IV), (V) and (VI) may be coupled to an excipient such as polyethylene glycol for altering pharmacokinetics. The selected PEG may be of any convenient molecular weight, and may be linear or branched, and may be optionally conjugated through a linker. The average molecular weight of PEG will preferably range from about 2 kiloDalton (kDa) to about 100 kDa, more preferably from about 5 kDa to about 40 kDa.

Compounds of formulae (I), (II), (III), (IV), (V) and (VI) are useful in treating or ameliorating cell proliferative diseases. In particular, the compounds and methods described herein are useful for the treatment or amelioration of tumors and malignancies associated with breast, ovary, lung (SCLC and NSCLC), colon, rectum, prostate, testes, skin (e.g., melanoma, basal cell carcinoma, and squamous cell carcinoma), pancreas, liver, kidney, brain (e.g., glioma, meningioma, schwannomas, and medulloblastomas), and the blood and hematopoietic system, including, e.g., leukemia, non-Hodgkins lymphoma, and multiple myeloma.

In the methods described herein, for example, cell proliferation may be reduced, and/or cell death, such as apoptosis or apoptotic cell death, may be induced. The cell proliferative disorder may be a tumor or non-tumor cancer in a human or animal subject.

The compounds and methods provided herein for reducing cell proliferation and/or inducing cell death may be used alone, or in conjunction with or in combination with surgical, radiation, chemotherapeutic, immunotherapy, and bone marrow and/or stem cell transplantation methods, or with other palliative agents, such as compounds that aid in nutrition or general health, anti-emetic agents, and the like.

In some embodiments, the compounds of the present invention are administered in combination with a chemotherapeutic agent, and used to reduce cell proliferation, induce cell death, and/or treat or ameliorate a cell proliferative disorder.

The compounds described herein are also useful against certain drug resistant tumors and cancer cell lines, in particular against cancers that are resistant to TAXOL® and/or vinca alkaloid anti-cancer agents.

Where an additional chemotherapeutic drug is administered, it is typically one known to have cytostatic, cytotoxic or antineoplastic activity. These agents include, without limitation, antimetabolites (e.g., cytarabine, fludaragine, 5-fluoro-2'-deoxyuridine, gemcitabine, hydroxyurea, methotrexate); DNA active agents (e.g., bleomycin, chlorambucil, cisplatin, cyclophosphamide); intercalating agents (e.g., adriamycin and mitoxantrone); protein synthesis inhibitors (e.g., L-asparaginase, cycloheximide, puromycin); topoisomerase type I inhibitors (e.g., camptothecin, topotecan or irinotecan); topoisomerase type II inhibitors (e.g. etoposide, teniposide anthraquinones, anthracyclines and podophyllotoxin); microtubule inhibitors (e.g., taxanes, such as paclitaxel and docetaxel, colcemid, colchicines, or vinca alkaloids, such as vinblastine and vincristine); kinase inhibitors (e.g. flavopiridol, staurosporin and hydroxystaurosporine), drugs that affect Hsp90 (e.g. geldanomycin and geldanomycin derivatives, radicicol, purine derivatives and antibodies or antibody fragments that selectively bind to Hsp90), TRAIL, a TRAIL receptor antibody, TNF-α or TNF-β, and/or radiation therapy.

In some preferred embodiments, the additional cancer therapeutic agent is TRAIL, a TRAIL receptor antibody, TNF-α or TNF-β. In other preferred embodiments, the additional drugs for co-administration with the compounds of the invention affects Hsp90 (heat-shock protein 90).

Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets*, 3, 359-69 (2003), and in Yamamoto, et al., *Angew. Chem.*, 42, 1280-84 (2003); and in Moulin, et al., *J. Amer. Chem. Soc.*, vol 127, 6999-7004 (2005); purine derivatives such as PU3, PU24FCI and PUH64 (see Chiosis et al., *ACS Chem. Biol.* Vol. 1(5), 279-284 (2006) and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett.*, vol. 15, 3338-43 (2005). Antibodies or antibody fragments that selectively bind to Hsp90 may also be administered as drugs to cause inhibition of Hsp90, and can be used in combination with the compounds of the invention.

Where a compound described herein is utilized in conjunction with or in combination with another therapeutic, the two agents may be co-administered, or they may be administered separately where their administration is timed so the two agents act concurrently or sequentially.

Accordingly, the compositions used in the methods described herein include at least one compound of the invention, and can optionally include one or more additional cytotoxic or cytostatic therapeutic such as, but not limited to, those disclosed above. Similarly, the methods of the invention include methods wherein a subject diagnosed as in need of treatment for cancer is treated with at least one compound or composition of the invention, and is simultaneously or concurrently treated with one or more of the additional therapeutic agents described above.

Formulation and Administration

The formulations useful in the invention include standard formulations such as those set forth in *Remington's Pharmaceutical Sciences*, latest edition, Mack Publishing Co., Easton, Pa., incorporated herein by reference. Such formulations include those designed for oral delivery, slow release, topical administration, parenteral administration, or any other suitable route as determined by an attending physician or veterinarian. Thus administration may be systemic or local. Suitable vehicles or excipients include liposomes, micelles, nanoparticles, polymeric matrices, buffers, and the full range of formulations known to practitioners.

Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

Regardless of the route of administration selected, the compounds described herein, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

For administration to animal or human subjects, the dosage of a compound of the invention is typically 10-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

Synthetic Processes

Indolines of formula (I) have been prepared through a novel and efficient multi-step process, as shown in Scheme 1. A key step in the process involves the electrochemical oxidative cyclization of a phenolic intermediate to provide an indoline compound of formula (I), which may be further functionalized as exemplified by the compounds described herein. The oxidative cyclization was described in U.S. application Ser. No. 12/134,984, filed 6 Jun. 2008, and published as US 2009/0005572, the contents of which are incorporated herein by reference in their entirety. Compounds of formula (II), (III), (IV), (V) and (VI) are prepared analogously.

As shown in Scheme 1, dipeptide starting materials were prepared under standard conditions known in the art, for example, by coupling an N-hydroxysuccinimide ester or another activated ester of a protected amino acid with serine. It will be understood by one of skill in the art that a wide variety of suitable conditions may be utilized to form the dipeptide starting materials, including the extensive body of literature describing synthesis of peptides and peptide mimetics.

The dipeptide was reacted with an optionally substituted indole and an activating reagent, optionally in the presence of a protic acid, to provide an indole-containing dipeptide. Suitable activating reagents include, for example, carboxylic acid anhydrides, mixed anhydrides, or acyl halides (e.g., acetic anhydride, trifluoroacetic anhydride, acetyl chloride, oxalyl chloride), sulfonic acid anhydrides or halides (e.g., methanesulfonic anhydride, trifluoromethanesulfonic anhydride, methanesulfonyl chloride), mineral acid halides (e.g., thionyl chloride, or phosphoryl chloride), and the like.

In a preferred embodiment, the activating agent was acetic anhydride, and the reaction was conducted in acetic acid as a protic solvent. In a particularly preferred embodiment, the dipeptide and an optionally substituted indole were reacted with acetic anhydride in acetic acid at about 80° C., to provide the desired compound.

The preparation of N-acetyl tryptophan derivatives by reaction of serine or N-acetyl serine and an optionally substituted indole in acetic anhydride and acetic acid has been previously reported. Y. Yokoyama, et al., *Tetrahedron Letters* (1999), 40: 7803; Y. Yokoyama, et al., *Eur. J. Org. Chem.* (2004), 1244; Y. Konda-Yamada, et al., *Tetrahedron* (2002), 58: 7851; M. W. Orme, et al., U.S. Pat. No. 6,872,721. However, the preparation of other acylated tryptophan derivatives under these conditions, such as the dipeptide analogs of the present invention, has not been previously described to our knowledge.

Esterification of the free carboxylic acid, followed by oxidative cyclization of the dipeptide intermediate with an oxidizing agent, for example, DDQ, provided an oxazole intermediate. It will be understood by those in the art that other oxidative conditions could be utilized, such as, for example, the use of 7,7,8,8-tetracyanoquinodimethane (TCNQ), ceric ammonium nitrate, hypervalent iodide reagents, and the like.

Deprotection of the protected amino group, if present, and amide bond formation provided a phenolic intermediate. Electrochemical oxidative cyclization of the phenolic intermediate provided a macrocyclic indoline compound. Such compounds were further elucidated to compounds of formula (I) through a series of straightforward chemical transformation. For example, deprotection of the carboxylate ester followed by amide bond formation provided embodiments wherein $R^7$ is $C(O)NR^9{}_2$. Removal of the Cbz group and acylation or amide bond formation was used to provide compounds of formula (I), wherein $R^5$ is an acyl substituent, for example —$C(O)R^3$. Sulfonylation, reductive alkylation, or N-alkylation of the same amine could be used to provide a compound wherein $R^5$ is a sulfonyl (i.e., —$SO_2R$ or —$SO_2Ar$) or an alkyl, alkenyl, alkynyl, arylalkyl, or a heteroform of one of these groups. Other transformations to install a substituent at $R^5$, for example, carbamoylation or urea formation, are also envisioned. One of skill in the art will understand that the order of these steps could be reversed, depending on the nature of the functional groups to be installed, and the protecting groups utilized.

Scheme 1 provides a general synthetic route useful for the preparation of macrocyclic indoline compounds of formula (I). Those skilled in the art will appreciate that certain reaction conditions can be varied without altering the essence of the present invention. For example, coupling reactions can be accomplished with a variety of activated esters, such as by way of example only N-hydroxybenzotriazole ester, perfluorophenyl ester, N-hydroxyphthalimide esters, activated esters generated by the reaction of the carboxylic acid with a carbodiimide, and other activated esters conventionally used for acylation of an amine to form amide bonds. In addition, while amino groups are conveniently protected as carbobenzyloxy (Cbz) group, one of skill in the art will recognize that other suitable protecting groups could be utilized. Suitable protecting groups and methods to attach and remove them are well known in the art, and are described, for example, in T. H. Greene, PROTECTIVE GROUPS IN ORGANIC SYNTHESIS, 2$^{nd}$ ed.

Scheme 1

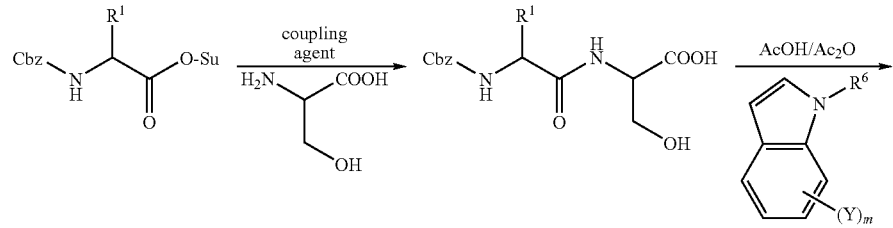

-continued

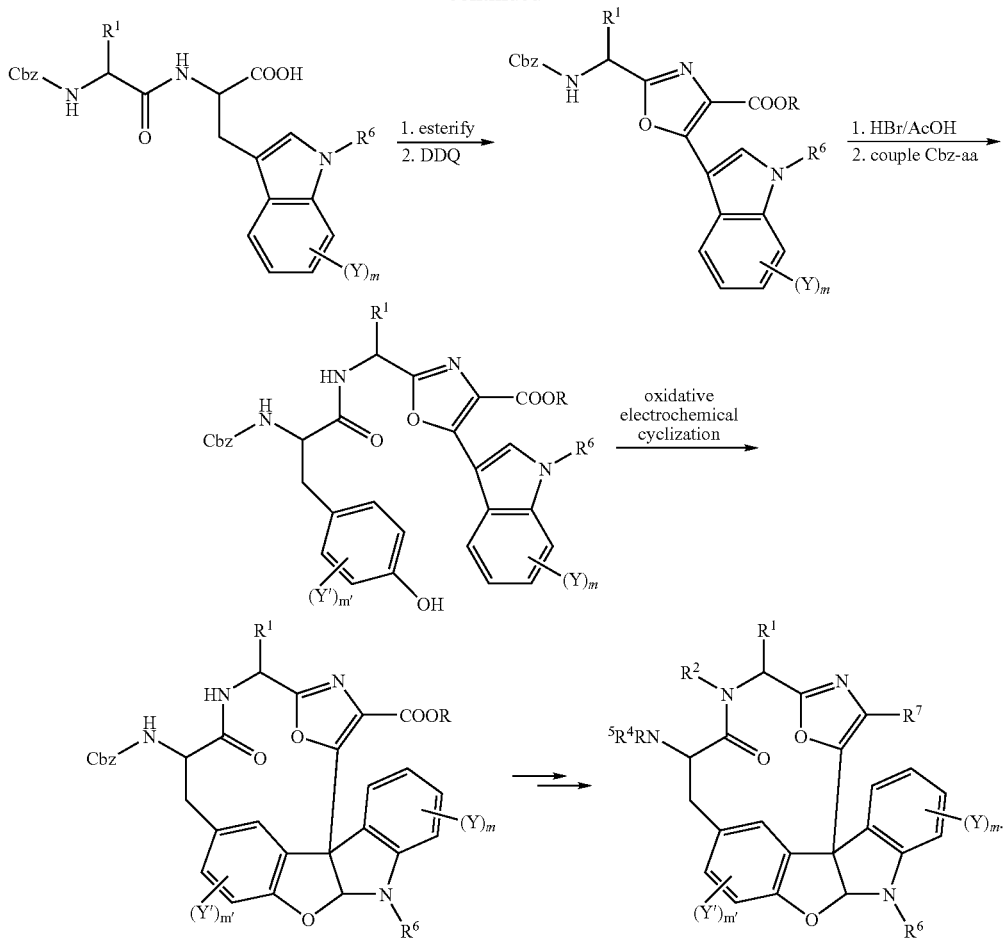

The process described in Scheme 1 is useful for the preparation of indolines of formula (I) in high yield and purity. In particular, the compounds of the present invention are available in good yield and with high diastereomeric purity, preferably in greater than 95% diastereomeric excess, sometimes 98% diastereomeric excess.

The following examples are offered to illustrate but not to limit the invention.

EXAMPLE 1

Step A:

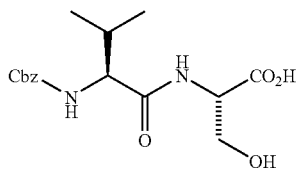

L-Serine (104.19 g, 991 mmol) was dissolved in water (1440 mL) in a 4-L Erlenmeyer flask. Solid NaHCO₃ (83.25 g, 991 mmol was added and the mixture was stirred at RT to give a clear solution. Cbz-Val-OSu (300.0 g, 861 mmol) was added as a solution in 1,4-dioxane (1500 mL), with additional 1,4-dioxane (220 mL) used to rinse. The resulting cloudy mixture became clear after 1.5 h of stirring at 25° C. After 44 h, the mixture was divided into two equal portions. Methanol (700 mL) and 12 N aqueous HCl (42 mL, 504 mmol) was added to each portion, followed by EtOAc (1000 mL) and a solution of NaCl (100 g) dissolved in water (600 mL). The layers were separated and the organic layer was washed with saturated aqueous NaCl (350 mL). The aqueous layers were extracted in succession with EtOAc (1000 mL). The organic layers resulting from work-up of both portions of the reaction were combined, dried (Na₂SO₄), filtered, and evaporated to give 351 g of white solid. This material was suspended in CH₂Cl₂ (1500 mL) and stirred for 2 h. The mixture was filtered and the crystals were washed with CH₂Cl₂ (1000 mL) to give Cbz-Val-Ser-OH as 262.3 g of white crystals (90% yield). MS: m/z=339.1 (M+1).

Step B:

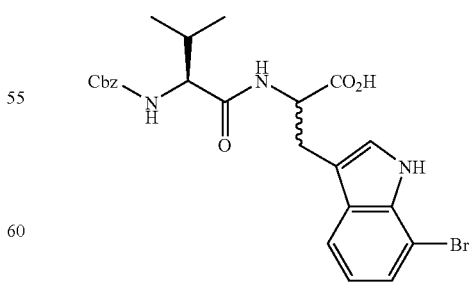

Acetic acid (180 mL) was added to Cbz-Val-Ser-OH from Step A above (42.89 g, 127 mmol) and 7-bromoindole (30.96 g, 158 mmol) in a round-bottom flask fitted with a mechanical stirrer, reflux condenser, and internal thermometer. Acetic anhydride (40 mL, 43 g, 420 mmol) was added and the mixture was heated to 80° C. over 40 min. Heating was continued at this temperature for 4 h. After cooling to RT and standing overnight, the mixture was diluted with ethyl ether (180 ml) and stirred for 30 min. The mixture was filtered and the crystals were washed with ethyl ether (250 mL). Drying of the crystals yielded 42.49 g of product (65% yield). MS: m/z=516.0 (M+1).

Step C:

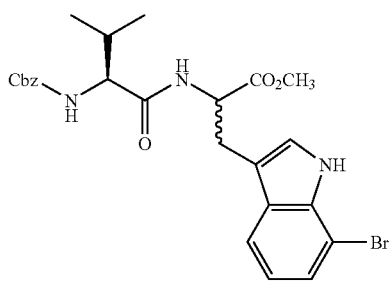

Concentrated aqueous HCl (60 ml, 720 mmol) was added to a stirred suspension of the compound synthesized in Step B above (32.53 g, 63.0 mmol) in 2,2-dimethoxypropane (1200 mL, 1020 g, 9.8 mol). After stirring for 24 h at 25° C., most of the solvent was evaporated to give wet crystals. MTBE (250 mL) was added and mixture was allowed to stand with occasional swirling over 3 h. Filtration and washing of the crystals with MTBE (100 mL) gave 30.31 g of product (91% yield). MS: m/z=530.1 (M+1).

Step D:

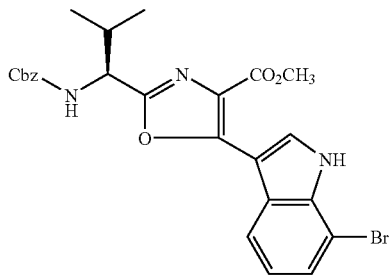

A solution of DDQ (28.41 g, 125 mmol) in THF (251 g, 282 mL) was added to compound synthesized in Step C above (30.20 g, 56.9 mmol) in THF (848 g, 954 mL) and the dark solution was heated to gentle reflux in an oil bath at 85° C. for 6 h. After cooling and standing overnight at RT, the solvent was removed on a rotary evaporator. Methanol (200 mL) was added and the solvent was evaporated to leave 91 g of brown crusty solid. Methanol (200 mL) was added and the solid was loosened with a spatula. The mixture was swirled until the appearance changed to a red liquid containing a yellow precipitate. The mixture was filtered and the precipitate was washed with methanol (60 mL). The pale gray crystals were air dried and then dried under vacuum to give 17.98 g of product (60% yield). MS: m/z=526.0 (M+1).

Step E:

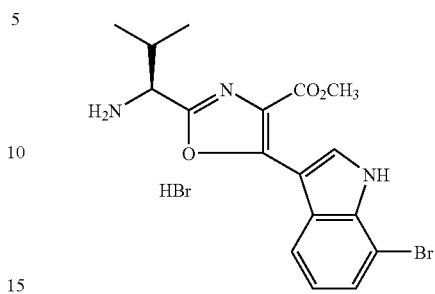

Glacial acetic acid (25 mL) was added to the Cbz derivative synthesized in Step D above (9.99 g, 19.0 mmol) in a 500-mL round bottom flask fitted with a mechanical stirrer. The suspension was stirred at 25° C. and 33% HBr in acetic acid (50 mL) was added in one portion. The mixture became homogeneous and then a precipitate formed in 5-10 min. After 1 h, MTBE (235 mL) was added and stirring was continued at 25° C. for another 1 h 20 min. The mixture was filtered and the precipitate was washed with MTBE (150 mL). The cream-colored powder was dried under vacuum to a weight of 8.91 g (99% yield). MS: m/z=392.0 (M+1).

Step F:

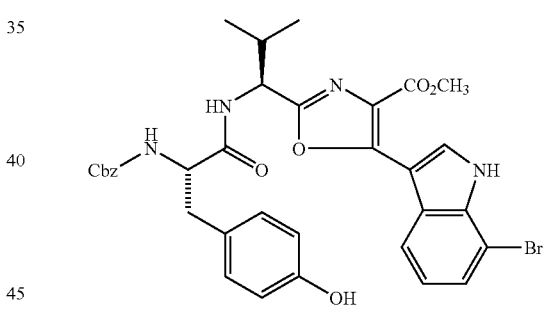

DMF (100 mL) was added to the amine salt synthesized in Step E above (9.16 g, 19.4 mmol), HOBt (3.17 g, 23.5 mmol), and CBZ-Tyr-OH (6.44 g, 20.4 mmol) in a round bottom flask. N,N-Diisopropylethylamine (4.22 mL, 3.13 g, 129 mmol) was added, followed by EDC (4.15 g, 21.6 mmol). After stirring for 24 h at 25° C., the solution was diluted with EtOAc (500 mL) and the mixture was washed with 1 N aqueous HCl (250 mL), saturated aqueous NaHCO₃ (250 mL), and saturated aqueous sodium chloride (250 mL). The solution was dried (Na₂SO₄), decanted, and evaporated to give a tan solid. This material was dissolved in 2-PrOH (180 mL) at 90° C. Hexanes (85 mL) were added and the solution was allowed to cool to RT. After standing overnight, the mixture was cooled to 5° C. for 4 h. The solid was separated by filtration and washed with 1:12-PrOH/hexanes (140 mL). This material, which at this point held residual solvent, was dried on a vacuum manifold to give 11.58 g of product (87% yield). MS: m/z 689.0 (M+1).

Step G:

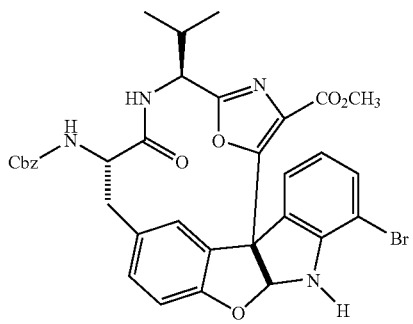

An electrochemical cell was assembled using a polyethylene cylinder (15 cm diameter×30 cm height) and a custom rack (polypropylene and nylon) which supported 48 vertical graphite rods (6.15 mm diameter×30 cm length). The rods were arranged in a pattern of three concentric rings with 12 and 24 anodes in the inner and outer rings, respectively. The intermediate ring contained 12 cathodes, separated from adjacent anodes by approximately 7 mm. Electrodes were immersed to a depth of 24 cm. The phenolic material synthesized in Step F above (20.00 g, 29.0 mmol) and $Et_4NBF_4$ (70.00 g, 322 mmol) were dissolved in DMF (4000 mL), and. KOH (~86%, 1.68 g, 26 mmol) was added in 10 mL of water. The solution was stirred vigorously by two 4-bladed turbines (50 mm diameter, blades at 45°, approx. 680 rpm) on a single shaft. The electrochemical reaction was carried out at a potential of 1.5-1.6 volts. Additional phenolic starting material (20.00 g, 20.00 g, 20.00 g, and 7.94 g) was added as a solid, along with KOH (~86%, 1.60 g, 1.63 g, 1.53 g, and 0.65 g) in water (5.0 mL, 5.0 mL, 5.0 mL, and 2.0 mL) on days 3, 5, 8, and 10, respectively. After 13 days, approximately 27.7 amp-h of current had passed, and 5.8% of the original SM remained as determined by HPLC integration at 220 nM. The reaction mixture was concentrated on a rotary evaporator (bath temp. ≦35° C.) and dried further on a vacuum manifold. The residue was partitioned between EtOAc (1200 mL) and 0.5 N aqueous HCl (600 mL). The organic layer was washed with saturated aqueous $NaHCO_3$ (250 mL) and then saturated aqueous NaCl (250 mL). The aqueous layers were extracted in succession with EtOAc (2×250 mL). The combined organic layers were dried ($Na_2SO_4$), decanted and evaporated to give 70.1 g of crude product. This material was purified by flash column chromatography in three portions. Each portion used silica gel (283 g) with 25% EtOAc in $CH_2Cl_2$ (approx. 2.4 L for packing column and elution). This yielded 35.6 g (41% yield) of product as a mixture of stereoisomers (83.5: 13.6 as measured by HPLC integration at 220 nM). MTBE (500 mL) was added and the mixture was stirred at RT for 2 h. After standing an additional 3 h, the mixture was filtered and the solid was washed with MTBE (3 portions, 100 mL total). HPLC analysis of the filtrate showed 94.8% purity (94.8:2.1 stereoisomer ratio measured by integration at 220 nm). The filtrate was evaporated and the resulting residue was dried under vacuum to yield 31.99 g of product (36% yield) of as a pale yellow solid. MS: m/z=687.0 (M+1).

EXAMPLE 2

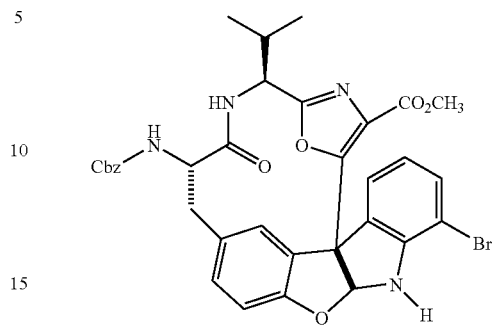

To a three-neck round-bottom flask equipped with a thermometer, an addition funnel and a magnetic stir bar was added the methyl ester synthesized in Step G of Example 1 (530 mg, 0.77 mmol) and methanol (18 mL). The solution was cooled to 0° C. in ice-water bath followed by addition of LiOH in water (324 mg/5 mL, 7.7 mmol, 10 eq.) at 0° C. with stirring. After the addition the reaction mixture became a slurry. The cooling bath was removed and the mixture was allowed to warm to RT. The precipitate disappeared gradually. After 4.5 h stirring at RT less than 2% of SM remained as determined by LCMS. Ice (40 g) was added to the reaction mixture and 1 N aqueous HCl (10 mL) was added dropwise from an addition funnel with vigorous stirring to acidify the 0° C. reaction mixture. The pH of the mixture was adjusted to 2.5-3.0. A pale yellow solid precipitated, which was extracted using EtOAc (2×50 mL). The aqueous phase was concentrated to remove most of the methanol and then extracted with EtOAc (2×50 mL). The combined organic layers was dried over $Na_2SO_4$ and concentrated to afford crude product (516 mg, 0.77 mmol, ca. 96% pure and containing by-product hydantoin) which was used directly in the next step without further purification. MS: m/z=673.2 (M+1).

EXAMPLE 3

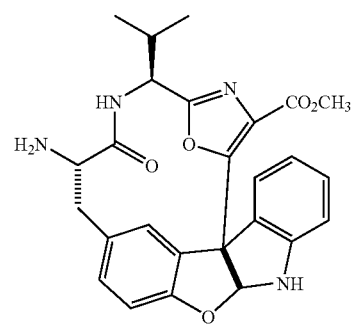

The compound synthesized in Step G of Example 1 (200 mg, 0.291 mmol) was dissolved in methanol (12 mL). N,N-Diisopropylethylamine (0.100 mL, 74 mg, 0.57 mmol) and 10% palladium on carbon (40 mg) were added and the mixture was stirred under an atmosphere of hydrogen for 3 h. The mixture was filtered through a pad of Celite and the catalyst was washed with additional methanol. The filtrate was evaporated and the residue was partitioned between EtOAc (30 mL) and saturated aqueous NaHCO₃ (10 mL). The organic layer was washed with saturated aqueous NaCl (10 mL), dried (Na₂SO₄), decanted and evaporated to give the amine product. MS: m/z=475.1 (M+1).

EXAMPLE 4

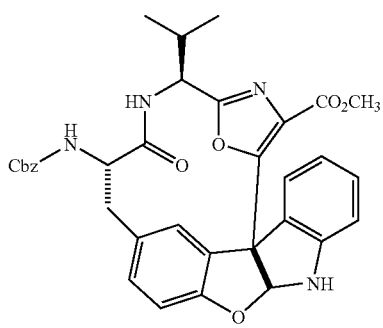

The compound synthesized in Example 3 (138 mg, 0.291 mmol) was dissolved in THF (5.5 mL) and the solution was stirred at RT. 4-Methylmorpholine (0.052 mL, 44 mg, 0.43 mmol) was added followed benzyl chloroformate (0.046 mL, 55 mg, 0.32 mmol). After 1.5 h, the reaction mixture was diluted with EtOAc (30 mL) and washed with 1 N aqueous HCl, saturated aqueous NaHCO₃, and saturated aqueous NaCl (10 mL of each). The organic layer was dried (Na₂SO₄), decanted, and evaporated. The residue was purified by flash column chromatography on silica gel, eluting with 30% EtOAc in CH₂Cl₂, to give 148 mg of the Cbz-protected product. MS: m/z=609.1 (M+1).

EXAMPLE 5

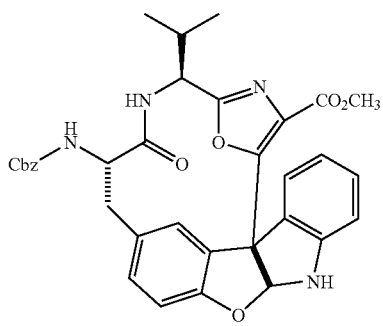

The compound synthesized in Example 4 (641 mg, 1.05 mmol) was dissolved in methanol (22 mL) and the solution was cooled in an ice bath. A solution of LiOH.H₂O (440 mg, 10.5 mmol) in water (4.0 mL) was added over 5 min. The ice bath was removed and the mixture was stirred for 5 h. The mixture was the cooled in an ice bath and water (30 mL) was added followed by 1 N aqueous HCl (11 mL), keeping the reaction temperature below 10° C. The mixture was partitioned between water (15 mL) and EtOAc (50 mL), and the organic layer was washed with saturated aqueous NaCl. The aqueous layers were extracted in succession with EtOAc (30 mL). The combined organic layers were dried (Na₂SO₄), decanted, and evaporated to give the acid product as fine white crystals. MS: m/z=595.2 (M+1).

EXAMPLE 6

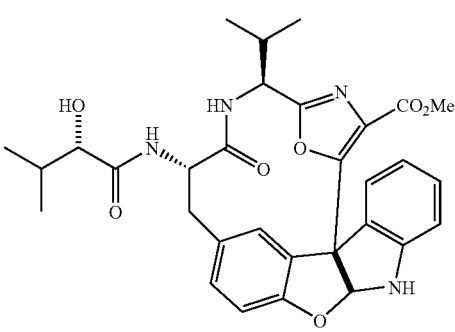

To a dry 15-mL flask containing the amine synthesized in Example 3 (23 mg, 0.0485 mmol) were added anhydrous THF (1 mL), N-hydroxysuccinimide ester of (S)-2-hydroxy-3-methylbutyric acid (12.5 mg, 0.0582 mmol, 1.2 eq.) and Na₂CO₃ (8 mg, 0.097 mmol, 2 eq.) at RT under N₂. The resulting reaction solution was stirred for 3 h. Less than 10% of SM remained. All solvent was evaporated under reduced pressure and the residue was dissolved in EtOAc (30 mL) washed with saturated aqueous NaHCO₃ (10 mL), water (2×10 mL) and brine (10 mL), and dried over Na₂SO₄. The solution was concentrated and the crude product was purified by PTLC eluting with MeOH/CH₂Cl₂ (6/94) to afford desired product as an off-white solid (25 mg, 0.0435 mmol, 90%). MS: m/z=575.1 (M+1).

EXAMPLE 7

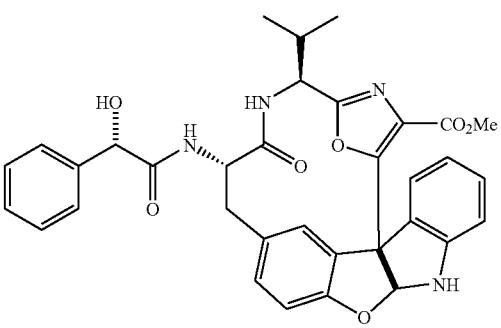

The compound synthesized in Example 3 (20 mg, 0.042 mmol) was dissolved in DMF (0.80 mL) along with (S)-mandelic acid (7 mg, 0.046 mmol) and HOBt (7 mg, 0.052 mmol). A few 3A molecular sieve pellets were added, followed by EDC (10 mg, 0.052 mmol). After stirring at RT for 2.5 h, the reaction mixture was diluted into EtOAc (30 mL) and washed with 1 N aqueous HCl (15 mL), saturated aqueous NaHCO₃ (15 mL) and saturated aqueous NaCl (10 mL). The organic layer was dried (Na₂SO₄), decanted, and evaporated. The crude product was purified by flash column chromatography on silica gel, eluting with 2% methanol in 1:1 EtOAc/CH₂Cl₂ to give 17 mg of amide product. MS: m/z=609.0 (M+1).

EXAMPLES 8-10

The products of Examples 8 and 9 were prepared by coupling the amine from Example 3 with (R)-tetrahydro-2-furoic acid and (S)-2-hydroxyisocaproic acid, respectively, under the conditions used for Example 7. In the case of Example 10, the product was prepared by reaction of 3,4,5-trimethoxybenzoyl chloride with the amine from Example 3.

|  | | MS m/z |
|---|---|---|
| Example 8 | 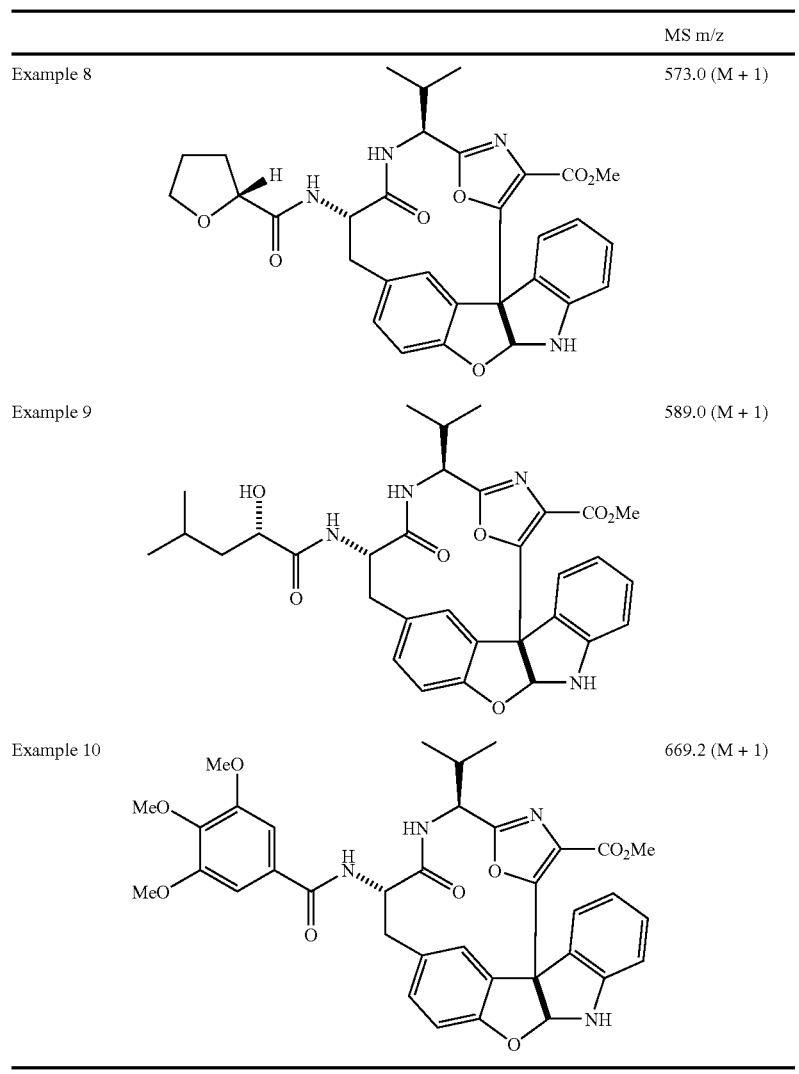 | 573.0 (M + 1) |
| Example 9 | | 589.0 (M + 1) |
| Example 10 | | 669.2 (M + 1) |

EXAMPLE 11

Step A:

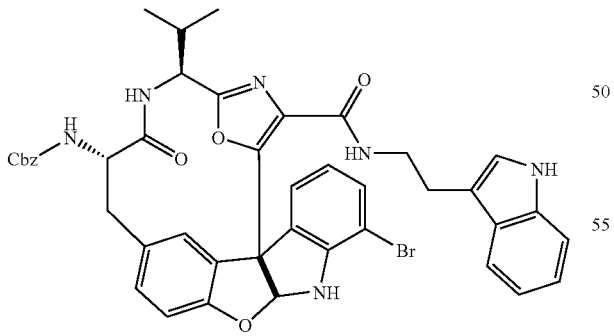

To a dry 15-mL flask containing a magnetic stir bar were added the carboxylic acid from Example 2 (22 mg, 0.0327 mmol), tryptamine (5.2 mg, 0.0327 mmol, 1.0 eq.), HOBt (4.4 mg, 0.0327, 1.0 eq.), anhydrous DMF (1 mL) and N,N-diisopropylethylamine (0.0057 mL, 0.0327 mmol, 1.0 eq.). The reaction mixture was cooled to 0° C. followed by addition of EDC (6.3 mg, 0.0327 mmol, 1.0 eq.). The resulting reaction mixture was stirred at RT for 16 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed with water (20 mL), 10% aqueous NaHSO$_4$ (20 mL), water (20 mL), saturated NaHCO$_3$ (20 mL), and brine (2×20 mL), and then dried over Na$_2$SO$_4$. After concentration the crude product was purified by PTLC eluting with MeOH/CH$_2$Cl$_2$ (6/94) to afford desired product as an off-white solid (15 mg, 0.0184 mmol, 56%). MS: m/z=815.1 (M+1).

Step B:

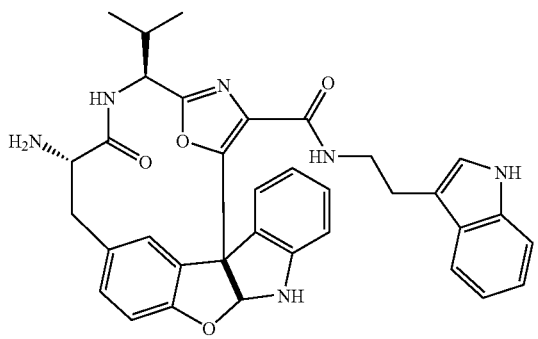

To a 15-mL flask containing material synthesized in Step A above (15 mg, 0.0184 mmol) was added methanol (1 mL) and Pd/C (10%) (9.8 mg, 0.0092 mmol, 0.5 eq.) under $N_2$. $H_2$ balloon was added and the flask was purged with $H_2$ for 4 times. Then $H_2$ balloon was opened to the reaction system. After 3 h stirring almost no starting material remained. The reaction was stopped. The reaction mixture was filtered through a pad of Celite and the black cake was washed with methanol (3×1 mL). The filtrate was concentrated and the residue was used in next step directly without further purification.

Step C:

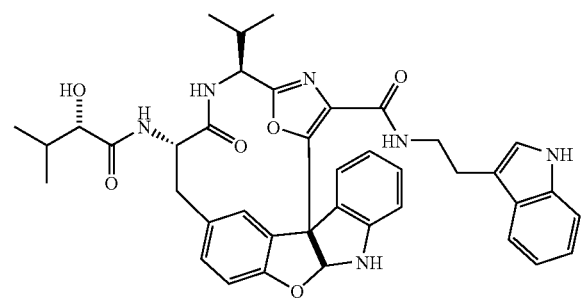

To a dry 15-mL flask containing the amine synthesized in Step B above (0.0184 mmol) were added anhydrous THF (1 mL), N-hydroxysuccinimide ester of (S)-2-hydroxy-3-methylbutyric acid (7.9 mg, 0.0368 mmol, 2 eq.) and $NaHCO_3$ (4.6 mg, 0.0552 mmol, 3 eq.) at RT under $N_2$. The resulting reaction solution was stirred for 20 h. All solvent was evaporated under reduced pressure and the residue was dissolved in EtOAc (30 mL) followed by washing with saturated $NaHCO_3$ (10 mL), water (2×10 mL) and brine (10 mL) and dried over $Na_2SO_4$. The solution was concentrated and the crude was purified by PTLC eluting with $MeOH/CH_2Cl_2$ (7/93) to afford desired product as an off-white solid (3.5 mg, 0.00498 mmol, 27%). MS: m/z=703.2 (M+1).

EXAMPLE 12

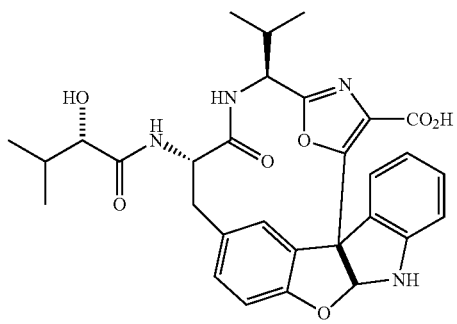

To a 15-mL flask equipped with a magnetic stir bar were added the methyl ester synthesized in Example 6 (7.2 mg, 0.0125 mmol) and methanol (1 mL). The solution was cooled to 0° C. in an ice-water bath followed by addition of LiOH in water (3.0 mg/0.2 mL, 0.125 mmol, 10 eq.) at 0-5° C. with stirring. After addition the reaction mixture became a slurry. The cooling bath was removed and the mixture was allowed to warm to RT. The precipitate disappeared gradually. After 4.5 h stirring at RT less than 2% of SM remained as determined by LCMS. Ice (5 g) was added to the reaction mixture and $HCl/H_2O$ (1 N, 0.13 mL) was added dropwise from a syringe with vigorous stirring to acidify the 0° C. reaction mixture. The pH of the mixture was adjusted to 2.5-3.0. A pale yellow solid precipitated, which was extracted using EtOAc (20 mL). The aqueous phase was concentrated to remove most of methanol and then extracted with EtOAc (2×5 mL). The combined organic layers were washed with brine (20 mL), dried over $Na_2SO_4$ and concentrated to afford the desired product (6 mg, 0.0107 mmol, 86% yield). MS: m/z=561.2 (M+1).

EXAMPLES 13-30

The compounds in Examples 13-30 were prepared using conditions similar to those described in Steps A-C of Example 11. The carboxylic acid synthesized in Example 2 served as the starting material for Examples 13-30, and was used in coupling reactions with a series of amines.

| | | LCMS m/z |
|---|---|---|
| Example 13 | 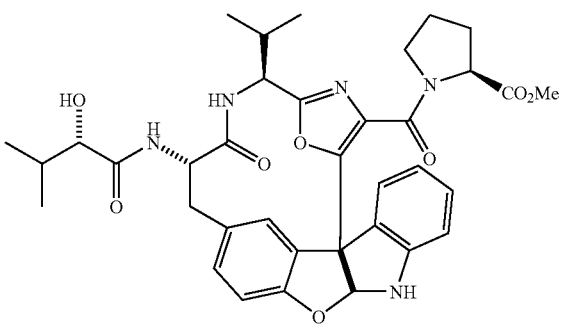 | 672.2 (M + 1) |

|  | LCMS m/z |
|---|---|
| Example 14 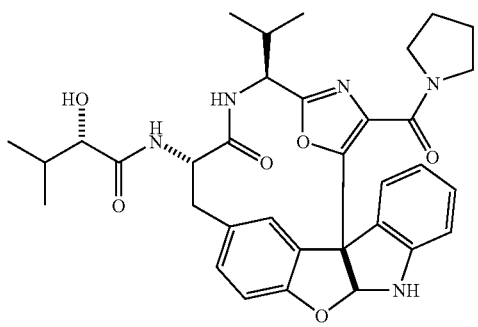 | 614.1 (M + 1) |
| Example 15 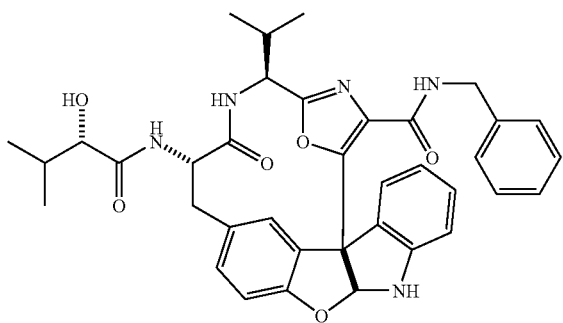 | 650.1 (M + 1) |
| Example 16 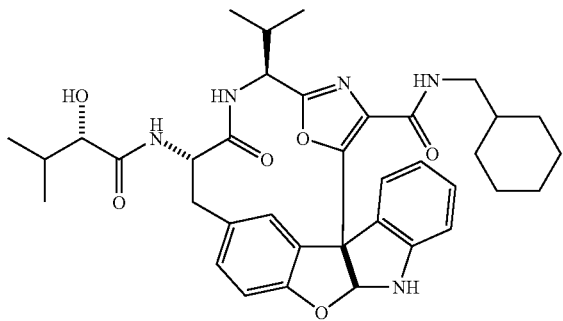 | 656.2 (M + 1) |
| Example 17 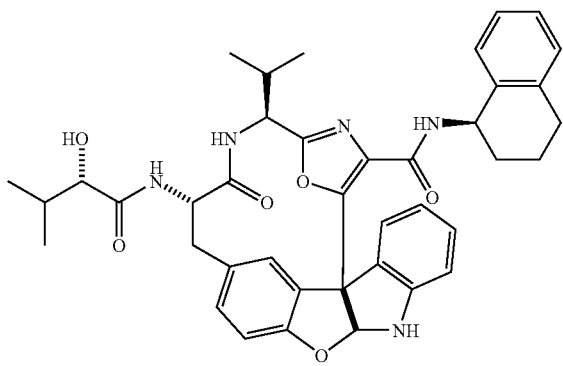 | 690.2 (M + 1) |

|  | LCMS m/z |
|---|---|
| Example 18 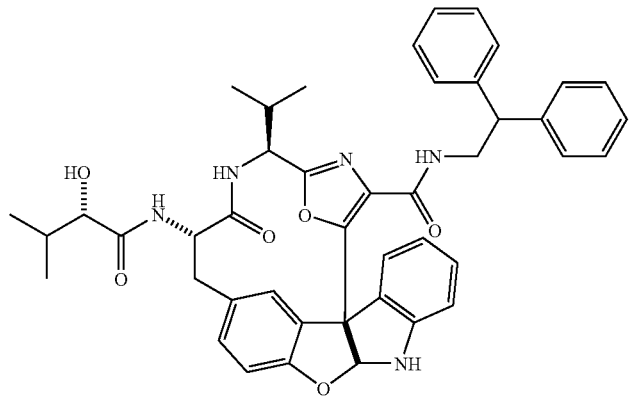 | 740.1 (M + 1) |
| Example 19 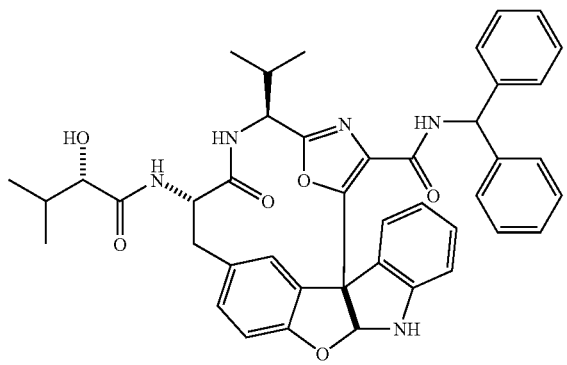 | 726.2 (M + 1) |
| Example 20 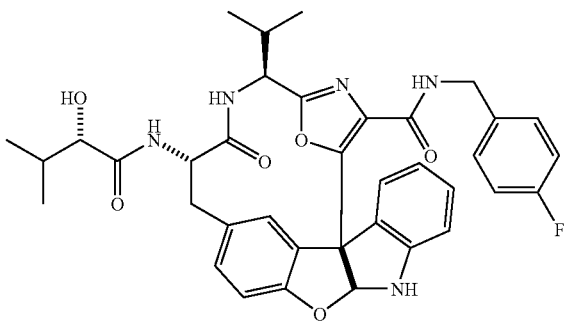 | 668.1 (M + 1) |
| Example 21 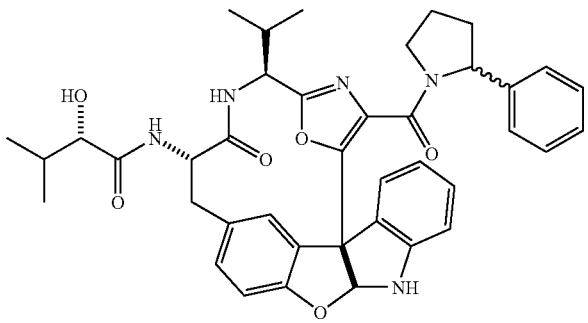 | 690.2 (M + 1) |

|  | | LCMS m/z |
|---|---|---|
| Example 22 | 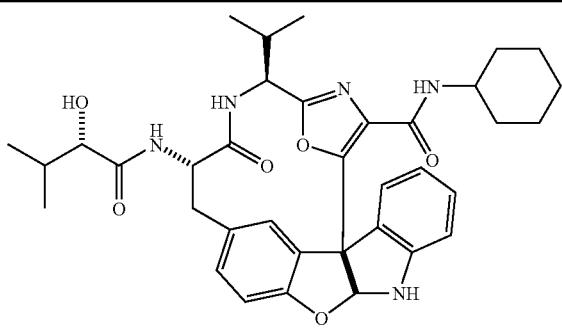 | 642.2 (M + 1) |
| Example 23 | 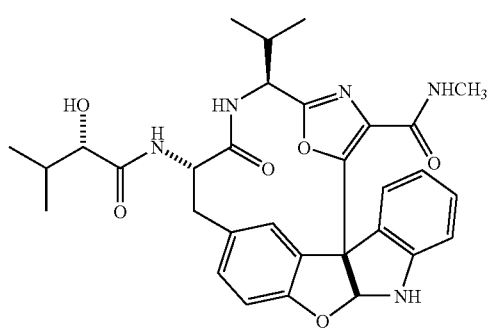 | 574.0 (M + 1) |
| Example 24 | 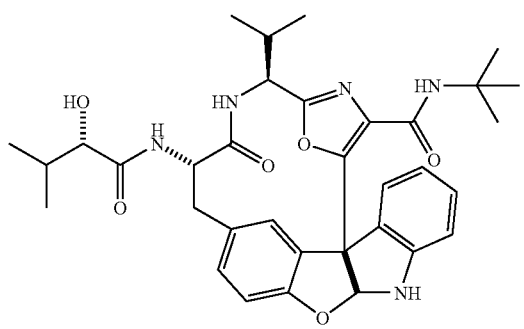 | 616.2 (M + 1) |
| Example 25 | 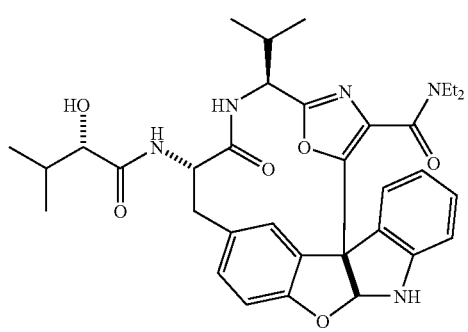 | 616.2 (M + 1) |

|  | LCMS m/z |
|---|---|
| Example 26 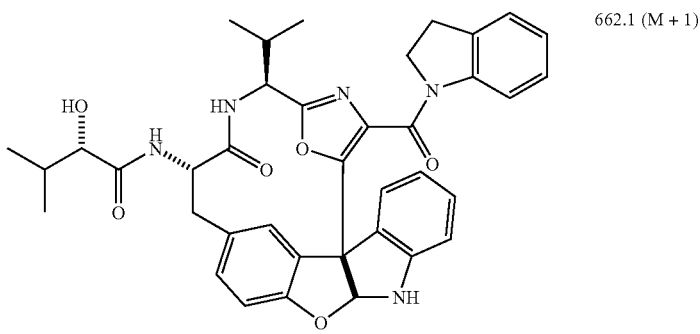 | 662.1 (M + 1) |
| Example 27 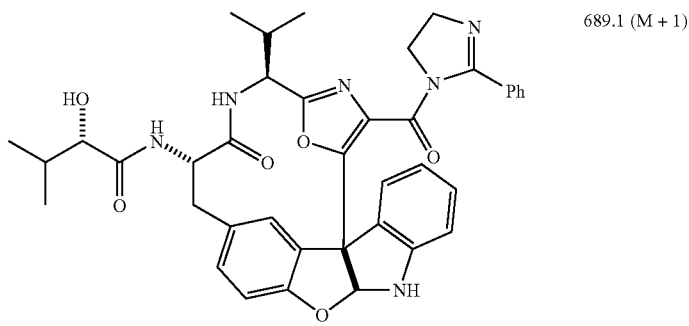 | 689.1 (M + 1) |
| Example 28 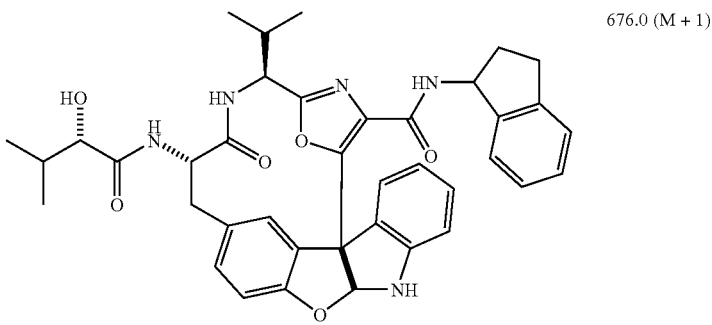 | 676.0 (M + 1) |
| Example 29 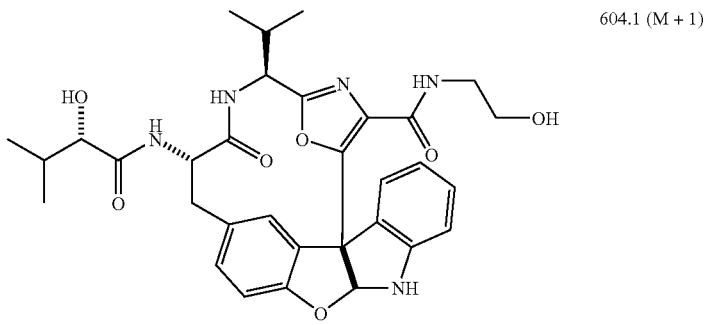 | 604.1 (M + 1) |

| | LCMS m/z |
|---|---|
| Example 30 | 662.0 (M + 1) |

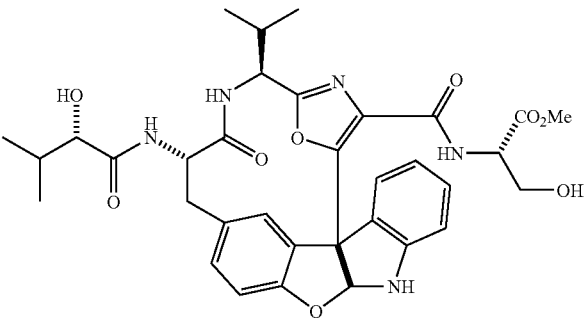

EXAMPLE 31

Step A:

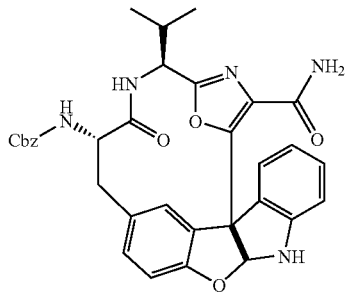

To a dry 15-mL flask were added carboxylic acid synthesized in Example 5 (11 mg, 0.0185 mmol), anhydrous CH$_2$Cl$_2$ (2 mL) and anhydrous THF (0.1 mL). The reaction solution was cooled to 0° C. in ice-water bath. N,N-Diisopropylethylamine (0.0032 mL, 0.0185 mmol, 1 eq.) and isobutyl chloroformate (0.0024 mL, 0.0185 mmol, 1.0 eq.) were added with stirring. The mixture was stirred at 0° C. under N$_2$ for 20 min. followed by addition of a solution of ammonia in 1,4-dioxane (0.5 M, 0.185 mL, 0.0925 mmol, 5 eq.). Then the resulting reaction solution was stirred at 0° C. for another 1 h and at RT overnight. The reaction mixture was diluted with EtOAc (30 mL), washed with water (2×10 mL), brine (2×10 mL), and dried over Na$_2$SO$_4$. After concentration the crude product was purified by PTLC eluting with MeOH/CH$_2$Cl$_2$ (10/90) to afford desired product as an off-white solid (6 mg, 0.0101mmol, 55%). MS: m/z=594.0 (M+1).

Step B:

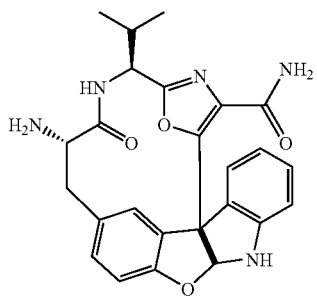

The conditions for this reaction are similar to those used for Step B of Example 11. The compound synthesized in Step A above served as the starting material. The crude was used directly in next step without further purification.

Step C:

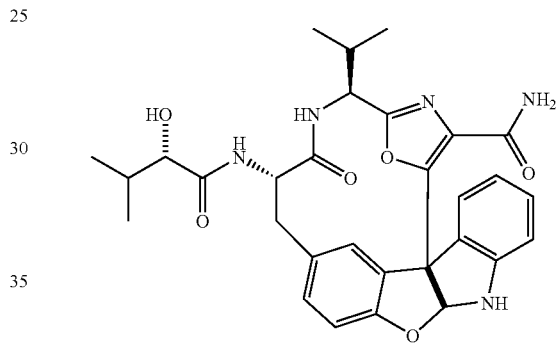

The conditions for this reaction are similar to those used for Step C of Example 11. The compound synthesized in Step B above served as the starting material. MS: m/z=560.1 (M+1).

EXAMPLE 32

Step A:

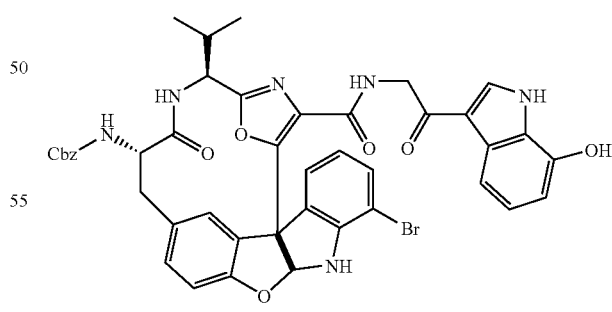

DMF (7 mL) was added to the carboxylic acid synthesized in Example 2 (157 mg, 0.23 mmol, ca. 96% pure), HOBt (38 mg, 0.28 mmol, 1.2 eq.), and 2-amino-1-(7-hydroxy-1H-indol-3-yl)ethanone hydrochloride (66 mg, 0.28 mmol, 1.2 eq.) in a round-bottom flask. N,N-Diisopropylethylamine (0.051 mL, 37 mg, 0.29 mmol, 1.25 eq.) was added, followed by EDC (49 mg, 0.26 mmol, 1.1 eq.). After stirring for 12 h at 25°

C., most of the DMF was removed under vacuum. The residue was dissolved in EtOAc (100 mL) and washed with 1 N aqueous HCl (50 mL), saturated aqueous NaHCO$_3$ (50 mL), and saturated aqueous sodium chloride (50 mL). The solution was dried (Na$_2$SO$_4$). After concentration the crude product (186 mg, 0.22 mmol, 94%) was obtained and used directly in next step without further purification. MS: m/z=845.1 (M+1).

Step B:

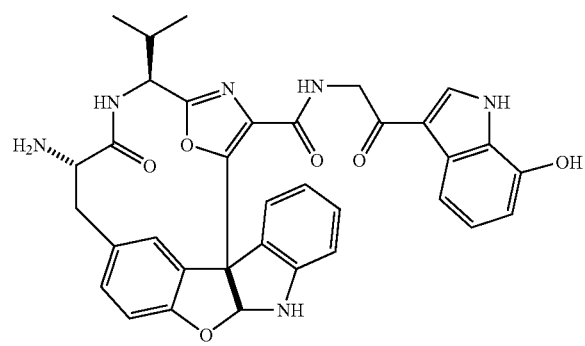

The conditions for this reaction are similar to those used for Example 3. The compound synthesized in Step A above served as the starting material. MS: m/z=633.2 (M+1).

Step C:

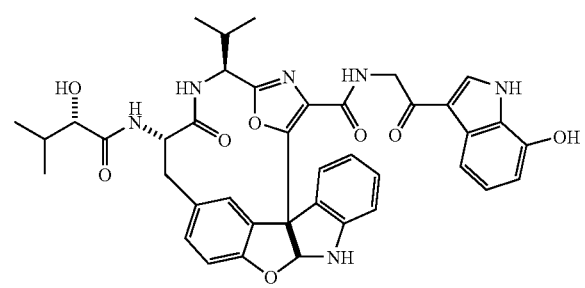

The coupling conditions for this reaction are similar to those described in Example 7. The compound synthesized in Step B above served as the amine reactant, and (S)-2-hydroxy-3-methylbutyric acid was used in place of (S)-mandelic acid. MS: m/z=733.0 (M+1).

EXAMPLE 33

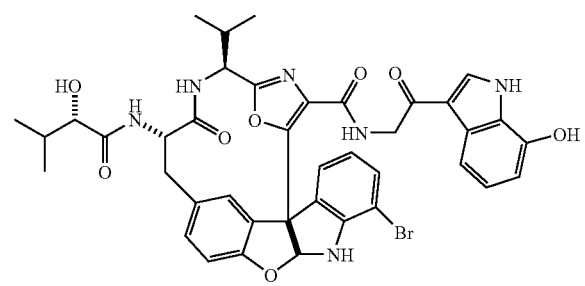

This compound was isolated as a by-product from Step C of Example 32. MS: m/z=811.0 (M+1).

EXAMPLE 34

Step A:

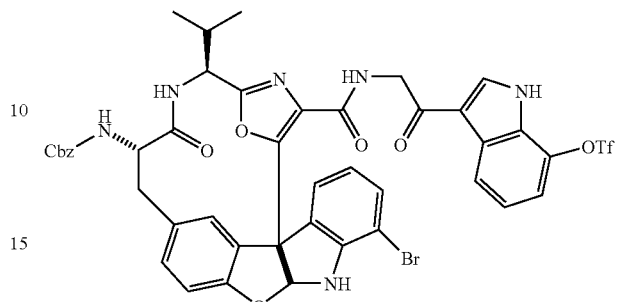

The conditions for this reaction are similar to those used for Step A of Example 91. The compound synthesized in Step A of Example 32 served as the starting material.

Step B:

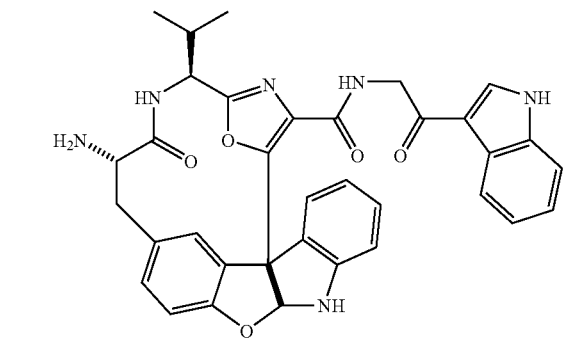

The conditions for this reaction are similar to those used for Step B of Example 91. The compound synthesized in Step A above served as the starting material. MS: m/z=617.1 (M+1).

Step C:

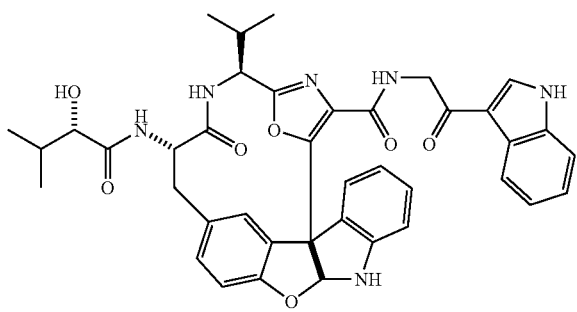

The coupling conditions for this reaction are similar to those described in Example 7. The compound synthesized in Step B above was served as the amine reactant, and (S)-2-hydroxy-3-methylbutyric acid was used in place of (S)-mandelic acid. MS: m/z=717.2 (M+1).

EXAMPLE 35

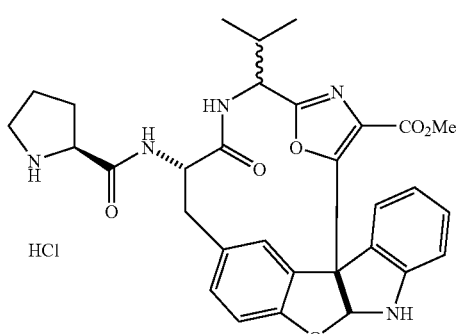

HCl

The product of Example 35 was prepared by reaction of the amine from Example 3 using coupling conditions similar to those described for Example 7. Boc-L-proline was used in place of (S)-mandelic acid. After isolation of the coupling product, the Boc protecting group was removed by treatment with 4 M HCl in 1,4-dioxane. MS: m/z=572.1 (M+1).

EXAMPLE 36

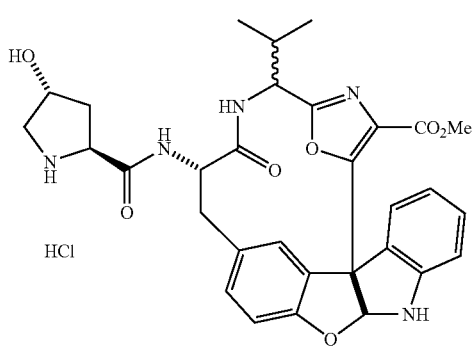

HCl

The product of Example 36 was prepared by reaction of the amine from Example 3 using coupling conditions similar to those described for Example 7. trans-Boc-4-hydroxy-L-proline was used in place of (S)-mandelic acid. After isolation of the coupling product, the Boc protecting group was removed by treatment with 4 M HCl in 1,4-dioxane. MS: m/z=588.2 (M+1).

EXAMPLE 37

Step A:

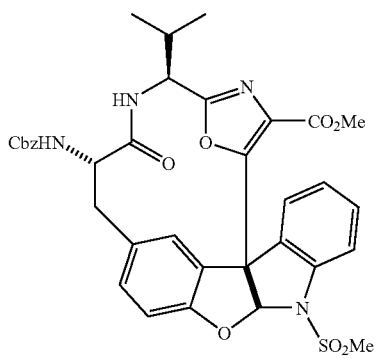

To a dry 15-mL flask were added the material synthesized in Example 4 (55 mg, 0.0904 mmol) and anhydrous $CH_2Cl_2$ (1 mL). The reaction solution was cooled to 0° C. in ice-water bath. Triethylamine (0.057 mL, 0.409 mmol, 4.5 eq.) and a stock solution of methanesulfonyl chloride (0.023 mL, 0.296 mmol, 3.3 eq.) in $CH_2Cl_2$ (0.3 mL) were added. The reaction mixture was allowed to warm to RT and was stirred for 2 h. The reaction mixture was diluted with EtOAc (30 mL), washed with water (2×10 mL), brine (2×10 mL), and dried over $Na_2SO_4$. After concentration the crude product was used in next step without further purification.

Step B:

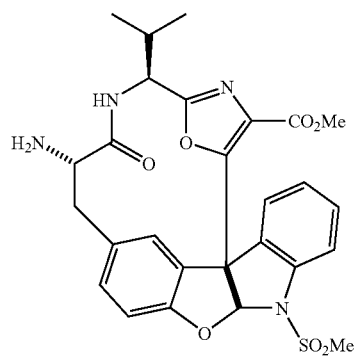

The conditions for this reaction are similar to those used for Step B of Example 11. The compound synthesized in Step A above served as the starting material. The crude product was used directly in the next step without further purification.

Step C:

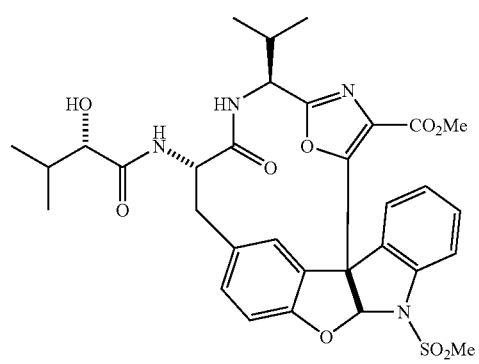

The conditions for this reaction are similar to those used for Step C of Example 11. The compound synthesized in Step B above served as the starting material. MS: m/z=653.1 (M+1).

EXAMPLE 38

Step A:

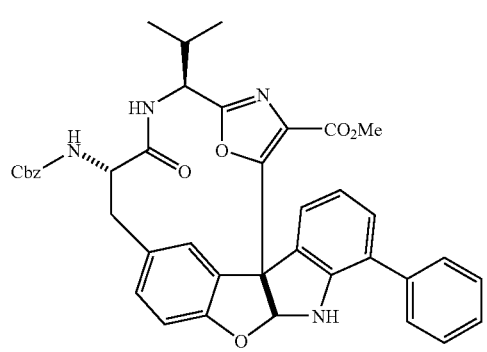

To a 15-mL flask were added the compound synthesized in Step G of Example 1 (25 mg, 0.0364 mmol), phenylboronic acid pinacol ester (8.9 mg, 0.0437 mmol, 1.2 eq.), $K_3PO_4$ (23 mg, 0.109 mmol, 3 eq.), and $Pd(PPh_3)_4$ (4.2 mg, 0.00364 mmol, 0.1 eq.). The mixture was degassed by passing nitrogen flow for 20 min. followed by the addition of pre-degassed dioxane/water (5/1, 3 mL). The resulting reaction mixture was heated to 70° C. and stirred under $N_2$ for 5 h. The reaction was stopped. The reaction mixture was diluted with EtOAc (30 mL), washed with water (3×10 mL), and dried over $Na_2SO_4$. After concentration the crude product was purified by PTLC eluting with EtOAc/toluene (40/60) to afford desired product as an off-white solid (6 mg, 0.00876 mmol, 24%). MS: m/z 685.0 (M+1).

Step B:

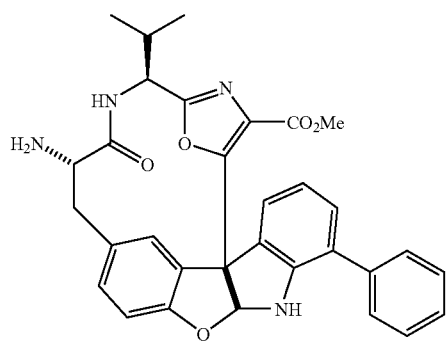

The conditions for this reaction are similar to those used for Step B of Example 11. The compound synthesized in Step A above served as the starting material. The crude product was used directly in the next step without purification.

Step C:

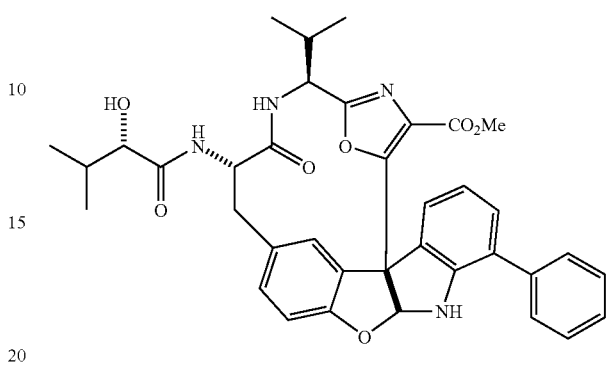

The conditions for this reaction are similar to those used for Step C of Example 11. The compound synthesized in Step B above served as the starting material. MS: m/z=651.2 (M+1).

EXAMPLES 39-42

The compounds in Examples 39-42 were prepared using conditions similar to those described in Steps A-C of Example 38. The carboxylic acid synthesized in Step G of Example 1 served as the starting material for Examples 39-42, with four different aromatic boronic acids used in Step A.

| | | LCMS m/z |
|---|---|---|
| Example 39 | 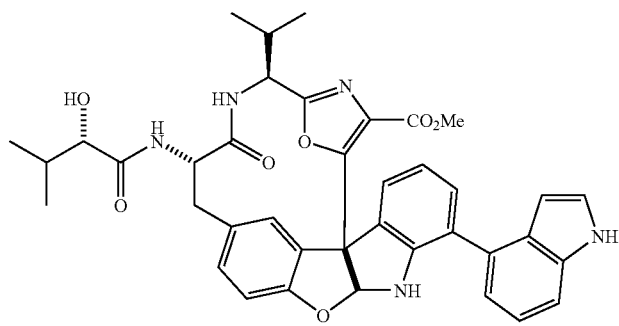 | 690.2 (M + 1) |
| Example 40 | 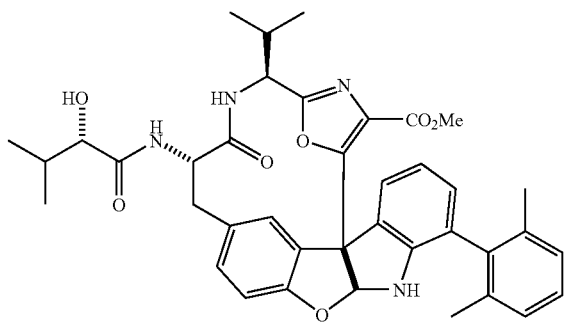 | 679.2 (M + 1) |

|            |                  | LCMS m/z     |
|------------|------------------|--------------|
| Example 41 | 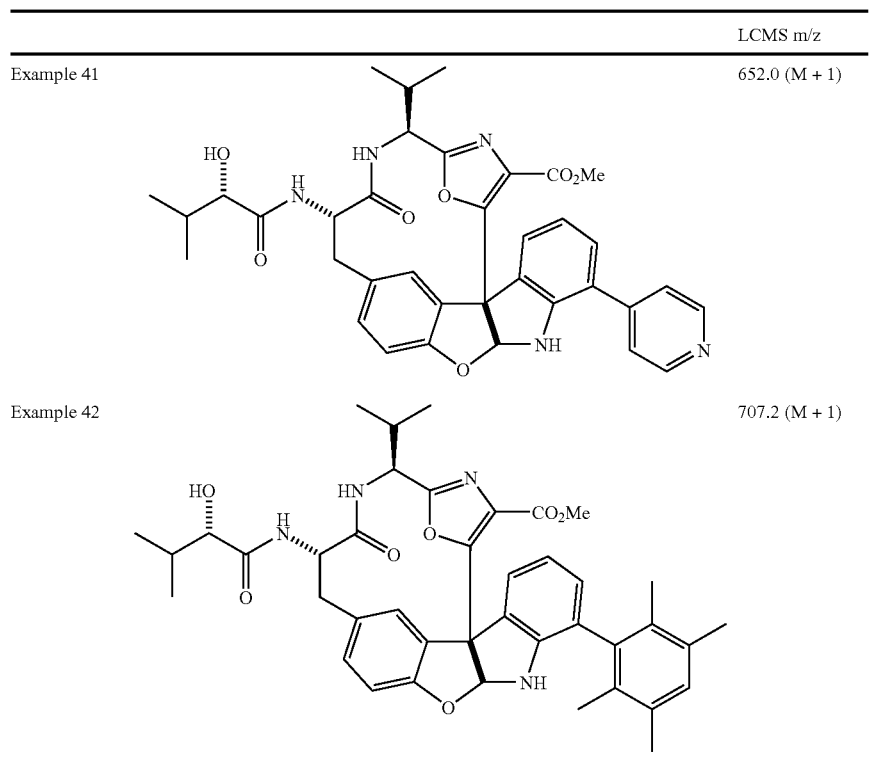 | 652.0 (M + 1) |
| Example 42 |                  | 707.2 (M + 1) |

EXAMPLE 43

Step A:

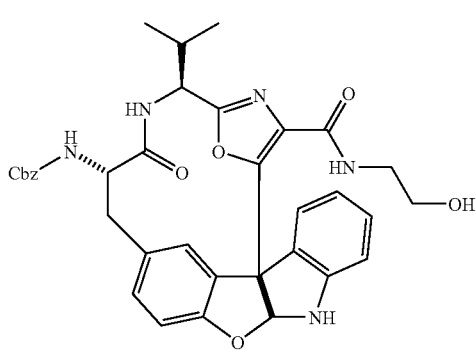

To a dry 15-mL flask with magnetic stir bar was added the carboxylic acid synthesized in Example 5 (50 mg, 0.0841 mmol), ethanolamine hydrochloride (9.0 mg, 0.0925 mmol, 1.1 eq.), HOBt (12.5 mg, 0.0925 mmol, 1.1 eq.), anhydrous DMF (2 mL) and N,N-diisopropylethylamine (0.032 mL, 0.185 mmol, 2.2 eq.). The reaction mixture was cooled to 0° C. followed by addition of EDC (17.7 mg, 0.0925 mmol, 1.1 eq.). The resulting reaction mixture was stirred at RT for 16 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous $NaHSO_4$ (20 mL), water (20 mL), saturated $NaHCO_3$ (20 mL), and brine (2×20 mL), and then dried over $Na_2SO_4$. After concentration, the crude was used directly in the next step. MS: m/z=638.1 (M+1).

Step B:

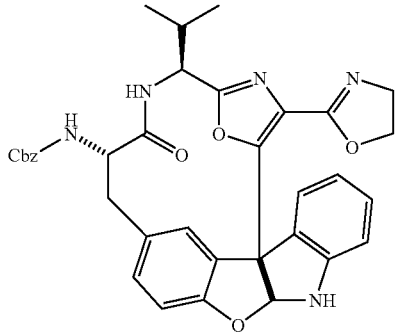

To a dry flask were added the crude product from Step A above (13 mg, 0.020 mmol) and anhydrous $CH_2Cl_2$ (0.9 mL). The reaction solution became cloudy as it was cooled to −78° C. in a dry ice/acetone bath. A freshly made stock solution of (diethylamino)sulfur trifluoride (0.0074 mL, 0.022 mmol, 2.8 eq.) in $CH_2Cl_2$ (0.25 mL) was added dropwise. The resulting reaction mixture was stirred at −78° C. for 1 h, and warmed to RT overnight. The reaction mixture was quenched by addition of saturated aqueous $NaHCO_3$ (3 mL), diluted with EtOAc (20 mL), washed with water (2×10 mL) as well as brine (10 mL), and dried over $Na_2SO_4$. After concentration the residue was purified by PTLC eluting with $MeOH/CH_2Cl_2$ (10/90) to afford the desired product as an off-white solid (4 mg, 0.00646 mmol, 32%). MS: m/z=620.1 (M+1).

Step C:

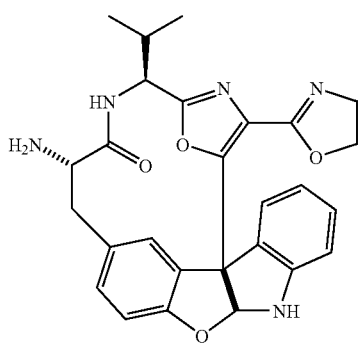

The conditions for this reaction are similar to those used for Step B of Example 11. The oxazoline synthesized in Step B above served as the starting material. The crude product was used directly in the next step without purification.

Step D:

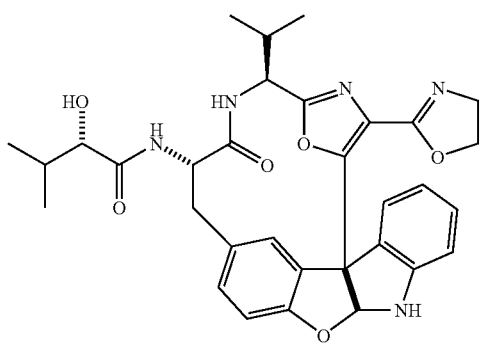

The conditions for this reaction are similar to those used for Step C of Example 11. The amine synthesized in Step C above served as the starting material. MS: m/z=586.0 (M+1).

EXAMPLE 44

Step A:

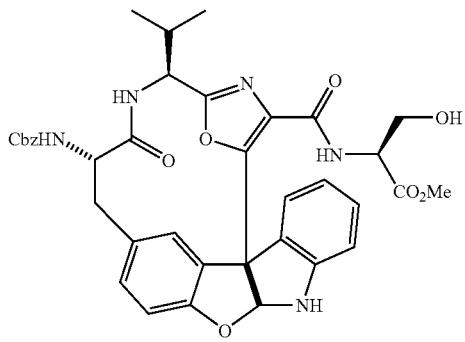

To a dry 15-mL flask with magnetic stir bar were added the material synthesized in Example 5 (50 mg, 0.0841 mmol), L-serine methyl ester hydrochloride (14.4 mg, 0.0925 mmol, 1.1 eq.), HOBt (12.5 mg, 0.0925, 1.1 eq.), anhydrous DMF (2 mL) and N,N-diisopropylethylamine (0.032 mL, 0.185 mmol, 2.2 eq.). The reaction mixture was cooled to 0° C. followed by addition of EDC (17.7 mg, 0.0925 mmol, 1.1 eq.). The resulting reaction mixture was stirred at RT for 18 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous NaHSO$_4$ (20 mL), water (20 mL), saturated NaHCO$_3$ (20 mL), and brine (2×20 mL), and then dried over Na$_2$SO$_4$. After concentration the crude product was used in next step without further purification. MS: m/z=696.2 (M+1).

Step B:

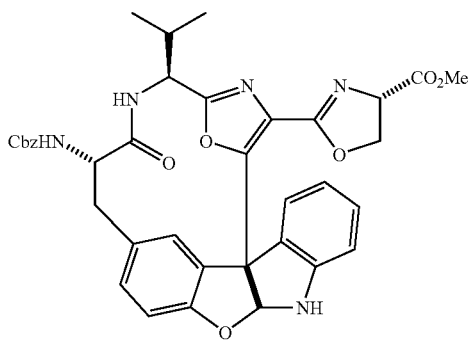

The conditions for this reaction are similar to those used for Step B of Example 43. The amide synthesized in Step A above served as the starting material.

Step C:

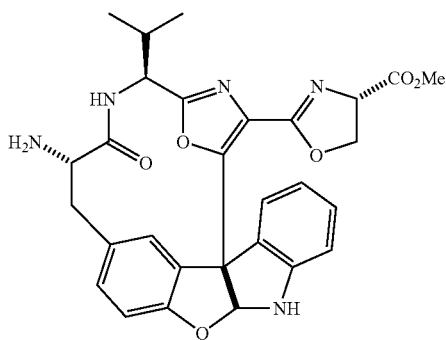

The conditions for this reaction are similar to those used for Step B of Example 11. The oxazoline synthesized in Step B above served as the starting material.

Step D:

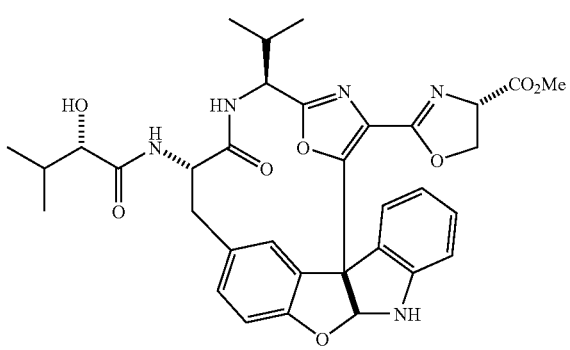

The conditions for this reaction are similar to those used for Step C of Example 11. The amine synthesized in Step C above served as the starting material. MS: m/z=644.1 (M+1).

EXAMPLE 45

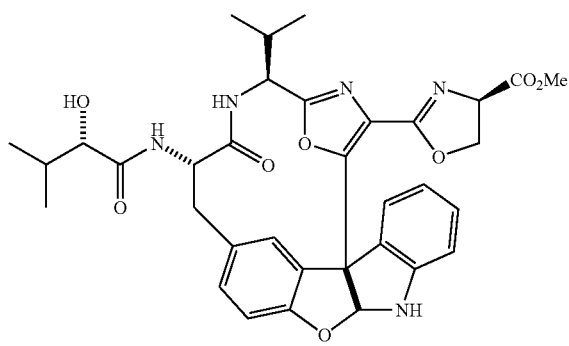

The conditions for this synthesis are similar to those used for Steps A-D of Example 44. The material synthesized in Example 5 and D-serine methyl ester hydrochloride served as the starting materials. MS: m/z=644.2 (M+1).

EXAMPLE 46

Step A:

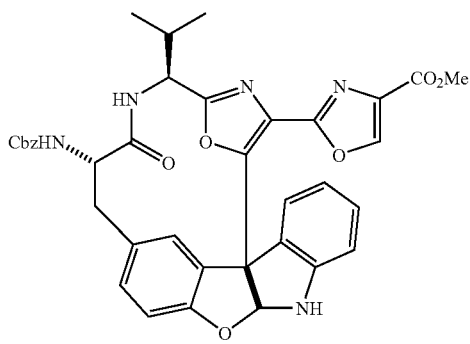

To a dry flask were added the compound synthesized in Step A of Example 44 (14 mg, 0.020 mmol) and anhydrous CH$_2$Cl$_2$ (0.9 mL). The reaction solution was cooled to −78° C. in dry ice/acetone bath and turned cloudy. A freshly made stock solution of (diethylamino)sulfur trifluoride (0.0079 mL, 0.060 mmol, 3.0 eq.) in CH$_2$Cl$_2$ (0.10 mL) was added dropwise. The resulting reaction mixture was stirred at −78° C. for 1 h, and warmed to RT for 10 min. The mixture was cooled back to −78° C., and DBU (0.015 mL, 0.1 mmol, 5 eq.) and CBrCl$_3$ (0.010 mL, 0.1 mmol, 5 eq.) were added. The resulting mixture was allowed to warm to RT slowly overnight. The reaction mixture was quenched by addition of saturated aqueous NaHCO$_3$ (3 mL), diluted with EtOAc (20 mL), washed with water (2×10 mL) as well as brine (10 mL), dried over Na$_2$SO$_4$. After concentration the residue was purified by PTLC eluting with MeOH/CH$_2$Cl$_2$ (10/90) to afford desired product as an off-white solid (5 mg, 0.0074 mmol, 37%). MS: m/z=676.0 (M+1).

Step B:

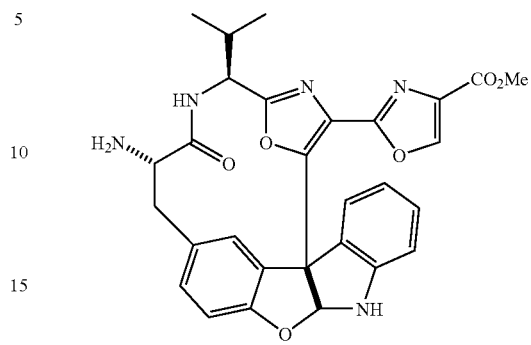

The conditions for this reaction are similar to those used for Step B of Example 11. The oxazole synthesized in Step A above served as the starting material. The crude product was used directly in the next step without purification.

Step C:

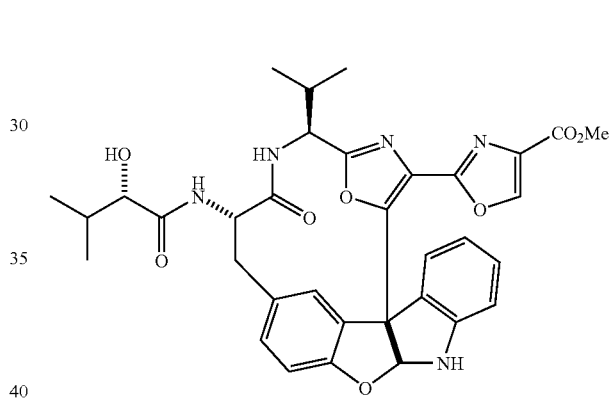

To a dry 15-mL flask containing the amine synthesized in Step B above (0.0074 mmol) were added anhydrous THF (1.5 mL), N-hydroxysuccinimide ester of (S)-2-hydroxy-3-methylbutyric acid (3.2 mg, 0.0148 mmol, 2 eq.) and NaHCO$_3$ (1.9 mg, 0.0222 mmol, 3 eq.) at RT under N$_2$. The resulting reaction solution was stirred for 20 h. All solvent was evaporated under reduced pressure and the residue was dissolved in EtOAc (30 mL). The solution was washed with saturated NaHCO$_3$ (10 mL), water (2×10 mL) and brine (10 mL) and dried over Na$_2$SO$_4$. The solution was concentrated and the crude was purified by PTLC eluting with MeOH/CH$_2$Cl$_2$ (10/90) to afford desired product as an off-white solid (2.0 mg, 0.00311 mmol, 42%). MS: m/z=642.2 (M+1).

EXAMPLES 47-53

The compounds in Examples 47-53 were prepared using coupling conditions similar to those used in Example 7. The amine synthesized in Step B of Example 46 served as the starting material. Coupling of this amine with a series of carboxylic acids produced the amide derivatives.

|  | LCMS m/z |
|---|---|
| Example 47 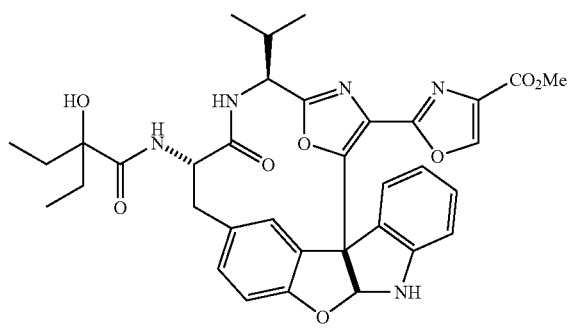 | 656.1 (M + 1) |
| Example 48 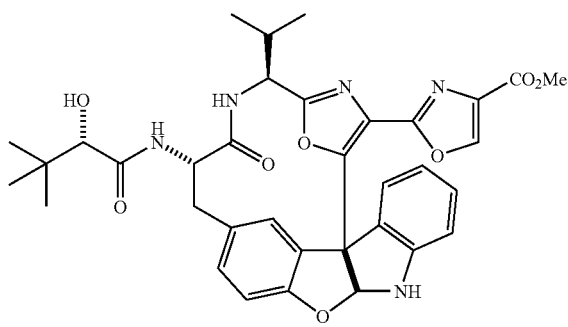 | 656.1 (M + 1) |
| Example 49 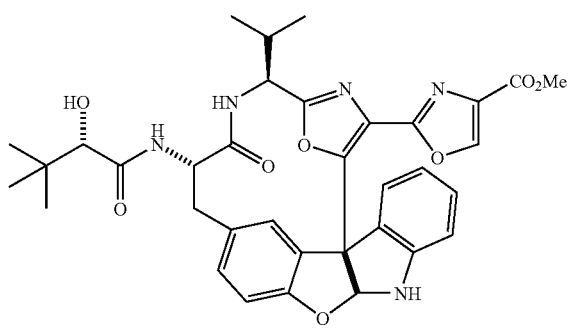 | 656.1 (M + 1) |
| Example 50 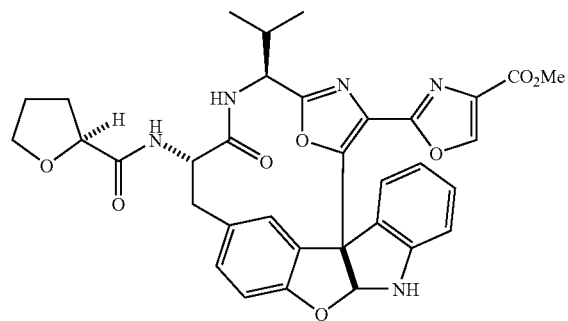 | 640.0 (M + 1) |

| | LCMS m/z |
|---|---|
| Example 51 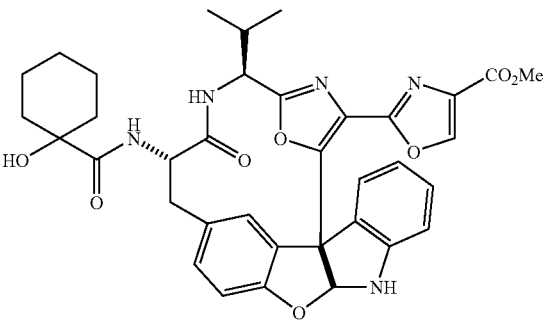 | 668.1 (M + 1) |
| Example 52 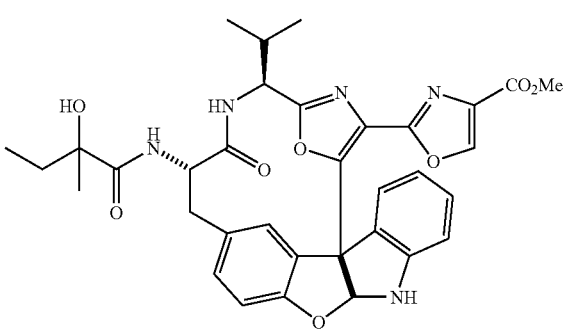 | 642.2 (M + 1) |
| Example 53 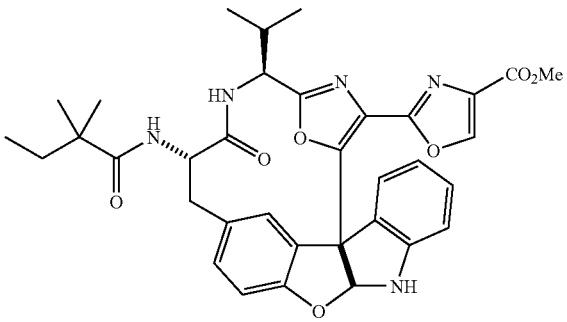 | 640.0 (M + 1) |

EXAMPLE 54

Step A:

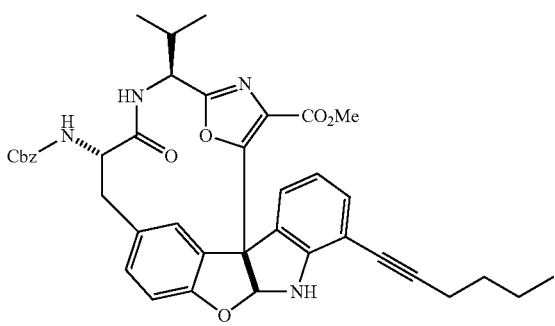

To a dry 15-mL flask were added the material synthesized in Step G of Example 1 (45 mg, 0.0655 mmol), Pd(Ph$_3$P)$_2$Cl$_2$ (2.3 mg, 0.00328 mmol, 0.05 eq.), CuI (0.6 mg, 0.0032 mmol, 0.05 eq.), pre-degassed DMF (2 mL) and TEA (0.091 mL, 0.653 mmol, 10 eq.). The reaction mixture was passed N$_2$ flow for 30 min. Then 1-hexyne (0.036 mL, 0.32 mmol, 4.9 eq.) was added. The resulting reaction mixture was stirred at RT for 18 h. The reaction was stopped and the mixture was filtered through a pad of Celite. The filtrate was diluted with EtOAc (30 mL), washed with water (2×10 mL), brine (2×10 mL), and dried over Na$_2$SO$_4$. After concentration the crude product was purified by PTLC eluting with MeOH/CH$_2$Cl$_2$ (6/94) to afford desired product as an off-white solid (7 mg, 0.0101 mmol, 15%). MS: m/z=689.3 (M+1).

Step B:

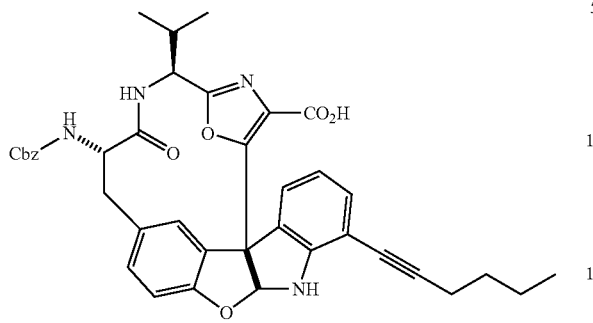

The conditions for this reaction are similar to those used for Example 12. The material synthesized in Step A above served as the starting material. MS: m/z=675.3 (M+1).

Step C:

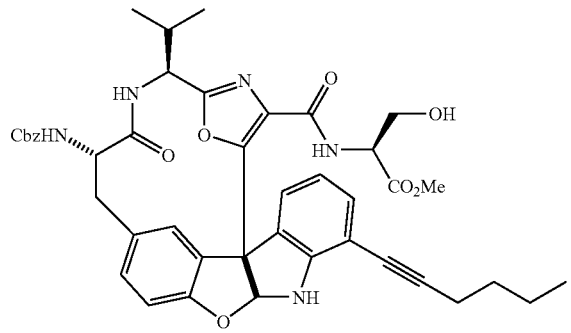

The conditions for this reaction are similar to those used for Step A of Example 44. The material synthesized in Step B above served as the starting material. MS: m/z=776.2 (M+1).

Step D:

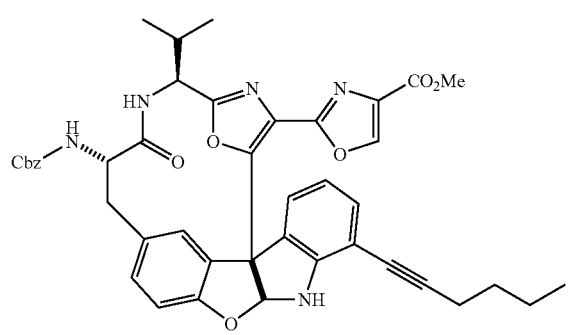

The conditions for this reaction are similar to those used for Step A of Example 46. The material synthesized in Step C above served as the starting material. MS: m/z=756.3 (M+1).

Step E:

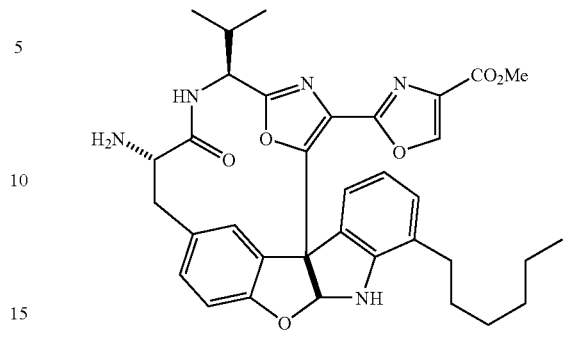

The conditions for this reaction are similar to those used for Step B of Example 11. The material synthesized in Step D above served as the starting material. The crude product was used directly in the next step without further purification.

Step F:

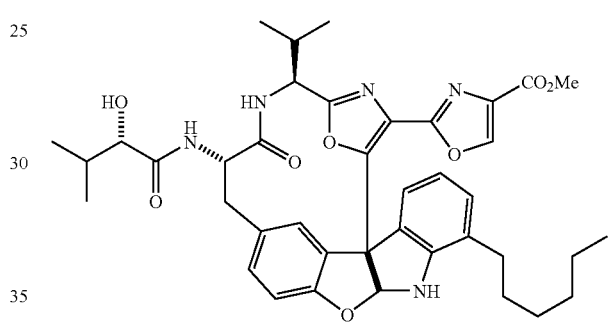

The conditions for this reaction are similar to those used for Step C of Example 11. The material synthesized in Step E above served as the starting material. MS: m/z=726.3 (M+1).

EXAMPLE 55

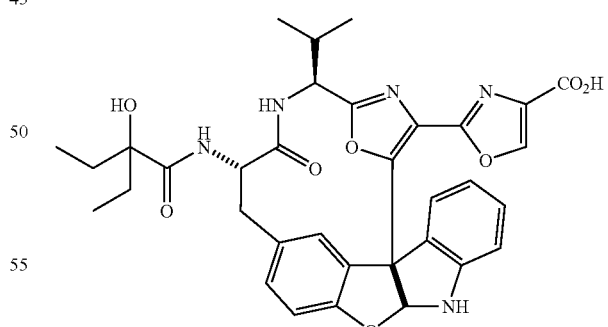

To a 15-mL flask equipped with a magnetic stir bar was added the methyl ester synthesized in Example 47 (14 mg, 0.0213 mmol) and methanol (1.4 mL). The solution was cooled to 0° C. in an ice-water bath followed by addition of LiOH in water (5.1 mg/0.3 mL, 0.213 mmol, 10 eq.) at 0-5° C. with stirring. After addition the reaction mixture became a slurry. The cooling bath was removed and the mixture was allowed to warm to RT. The precipitate disappeared gradually. After 18 h stirring at RT less than 2% of SM remained as determined by LCMS. Ice (10 g) was added to the reaction mixture and HCl/H$_2$O (1 N, 0.218 mL) was added dropwise from a syringe with vigorous stirring to acidify the 0° C. reaction mixture. The pH of the mixture was adjusted to 2.5-3.0. An off-white solid precipitated, which was extracted using EtOAc (20 mL). The aqueous phase was concentrated to remove most of methanol and then extracted with EtOAc (2×5 mL). The combined organic layers were washed with brine (20 mL) and dried over Na$_2$SO$_4$ and concentrated to afford desired product (13 mg, 0.0203 mmol, 95% yield). MS: m/z=642.0 (M+1).

EXAMPLE 56

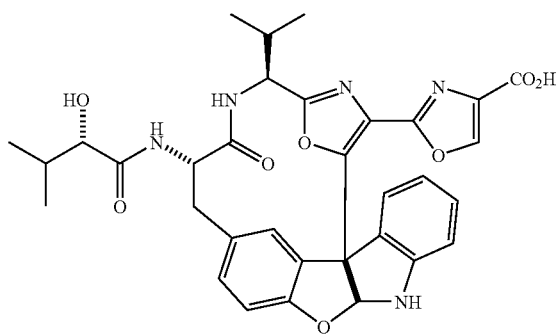

The conditions for this reaction are similar to those used for Example 55. The methyl ester synthesized in Step C of Example 46 served as the starting material. MS: m/z=628.0 (M+1).

EXAMPLE 57

Step A:

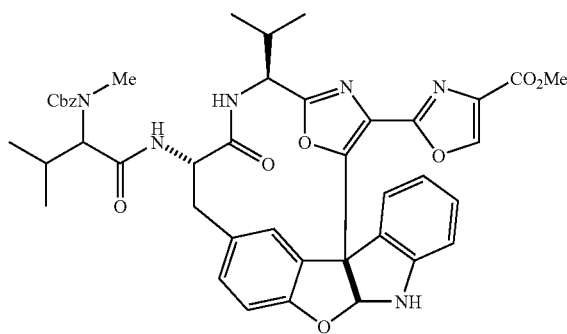

To a dry 15-mL flask with magnetic stir bar was added the amine synthesized in Step B of Example 46 (5 mg, 0.00932 mmol), Cbz-(N-Me-L-Val)-OH (3.7 mg, 0.0138 mmol, 1.5 eq.), a stock solution of HOBt (1.86 mg, 0.0138 mmol, 1.5 eq.) in DMF (0.050 mL), anhydrous DMF (0.8 mL) and a stock solution of N,N-diisopropylethylamine (0.0032 mL, 0.0185 mmol, 2.0 eq.) in DMF (0.050 mL). The reaction mixture was cooled to 0° C. followed by addition of a stock solution of EDC in DMF (2.65 mg, 0.0138, 1.5 eq.). The resulting reaction mixture was stirred at RT for 18 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous NaHSO$_4$ (20 mL), water (20 mL), saturated aqueous NaHCO$_3$ (20 mL), and brine (2×20 mL), and then dried over Na$_2$SO$_4$. After concentration the crude product was purified by PTLC eluting with MeOH/CH$_2$Cl$_2$ (7/93) to afford desired product as an off-white solid (3.5 mg, 0.0044 mmol, 48%). MS: m/z=789.2 (M+1).

Step B:

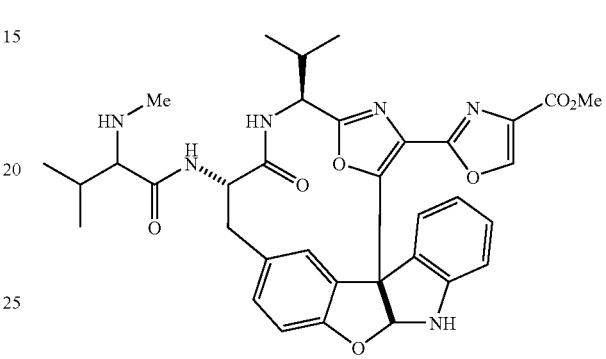

To a 15-mL flask containing material synthesized in Step A above (3.5 mg, 0.0044 mmol) was added methanol (2 mL) and 10% Pd/C (1.4 mg, 0.0013 mmol) under N$_2$. H$_2$ balloon was added and the flask was purged with H$_2$ for 4 times. Then H$_2$ balloon was opened to the reaction system. After 5 h stirring almost no starting material remained. The reaction was stopped. The reaction mixture was filtered through a pad of Celite and the black cake was washed with methanol (3×1 mL). The filtrate was concentrated to afford desired product as off-white solid (2.8 mg, 0.0043 mmol, 96%). MS: m/z=655.2 (M+1).

EXAMPLE 58

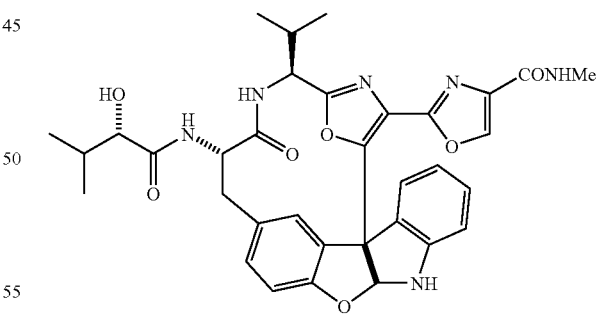

To a dry 15-mL flask with magnetic stir bar was added the material synthesized in Example 56 (3.0 mg, 0.00478 mmol), anhydrous DMF (1 mL), a stock solution of methylamine hydrochloride (0.48 mg, 0.0072 mmol, 1.5 eq.) in DMF (0.050 mL), a stock solution of HOBt (0.97 mg, 0.0072 mmol, 1.5 eq.) in DMF (0.050 mL), and a stock solution of N,N-diisopropylethylamine (0.0021 mL, 0.012 mmol, 2.5 eq.) in DMF (0.050 mL). The reaction mixture was cooled to 0° C. followed by addition of a stock solution of EDC (1.4 mg, 0.0072, 1.5 eq.) in DMF (0.100 mL). The resulting reaction mixture was stirred at room temperature for 18 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous $NaHSO_4$ (20 mL), water (20 mL), saturated $NaHCO_3$ (20 mL), and brine (2×20 mL), and then dried over $Na_2SO_4$. After concentration the crude product was purified by PTLC eluting with $MeOH/CH_2Cl_2$ (12/88) to afford desired product as an off-white solid (2.1 mg, 0.00328 mmol, 69%). MS: m/z=641.1 (M+1).

EXAMPLES 59-65

The oxazole ester synthesized in Step A of Example 46 served as the starting material for Examples 59-65. This material was converted to the oxazole acid using conditions similar to those described in Example 55. Using conditions similar to those described in Steps A-C of Example 11, this carboxylic acid was then used in coupling reactions with a series of amines, removal of the Cbz group, and coupling of the resulting amine with (S)-2-hydroxy-3-methylbutanoic acid.

|  |  | LCMS m/z |
|---|---|---|
| Example 59 | | 683.1 (M + 1) |
| Example 60 | | 681.2 (M + 1) |
| Example 61 | | 703.2 (M + 1) |

|  | | LCMS m/z |
|---|---|---|
| Example 62 | 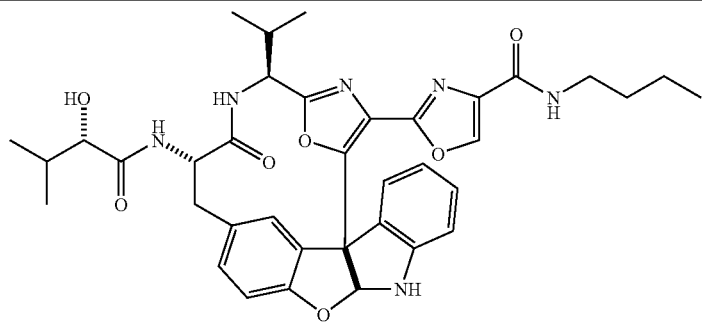 | 683.1 (M + 1) |
| Example 63 | 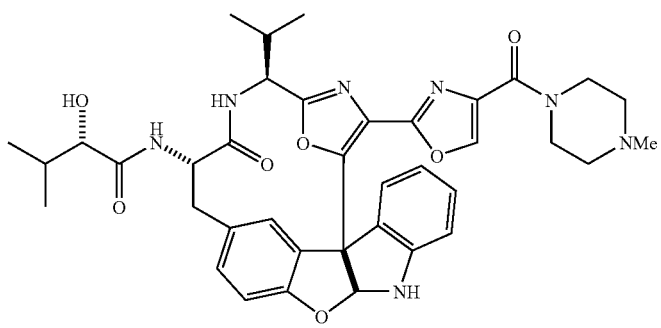 | 710.1 (M + 1) |
| Example 64 | 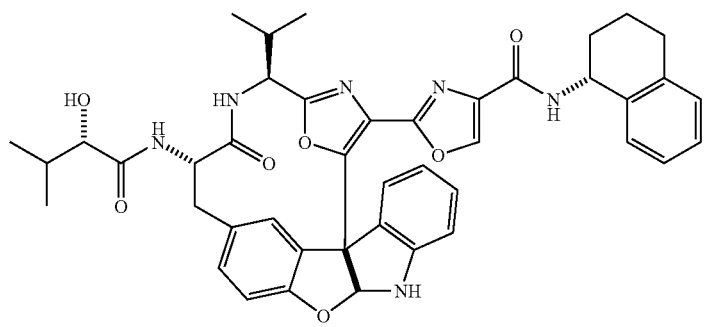 | 757.2 (M + 1) |
| Example 65 | 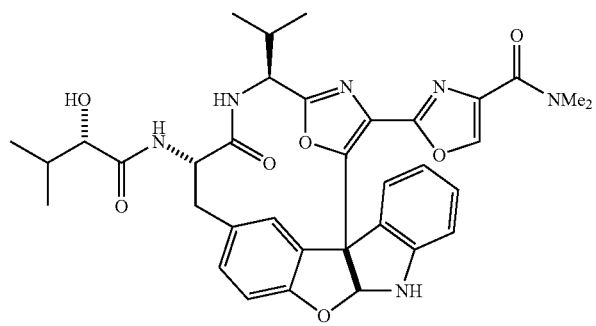 | 655.2 (M + 1) |

EXAMPLE 66

Step A:

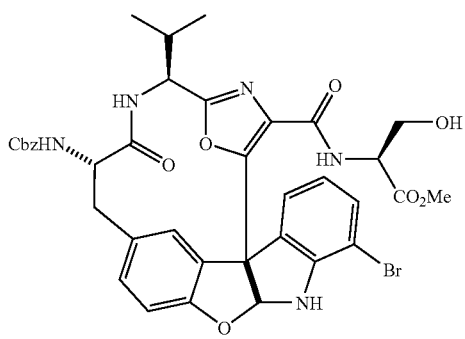

The conditions for this reaction are similar to those used for Step A of Example 44. The carboxylic acid synthesized in Example 2 and L-serine methyl ester hydrochloride served as the starting materials.

Step B:

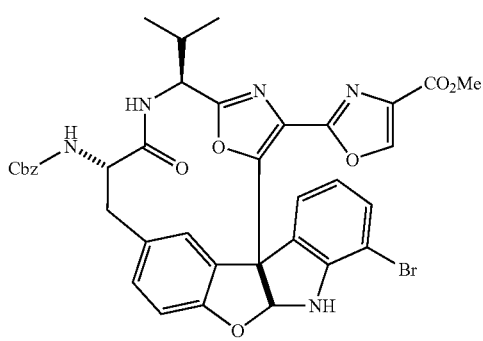

The conditions for this reaction are similar to those used for Step A of Example 46. The material synthesized in Step A above served as the starting material.

Step C:

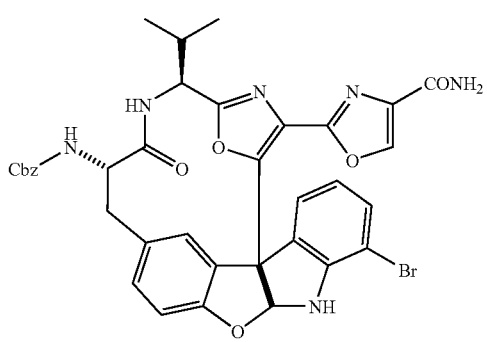

To a microwave reaction tube were added the material synthesized in Step B above (11 mg, 0.0146 mmol), THF (2 mL) and aqueous ammonium hydroxide (28%, 2 mL) and the tube was sealed. The resulting reaction solution was irradiated by microwave at 80° C. for 90 min. After cooling to RT, the tube was opened carefully. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous NaHSO$_4$ (20 mL), water (20 mL), saturated aqueous NaHCO$_3$ (20 mL), and brine (2×20 mL), and then dried over Na$_2$SO$_4$. After concentration the crude product was purified by PTLC eluting with MeOH/CH$_2$Cl$_2$ (9/91) to afford desired product as an off-white solid (9 mg, 0.0122 mmol, 83%). MS: m/z=739.0 (M+1).

Step D:

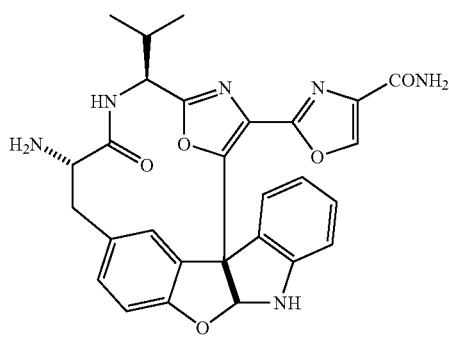

The conditions for this reaction are similar to those used for Step B of Example 11. The material synthesized in Step C above served as the starting material.

Step E:

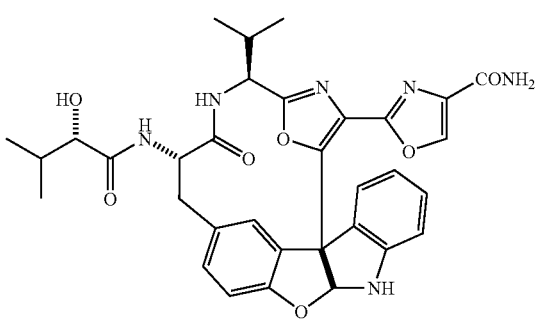

The conditions for this reaction are similar to those used for Step C of Example 11. The material synthesized in Step D above served as the starting material. MS: m/z=627.0 (M+1).

EXAMPLE 67

Step A:

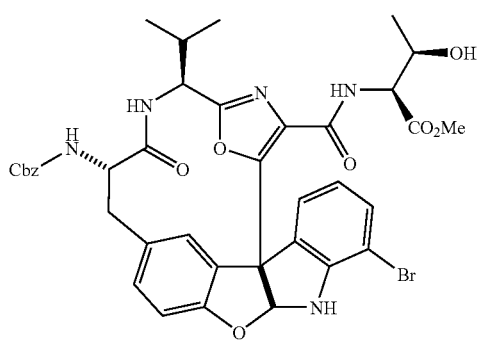

To a dry 15-mL flask with magnetic stir bar was added the carboxylic acid synthesized in Example 2 (105 mg, 0.154 mmol), L-threonine methyl ester hydrochloride (32 mg, 0.187 mmol, 1.2 eq.), HOBt (25 mg, 0.187, 1.2 eq.), anhydrous DMF (3 mL) and N,N-diisopropylethylamine (0.065 mL, 0.374 mmol, 2.4 eq.). The reaction mixture was cooled to 0° C. followed by addition of EDC (36 mg, 0.187, 1.2 eq.). The resulting reaction mixture was stirred at RT for 18 h. The reaction was monitored by LCMS. The reaction mixture was diluted with EtOAc (60 mL)/water (20 mL). The organic phase was separated and the aqueous phase was extracted by EtOAc (2×20 mL). The combined organic layers were washed by water (20 mL), 10% aqueous NaHSO$_4$ (20 mL), water (20 mL), saturated NaHCO$_3$ (20 mL), and brine (2×20 mL), and then dried over Na$_2$SO$_4$. After concentration the crude product was used in next step without further purification. MS: m/z=788.1 (M+1).

Step B:

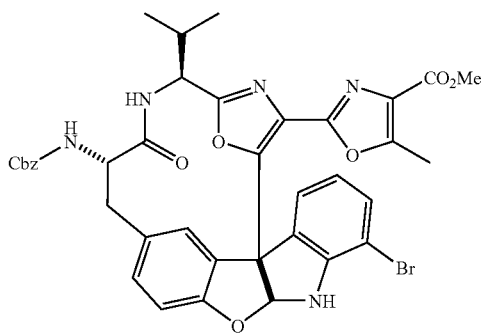

To a dry flask were added material synthesized in Step A above (114 mg, 0.148 mmol) and anhydrous CH$_2$Cl$_2$ (2 mL). The reaction solution was cooled to −20° C. in a dry ice/acetone-water bath and turned cloudy. Bis(2-methoxyethyl)aminosulfur trifluoride (0.041 mL, 0.22 mmol, 1.5 eq.) was added dropwise. The resulting reaction mixture was stirred at −20° C. for 1 h, and warmed to RT for 10 min. The mixture was cooled back to 0° C., and DBU (0.155 mL, 1.036 mmol, 7 eq.) and CBrCl$_3$ (0.102 mL, 1.036 mmol, 7 eq.) were added. The resulting mixture was allowed to warm to RT slowly overnight. The reaction mixture was quenched by addition of saturated aqueous NaHCO$_3$ (3 mL), diluted with EtOAc (60 mL), washed with water (2×20 mL) as well as brine (20 mL), dried over Na$_2$SO$_4$. After concentration the residue was purified by PTLC eluting with MeOH/CH$_2$Cl$_2$ (7/93) to afford desired product as an off-white solid (85 mg, 0.11 mmol, 78% for two steps). MS: m/z=768.0 (M+1).

Step C:

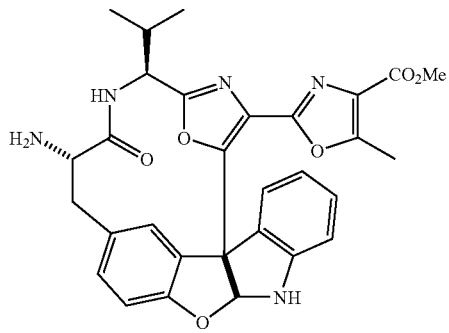

The conditions for this reaction are similar to those used for Step B of Example 11. The oxazole synthesized in Step B above served as the starting material. The crude product was used directly in the next step without purification.

Step D:

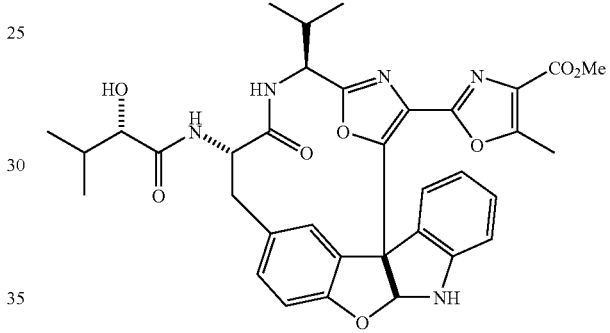

The conditions for this reaction are similar to those used for Step C of Example 11. The amine synthesized in Step C above served as the starting material. MS: m/z=656.1 (M+1).

EXAMPLES 68-70

The compounds in Examples 68-70 were prepared using coupling conditions similar to those used in Example 7. The amine synthesized in Step C of Example 67 served as the starting material. Coupling of this amine with a series of carboxylic acids produced the amide derivatives.

| | | MS m/z |
|---|---|---|
| Example 68 | 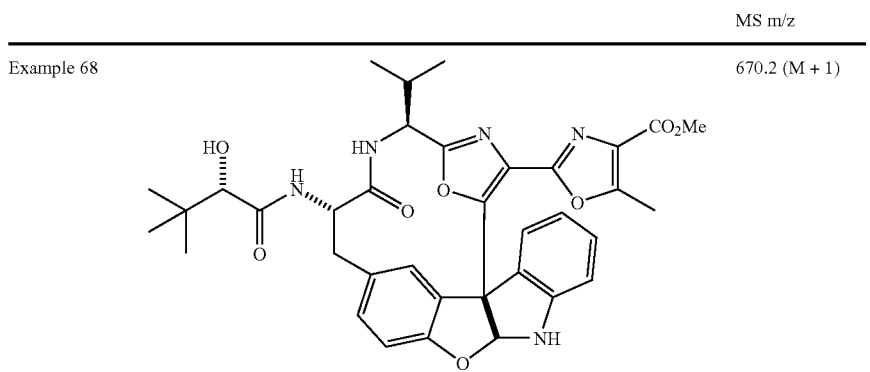 | 670.2 (M + 1) |

|  | MS m/z |
|---|---|
| Example 69 | 670.0 (M + 1) |
| Example 70 | 670.0 (M + 1) |

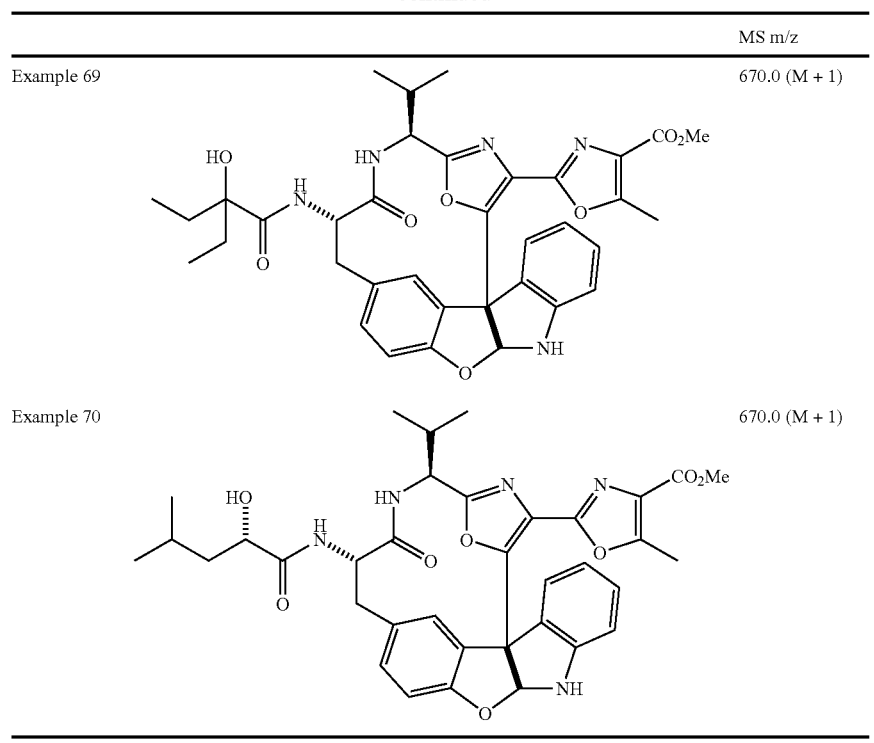

EXAMPLE 71

Step A:

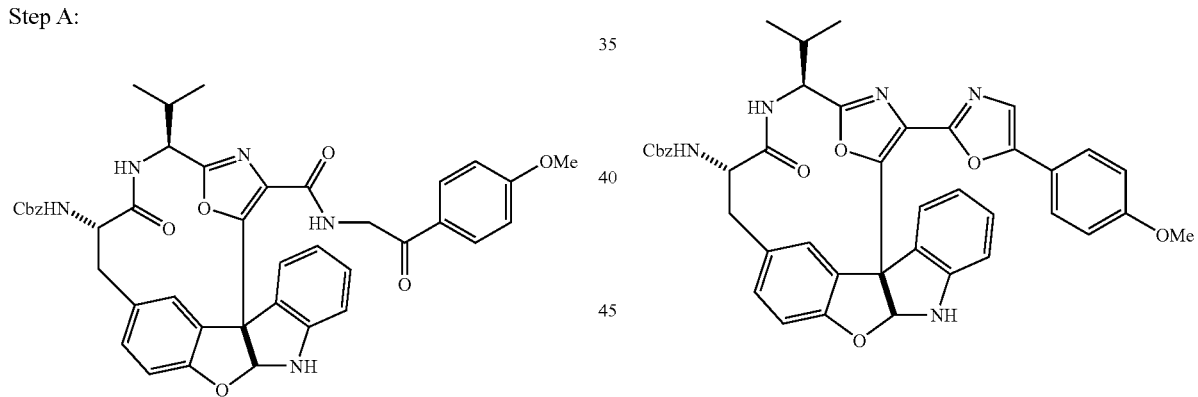

To a dry 15-mL flask with magnetic stir bar was added the carboxylic acid synthesized in Example 5 (25 mg, 0.042 mmol), 2-amino-4'-methoxyacetophenone hydrochloride (10 mg, 0.050 mmol, 1.2 eq.), HOBt (6.2 mg, 0.046, 1.1 eq.), anhydrous DMF (1 mL) and N,N-Diisopropylethylamine (0.016 mL, 0.092 mmol, 2.2 eq.). The reaction mixture was cooled to 0° C. followed by addition of EDC (8.9 mg, 0.046, 1.1 eq.). The resulting reaction mixture was stirred at RT for 18 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous $NaHSO_4$ (20 mL), water (20 mL), saturated $NaHCO_3$ (20 mL), and brine (2×20 mL), and then dried over $Na_2SO_4$. After concentration the crude product was used in next step without further purification.

Step B:

Triphenylphosphine (57 mg, 0.216 mmol, 10 eq.) and hexachloroethane (51 mg, 0.216 mmol, 10 eq.) were added to a dry 15-mL flask equipped with a thermometer, and a magnetic stir bar. Anhydrous $CH_2Cl_2$ (2 mL) was added and the resulting solution was cooled to 10° C. in ice-water bath under $N_2$. Triethylamine (0.042 mL, 0.302 mmol, 14 eq.) was added slowly to the solution, followed by stirring for 10 min. at 10° C. The solution of material from Step A above (16 mg, 0.0216 mmol, 1 eq.) in anhydrous $CH_2Cl_2$ (1 mL) was added dropwise over 2 min. and the temperature was kept at 10-12° C. The reaction mixture was stirred at 10° C. for another 10 min., and TLC showed that no SM left. The reaction mixture was cooled to −30° C. followed by addition of phosphate buffer (3 mL, pH=6.9, 0.5 M) to consume excess reagents. The resulting reaction mixture was stirred in cold room (4° C.) for 48 h. Most of triphenylphosphine was consumed as determined by LCMS. The organic phase was separated and the aqueous phase was extracted by $CH_2Cl_2$ (2×10 mL). Combined organic phase was washed by water (10 mL) and brine (10 mL) and dried over Na$_2$SO$_4$ After concentration the residue was purified by PTLC eluting with MeOH/CH$_2$Cl$_2$ (8/92) to afford desired product as an off-white solid (3 mg, 0.00415 mmol, 20% for two steps). MS: m/z=723.7 (M+1).

Step C:

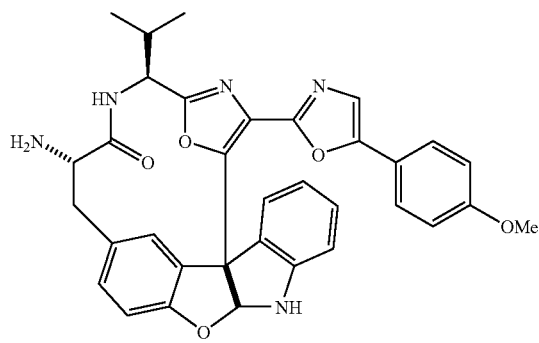

The conditions for this reaction are similar to those used for Step B of Example 11. The material synthesized in Step B above served as the starting material. The crude product was used directly in the next step without further purification.

Step D:

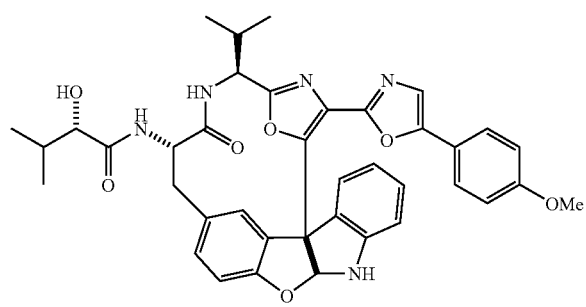

The conditions for this reaction are similar to those used for Step C of Example 11. The material synthesized in Step C above served as the starting material. MS: m/z=689.8 (M+1).

EXAMPLE 72

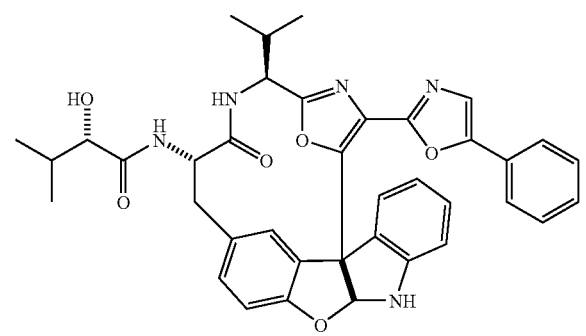

The conditions for the synthesis of this compound are similar to the those used in Example 71 (Steps A-D).

2-Amino-4'-methoxyacetophenone hydrochloride was replaced by 2-aminoacetophenone hydrochloride in Step A. MS: m/z=659.8 (M+1).

EXAMPLE 73

Step A:

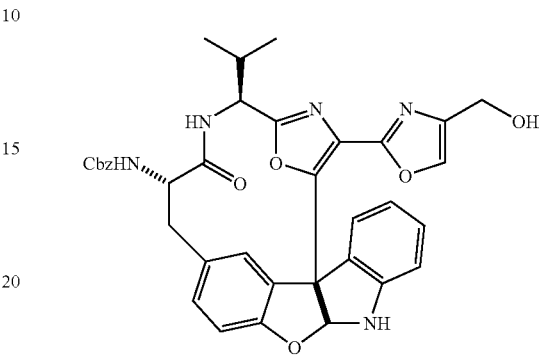

To a dry flask were added crude material synthesized in Step A of Example 46 (210 mg, 0.311 mmol), THF (4 mL) and 2-propanol (12 mL). This solution was cooled to 0° C. followed by addition of solid lithium borohydride (67.7 mg, 3.11 mmol, 10 eq.). The resulting mixture was allowed to warm to RT and stirred for 18 h. The reaction was monitored with LCMS. Almost no starting material remained. The reaction mixture was cooled to 0° C. and quenched by addition of aqueous sodium bisulfate (10%, 10 mL). Then the reaction mixture was diluted with EtOAc (200 mL)/water (30 mL). The organic phase was separated and the aqueous phase was extracted by EtOAc (2×50 mL). The combined organic layers were washed by water (50 mL), saturated NaHCO$_3$ (50 mL), and brine (2×50 mL), and then dried over Na$_2$SO$_4$. After concentration the residue was purified by PTLC eluting with MeOH/CH$_2$Cl$_2$ (9/91) to afford desired product as an off-white solid (70 mg, 0.108 mmol, 35% for two steps). MS: m/z=648.2 (M+1).

Step B:

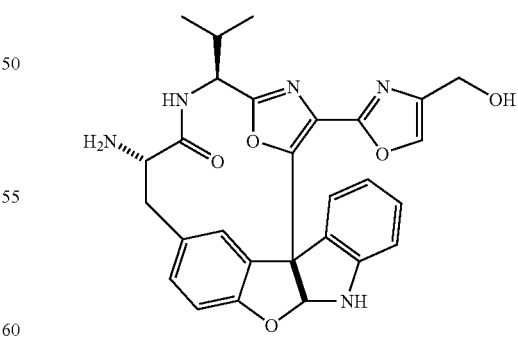

The conditions for this reaction are similar to those used for Step B of Example 11. The material synthesized in Step A above served as the starting material. The crude product was used directly in the next step without further purification.

Step C:

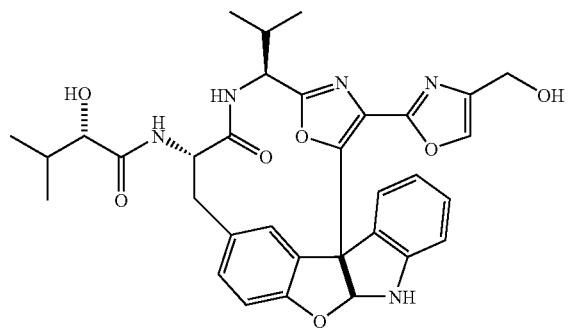

The conditions for this reaction are similar to those used for Step C of Example 11. The material synthesized in Step B above served as the starting material. MS: m/z=614.2 (M+1).

EXAMPLE 74

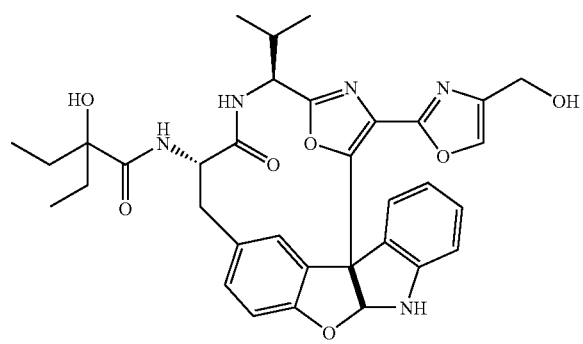

To a dry 15-mL flask with magnetic stir bar were added the amine synthesized in Step B of Example 73 (2.7 mg, 0.00525 mmol), anhydrous DMF (1 mL), a stock solution of 2-ethyl-2-hydroxyl butanoic acid (1.04 mg, 0.00787 mmol, 1.5 eq.) in DMF (0.050 mL), a stock solution of HOBt (1.4 mg, 0.0105 mmol, 2.0 eq.) in DMF (0.050 mL), and a stock solution of N,N-disopropylethylamine (0.0018 mL, 0.0105 mmol, 2.0 eq.) in DMF (0.050 mL). The reaction mixture was cooled to 0° C. followed by addition of a stock solution of EDC (2.0 mg, 0.0105, 2.0 eq.) in DMF (0.100 mL). The resulting reaction mixture was stirred at RT for 18 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed by water (20 mL), 10% aqueous NaHSO$_4$ (20 mL), water (20 mL), saturated NaHCO$_3$ (20 mL), and brine (2×20 mL), and then dried over Na$_2$SO$_4$. After concentration the crude product was purified by PTLC eluting with MeOH/CH$_2$Cl$_2$ (13/87) to afford desired product as an off-white solid (1.7 mg, 0.00271 mmol, 52%). MS: m/z=627.5 (M+1).

EXAMPLE 75

Step A:

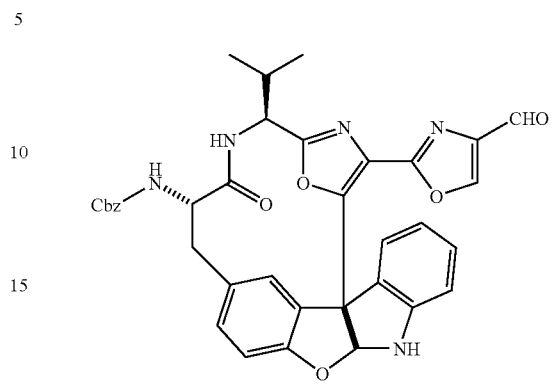

To a solution of the ester synthesized in Step A of Example 46 (48 mg, 0.071 mmol, 1.0 eq.) in CH$_2$Cl$_2$ (2 mL) was added DIBAL-H (1 M in toluene, 0.28 mL, 0.28 mmol, 4.0 eq.) dropwise at −78° C. The resulting mixture was stirred at that temperature for 1 h and then quenched with methanol (0.1 mL). Potassium sodium tartrate solution (25%, 10 mL) was added and the mixture was stirred at RT for 1 h. The aqueous layer was separated and extracted with EtOAc. The combined organic layers were washed with brine, dried over Na$_2$SO$_4$ and concentrated. PTLC provided the aldehyde product. MS: m/z=645.5 (M+1).

Step B:

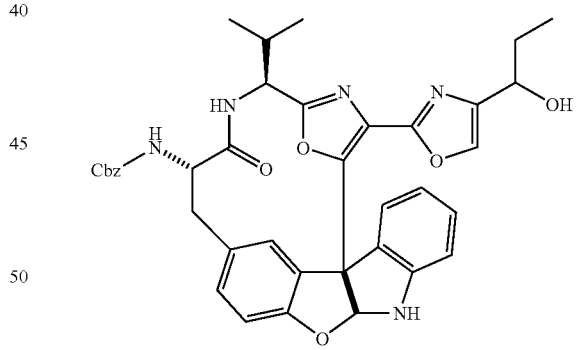

To the solution of the aldehyde synthesized in Step A above (39 mg, 0.06 mmol, 1.0 eq.) in THF (5 mL) was added ethylmagnesium bromide solution (1 M in THF, 1.2 mL, 1.2 mmol, 20 eq.) dropwise at −78° C. The reaction was warmed up to −30° C. and stirred for 30 min. The reaction was quenched with ammonium chloride solution and the resulting mixture was extracted with EtOAc (3×20 mL). The combined organic layers were washed with brine, dried over Na$_2$SO$_4$ and concentrated. The crude product was purified by PTLC to provide 15 mg of the alcohol product.

Step C:

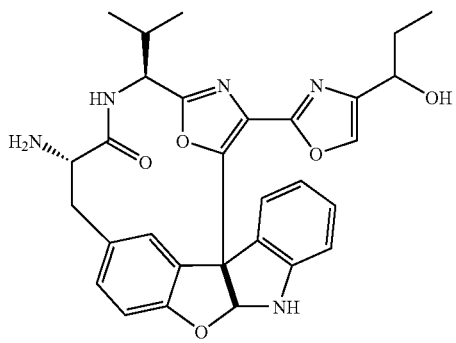

To the solution of the Cbz derivative synthesized in Step B above 74 (15 mg, 0.022 mmol) in THF (2.5 mL) was added 10% Pd/C (7.5 mg). The reaction flask was purged with $H_2$ and equipped with $H_2$ balloon. The reaction was stirred at RT overnight. The resulting mixture was filtered through a Celite pad and the filtrate was concentrated. The crude material was used for next step without further purification. MS: m/z=542.3 (M+1).

Step D:

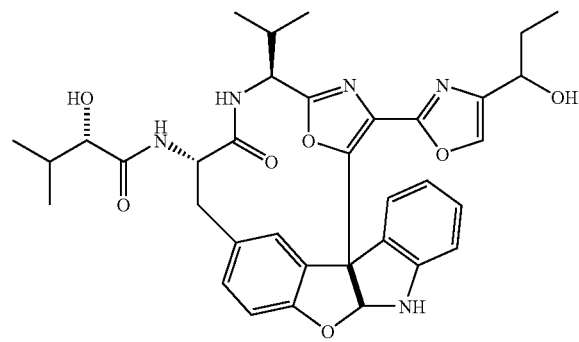

To the solution of the crude amine synthesized in Step C above (12 mg, 0.022 mmol, 1.0 eq.) and (S)-2-hydroxy-3-methylbutyric acid (4 mg, 0.033 mmol, 2.0 eq.) in DMF (1 mL) was added HOBt (4.5 mg, 0.033 mmol, 1.5 eq.), N,N-diisopropylethylamine (0.0076 mL, 0.044 mmol, 2.0 eq.) and EDC (6.3 mg, 0.033 mmol, 1.5 eq.). The resulting mixture was stirred at RT overnight. To the reaction mixture was added EtOAc and the organic layer was washed with water, 1 N aqueous HCl, saturated aqueous $NaHCO_3$, water and brine. The crude product was purified by PTLC to provide 3 mg of the coupling product. MS: m/z=642.3 (M+1).

EXAMPLE 76

Step A:

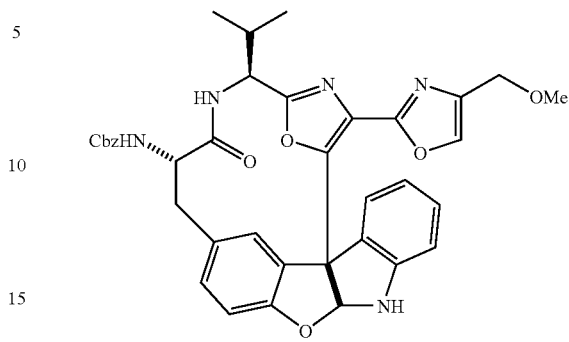

To a dry 15-mL flask were added the material from synthesized in Step A of Example 73 (10 mg, 0.0154 mmol), proton sponge (6.6 mg, 0.0308 mmol, 2.0 eq.) and anhydrous $CH_2Cl_2$ (2 mL). The reaction solution was cooled to −20° C. in dry ice/acetone-water bath. Trimethyloxonium tetrafluoroborate (2.7 mg, 0.0185 mmol, 1.2 eq.) was added. The resulting mixture was stirred at −20° C. under $N_2$ for 1 h followed by being quenched with saturated aqueous $NaHCO_3$ (2 mL). The reaction mixture was diluted with EtOAc (20 mL), washed with water (10 mL), brine (10 mL) and dried over $Na_2SO_4$. After concentration the crude product was purified by PTLC eluting with $MeOH/CH_2Cl_2$ (8/92) to afford desired product as an off-white solid (3.0 mg, 0.00454 mmol, 29%). MS: m/z=662.3 (M+1).

Step B:

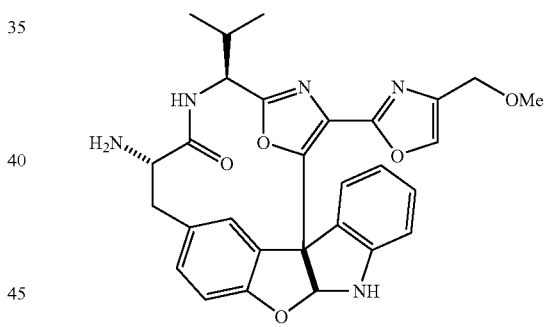

The conditions for this reaction are similar to those used for Step B of Example 11. The material synthesized in Step A above served as the starting material. The crude product was used directly in the next step without further purification.

Step C:

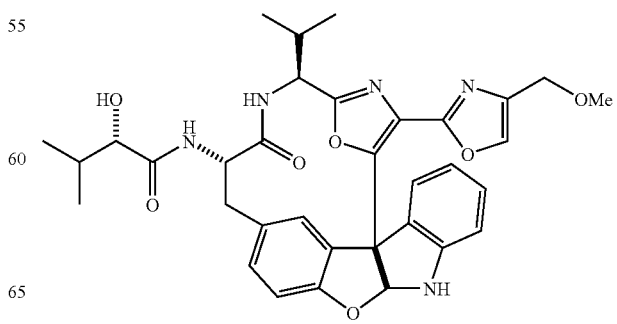

The conditions for this reaction are similar to those used for Step C of Example 11. The material synthesized in Step B above served as the starting material. MS: m/z=628.2 (M+1).

EXAMPLE 77

Step A:

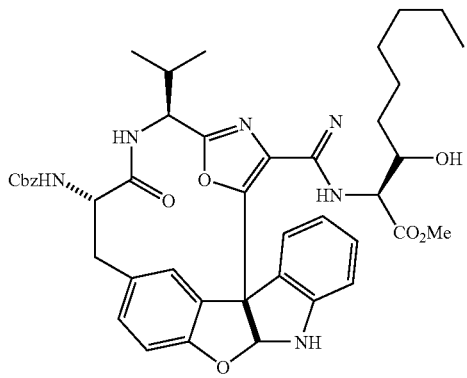

The conditions for this reaction are similar to those used for Step A of Example 44. L-Serine methy ester hydrochloride was replaced by the trifluoroacetic acid salt of methyl (2,S)-amino-(3,R/S)-hydroxynonanoate. Methyl (2,S)-amino-(3,R/S)-hydroxynonanoate was synthesized by an adaptation of the procedure of U. Schöllkopf, et al. (*Liebigs Ann. Chem.* 1983, 1133-1151). MS: m/z=780.4 (M+1).

Step B:

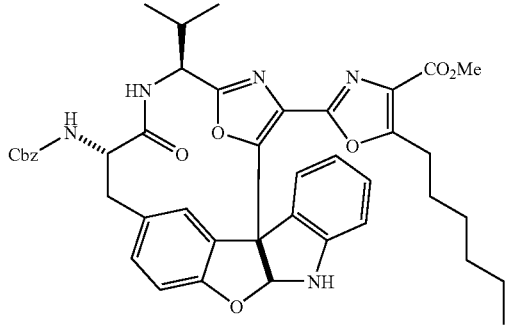

The conditions for this reaction are similar to those used for Step A of Example 46. The compound synthesized in Step A above served as the starting material. MS: m/z=760.3 (M+1).

Step C:

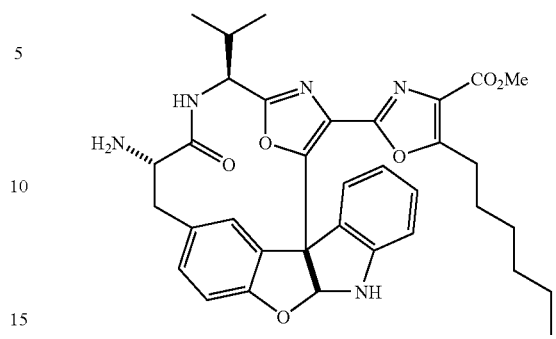

The conditions for this reaction are similar to those used for Step B of Example 46. The compound synthesized in Step B above served as the starting material. MS: m/z=626.3 (M+1).

Step D:

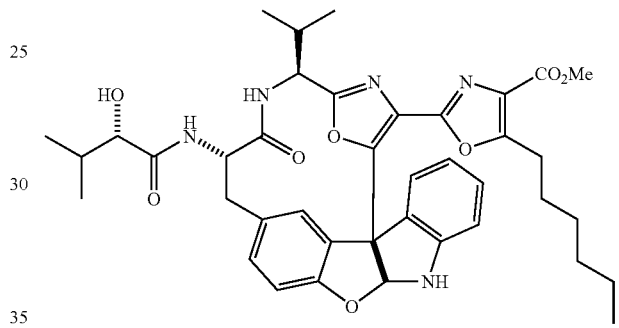

The conditions for this reaction are similar to those used for Step C of Example 46. The compound synthesized in Step C above served as the starting material. MS: m/z=726.3 (M+1).

EXAMPLE 78

Step A:

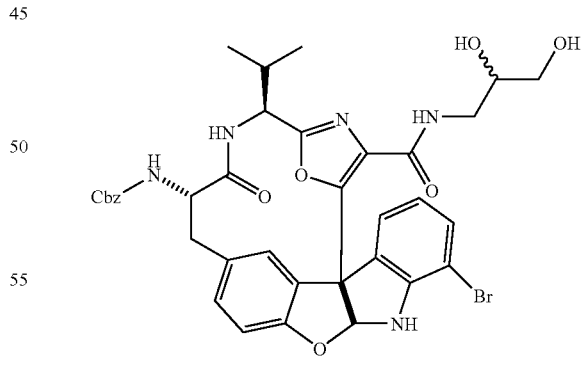

The compound synthesized in Example 2 (60 mg, 0.089 mmol) and HOBt (15 mg, 0.11 mmol) were dissolved in DMF (1.1 mL). 3-Amino-1,2-propanediol (9 mg, 0.10 mmol) and additional DMF (0.1 mL) were added, followed by a small amount of 3A molecular sieve pellets. EDC (21 mg) was then added and the mixture was stirred at RT overnight. The mixture was diluted into EtOAc (20 mL) and the solution was washed with 1 N aqueous HCl (10 mL), saturated aqueous NaHCO$_3$ (5 mL) and saturated aqueous NaCl (5 mL). The organic layer was dried (Na$_2$SO$_4$), decanted, and evaporated to give 66 mg of the amide derivative. MS: m/z=746.1 (M+1).
Step B:

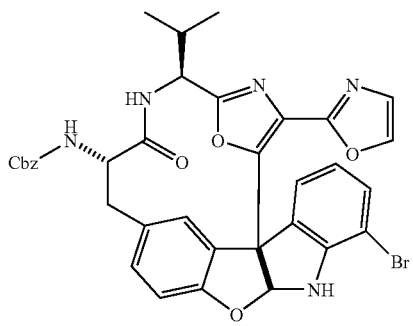

The compound synthesized in Step A above (63 mg, 0.084 mmol) was dissolved in THF (1.7 mL) and a solution of NaIO$_4$ (23 mg, 0.11 mmol) in water (0.20 mL) was added, followed by additional water (0.10 mL) to rinse. After 2.25 h, additional NaIO$_4$ (9 mg, 0.042) in water (0.10 mL). After an additional 2 h, the mixture was diluted into EtOAc (20 mL) and washed with saturated aqueous NaHCO$_3$ (10 mL) and saturated aqueous NaCl (10 mL). The organic layer was dried (Na$_2$SO$_4$), decanted, and evaporated to give 63 mg of intermediate aldehyde as a colorless brittle glass. This material was dissolved in CH$_2$Cl$_2$ (2.4 mL) and a small amount of 3A molecular sieve pellets was added. Following the general method of Hendrickson, et al. (*J. Org. Chem.* 1987, 52, 4137-4139), a solution of N-diphenylphosphinyl-N'-methylpiperazine (344 mg, 1.15 mmol) in dry CH$_2$Cl$_2$ (4.2 mL) was cooled in an ice bath and treated with triflic anhydride (0.091 mL, 153 mg, 0.54 mmol). After 30 min., the solution of the aldehyde was added. After an additional 1.5 h, the reaction was quenched by addition of 1 N aqueous HCl (15 mL) and the mixture was transferred to a separatory funnel with additional EtOAc (25 mL). The organic layer was washed with 1 N aqueous HCl, saturated aqueous NaHCO$_3$, and saturated aqueous NaCl (15 mL of each). The organic layer was dried (Na$_2$SO$_4$), decanted, and evaporated. Flash column chromatography on silica gel using 25% or 30% EtOAc in CH$_2$Cl$_2$ gave 13 mg of the bis-oxazole derivative. MS: m/z=696.2 (M+1).
Step C:

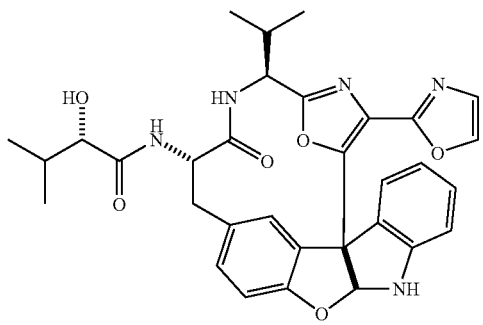

The compound synthesized in Step B above (13 mg, 0.019 mmol) was dissolved in methanol (3.0 mL), and 10% palladium on carbon (4 mg) was added followed by N,N-diisopropylethylamine (0.010 mL, 7.4 mg, 0.057 mmol). The mixture was stirred under an atmosphere of hydrogen for 1.25 h. The mixture was then filtered through a 0.45 micron membrane, with additional methanol to rinse the filter and catalyst. The filtrate was evaporated and the residue was dissolved in DMF (0.50 mL) along with HOBt (3.5 mg, 0.026 mmol) and L-α-hydroxyisovalereric acid (3.0 mg, 0.025 mmol). N,N-Diisopropylethylamine (0.004 mL, 3 mg, 0.023 mmol) was added, followed by EDC (4.4 mg, 0.023 mmol) and the solution was stirred overnight at RT. The reaction mixture was then diluted into EtOAc (20 mL) and washed with 1 N aqueous HCl (10 mL), saturated aqueous NaHCO$_3$ (5 mL), and saturated aqueous NaCl (5 mL). The organic layer was dried (Na$_2$SO$_4$), decanted, and evaporated. The crude product was purified by flash column chromatography on silica gel, eluting with 4:1 EtOAc/CH$_2$Cl$_2$, to give 8.1 mg of amide product as a white solid. MS: m/z=584.2 (M+1).

EXAMPLE 79

Step A:

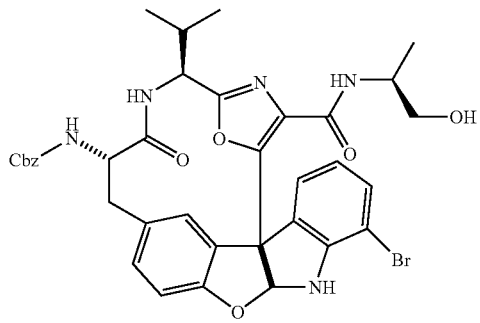

The compound synthesized in Example 2 was coupled with (S)-2-amino-1-propanol using the same conditions described for Step A of Example 78. This yielded the amide derivative.
Step B:

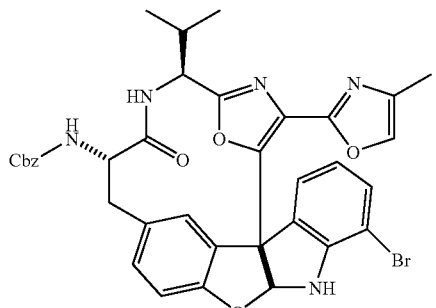

The compound synthesized in Step A above (62 mg, 0.085 mmol) was dissolved in CH$_2$Cl$_2$ (1.5 mL) and a solution of Dess-Martin periodinane (45 mg, 0.11 mmol) in CH$_2$Cl$_2$ (0.60 mL) was added. After 1 h, a solution of Na$_2$S$_2$O$_3$ (155 mg) in a mixture of saturated aqueous NaHCO$_3$ (0.32 mL) and water (0.10 mL) was added and the mixture was stirred at RT for 30 min. The mixture was diluted into EtOAc (20 mL) and washed with saturated aqueous NaHCO$_3$ (2×5 mL) and saturated aqueous NaCl (5 mL). The organic layer was dried (Na$_2$SO$_4$), decanted, and evaporated to give 64 mg of intermediate aldehyde. This material was dissolved in CH$_2$Cl$_2$ and treated with a solution of N-diphenylphosphinyl-N'-methylpiperazine activated with triflic anhydride as described in Step B of Example 78. This yielded 26 mg of the bis-oxazole derivative. MS: m/z=710.1(M+1).

Step C:

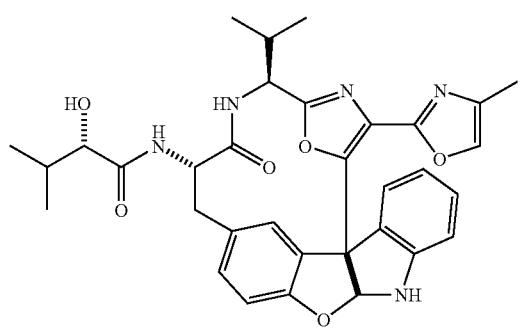

The compound synthesized in Step B above was hydrogenated as described in Step C of Example 78, using absolute ethanol in place of methanol. A longer reaction time was required. The crude intermediate amine was then coupled with L-α-hydroxyisovaleric acid and the product was isolated as described in Step C of Example 78 to give 16 mg of the amide derivative. MS: m/z=598.2 (M+1).

EXAMPLE 80

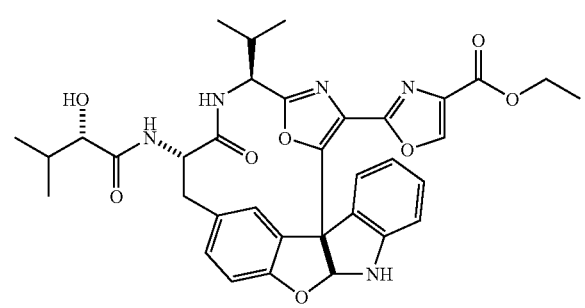

To a dry flask were added the material synthesized in Step C of Example 46 (5 mg, 0.0078 mmol), and a stock solution of sodium t-butoxide (0.75 mg, 0.0078 mmol, 1.0 eq.) in anhydrous ethanol (1 mL). The resulting mixture was stirred at RT for 4 h. The reaction was monitored by LCMS. The reaction mixture was diluted with EtOAc (30 mL), washed with saturated ammonium chloride solution in water (10 mL) as well as brine (2×10 mL), and dried over Na$_2$SO$_4$. After concentration the crude product was purified by PTLC eluting with MeOH/CH$_2$Cl$_2$ (8/92) to afford desired product as an off-white solid (5.0 mg, 0.0076 mmol, 98%). MS: m/z=656.2 (M+1).

EXAMPLE 81

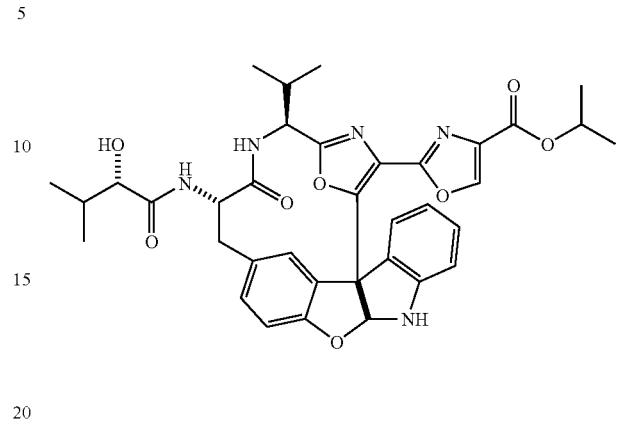

To a dry flask were added the material synthesized in Step C of Example 46 (5 mg, 0.0078 mmol), and a stock solution of sodium t-butoxide (0.75 mg, 0.0078 mmol, 1.0 eq.) in anhydrous 2-propanol (2 mL). The resulting mixture was stirred at RT for 4 h. The reaction was monitored by LCMS. The reaction mixture was diluted with EtOAc (30 mL), washed with saturated ammonium chloride solution in water (10 mL) as well as brine (2×10 mL), and dried over Na$_2$SO$_4$. After concentration the crude product was purified by PTLC eluting with MeOH/CH$_2$Cl$_2$ (8/92) to afford desired product as an off-white solid (2.9 mg, 0.0043 mmol, 55%). MS: m/z=670.2 (M+1).

EXAMPLE 82

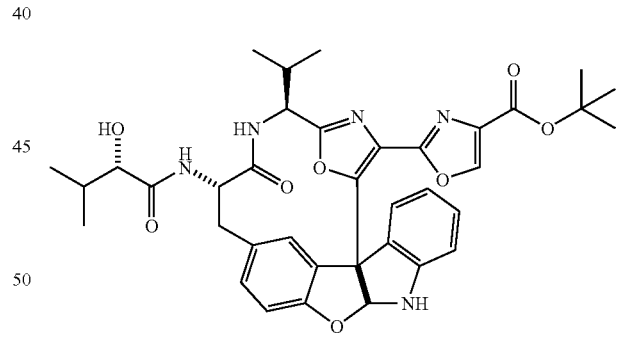

To a dry flask containing 4A molecular sieve (20 mg) were added the material synthesized in Step C of Example 46 (5 mg, 0.0078 mmol) and a stock solution of sodium t-butoxide (0.75 mg, 0.0078 mmol, 1.0 eq.) in anhydrous t-butanol (2 mL). The resulting mixture was stirred at 28° C. for 4 h. The reaction was monitored by LCMS. The reaction mixture was diluted with EtOAc (30 mL), washed with saturated ammonium chloride solution in water (10 mL) as well as brine (2×10 mL), and dried over Na$_2$SO$_4$. After concentration the crude product was purified by PTLC eluting with MeOH/CH$_2$Cl$_2$ (8/92) to afford desired product as an off-white solid (1.5 mg, 0.0022 mmol, 28%). MS: m/z=684.3 (M+1).

EXAMPLE 83

Step A:

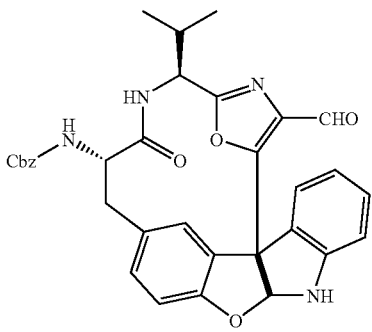

To a dry 15-mL-flask were added the material synthesized in Example 4 (50 mg, 0.0822 mmol) and anhydrous $CH_2Cl_2$ (2 mL). The solution was cooled to $-78°$ C. in dry ice/acetone bath followed by addition of a solution of DIBAL-H in toluene (1 M, 0.288 mL, 0.228 mmol, 3.5 eq.). The resulting reaction mixture was stirred at $-78°$ C. under $N_2$ for 1 h. Methanol (0.5 mL) was added slowly to quench the reaction at $-78°$ C. followed by addition of a solution of potassium sodium tartrat in water (20%, 2 mL). The mixture was warmed to RT. The reaction mixture was diluted with EtOAc (30 mL), washed with saturated ammonium chloride solution in water (10 mL) as well as brine (2×10 mL), and dried over $Na_2SO_4$. After concentration the crude product was purified by PTLC eluting with $MeOH/CH_2Cl_2$ (8/92) to afford desired product as an off-white solid (20 mg, 0.0346 mmol, 42%). MS: m/z=579.2 (M+1).

Step B:

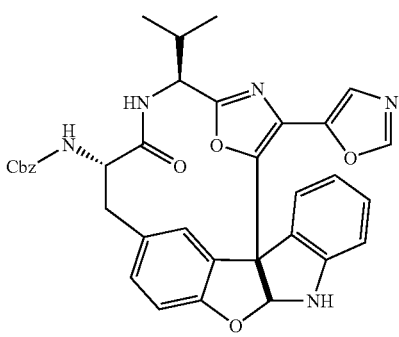

To a dry 15-mL-flask were added material synthesized in Step A above (8 mg, 0.0138 mmol), p-toluenesulfonylmethyl isocyanide (3.0 mg, 0.0152 mmol, 1.1 eq.), $K_2CO_3$ (4.2 mg, 0.0304 mmol, 2.2 eq.) and methanol (2 mL). The resulting mixture was refluxed for 2 h. The reaction was monitored with LCMS. After most of solvent was removed under reduced pressure, the residue was purified by PTLC eluting with $MeOH/CH_2Cl_2$ (8/92) to afford desired product as an off-white solid (5 mg, 0.0081 mmol, 59%). MS: m/z=618.2 (M+1).

Step C:

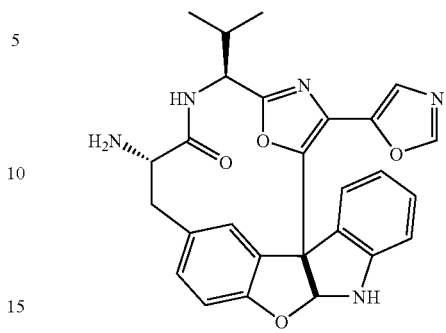

The conditions for this reaction are similar to those used for Step B of Example 11. The compound synthesized in Step B above served as the starting material. The crude product was used directly in the next step without further purification.

Step D:

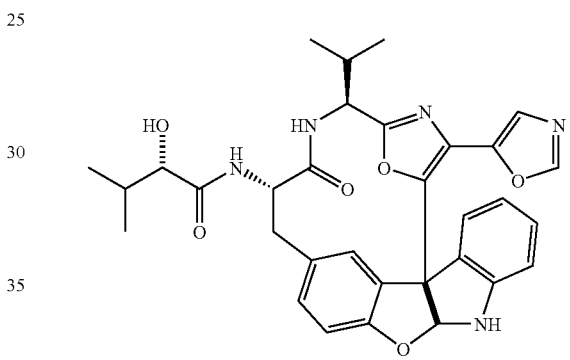

The conditions for this reaction are similar to those used for Step C of Example 11. The compound synthesized in Step C above served as the starting material. MS: m/z=583.5 (M+1).

EXAMPLE 84

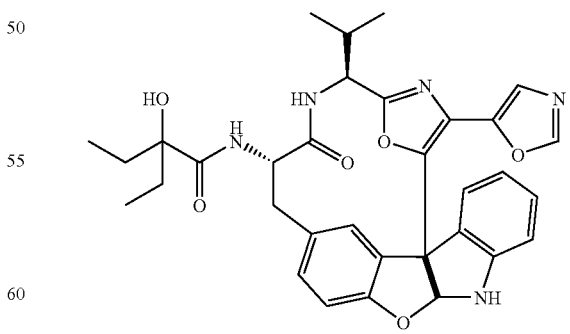

The conditions for this reaction are similar to those used for Example 74. 2-Ethyl-2-hydroxyl butanoic acid and the compound synthesized in Step C of Example 83 served as the starting materials. MS: m/z=597.6 (M+1).

EXAMPLE 85

Step A:

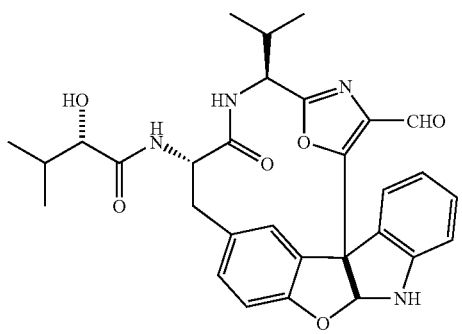

The conditions for this reaction are similar to those used for Step A of Example 83. The compound synthesized in Example 6 served as the starting material. MS: m/z=545.3 (M+1).

Step B:

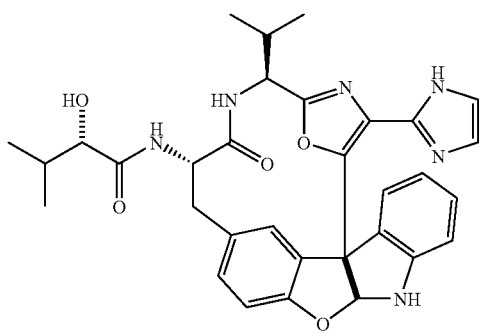

To a small-scale reaction tube were added the material synthesized in Step A above (8 mg, 0.0147 mmol), methanol (0.2 mL), aqueous ammonium hydroxide (30%, 0.5 mL) and glyoxal (40% in water, 0.0134 mL, 0.294 mmol, 20 eq.). The tube was sealed and the reaction solution was stirred at RT for 20 h. The reaction was monitored with LCMS. The reaction mixture was diluted with EtOAc (30 mL), washed with brine (2×10 mL), and dried over $Na_2SO_4$. After concentration the crude product was purified by PTLC eluting with MeOH/$CH_2Cl_2$ (12/88) to afford desired product as an off-white solid (2.8 mg, 0.0048 mmol, 33%). MS: m/z=583.2 (M+1).

EXAMPLE 86

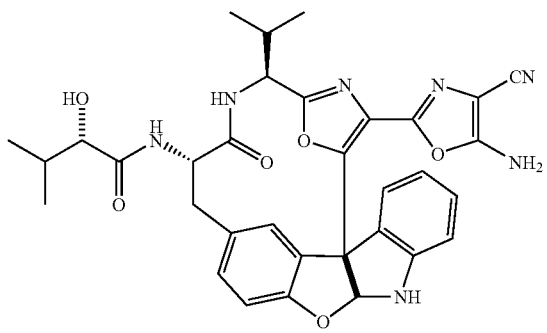

To a dry 15-mL flask were added the material synthesized in Example 12 (37 mg, 0.066 mmol), aminomalononitrile p-toluenesulfonate (17 mg, 0.066 mmol, 1.0 eq.), anhydrous pyridine (2 mL), and EDC (13 mg, 0.066 mmol, 1.0 eq.). the resulting reaction was stirred at RT for 22 h. The reaction mixture was diluted with chloroform (30 mL), washed with water (10 mL), brine (2×10 mL), and dried over $Na_2SO_4$. After concentration the crude product was purified by PTLC eluting with MeOH/$CH_2Cl_2$ (12/88) to afford desired product as an off-white solid (5.6 mg, 0.0090 mmol, 14%). MS: m/z=623.7 (M+1).

EXAMPLE 87

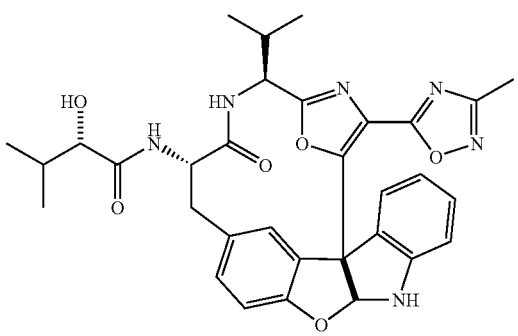

The oxadiazole ring was introduced using the general procedure described by G. Liang and D. D. Feng (*Tetrahedron Letters* 1996, 37, 6627-6630). The compound synthesized in Example 12 (0.018 mmol) was heated in diethylene glycol dimethyl ether at 50° C. overnight with acetamide oxime (0.018 mmol) and EDC (0.022 mmol). The reaction mixture was then further heated for 3 h at 110° C. After standard extractive work-up, purification using reverse phase HPLC gave the desired compound as a white solid. MS: m/z=599.3.

EXAMPLE 88

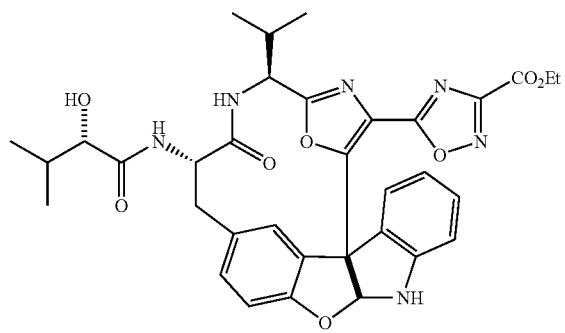

The compound in Example 88 was synthesized in a manner similar to Example 87, replacing acetamide oxime with ethyl 2-oximinooxamate. This reaction required 9 h of heating at 110° C. instead of the 3 h as described in Example 87. MS: m/z=657.3.

EXAMPLE 89

Step A:

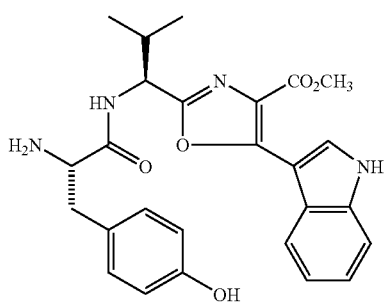

The conditions for this reaction are similar to those used for Step B of Example 11. The compound synthesized in Step F of Example 1 served as the starting material.

Step B:

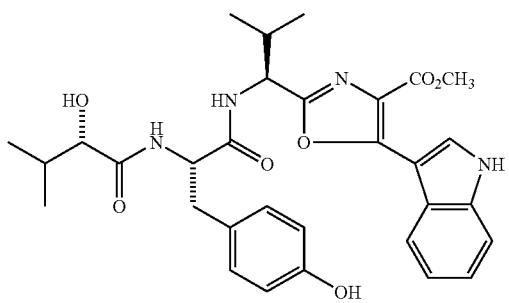

The coupling conditions for this reaction are similar to those described in Example 7. The compound synthesized in Step A above was served as the amine reactant, and (S)-2-hydroxy-3-methylbutyric acid was used in place of (S)-mandelic acid. MS: m/z=577.0 (M+1).

EXAMPLE 90

Step A:

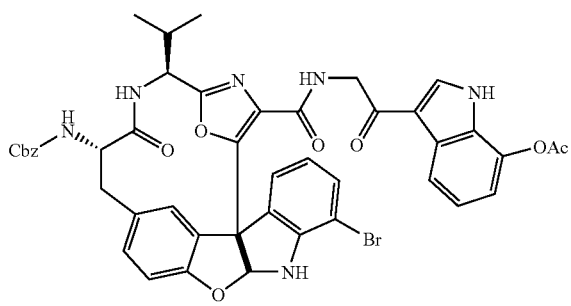

To a dry 50 mL flask containing crude product from Step A of Example 32 (78 mg, 0.09 mmol) was added anhydrous THF (0.4 mL) and anhydrous $CH_2Cl_2$ (1.7 mL). The resulting solution was cooled to 0° C. in ice-water bath. Acetic anhydride (0.027 mL, 0.27 mmol, 3.0 eq.) and pyridine (0.012 mL, 0.14 mmol, 1.5 eq.) were added sequentially at 0° C. Then the mixture was allowed to warm to RT and stirred under $N_2$. After 3.5 h the reaction solution was diluted with EtOAc (40 mL) followed by washing with brine (2×30 mL) and drying over $Na_2SO_4$. After concentration, the crude product (82 mg, 0.09 mmol, 99% yield) was obtained and used directly in next step without further purification. MS: m/z=887.2 (M+1).

Step B:

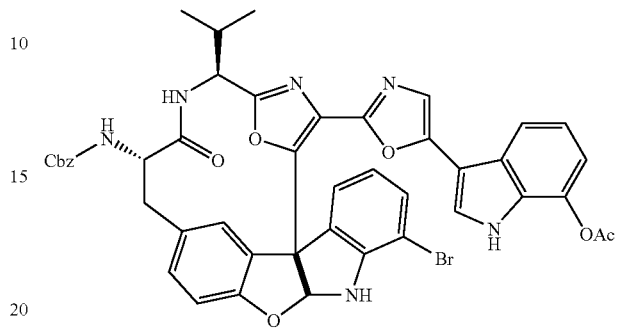

Triphenylphosphine (13.48 g, 51.4 mmol, 10 eq.) and hexachloroethane (12.17 g, 51.4 mmol, 10 eq.) were added to a dry 1-L three-neck round-bottom flask equipped with a thermometer, an addition funnel and a magnetic stir bar. Anhydrous $CH_2Cl_2$ (320 mL) was added and the resulting solution was cooled to 10° C. in ice-water bath under $N_2$. Triethylamine (10.03 mL, 71.96 mmol, 14 eq.) was added slowly to the solution, followed by stirring for 10 min. at 10° C. The solution of the compound synthesized in Step A above (4.56 g, 5.14 mmol, 1 eq.) in anhydrous $CH_2Cl_2$ (160 mL) was added dropwise over 5 min. and the temperature was kept at 10-12° C. The reaction mixture was stirred at 10° C. for another 10 min., and TLC showed that no SM left. The reaction mixture was cooled to −30° C. followed by addition of phosphate buffer (200 mL, pH=6.9, 0.5 M) to consume excess reagents. The resulting reaction mixture was stirred in cold room (4° C.) for 48 h. Most of triphenylphosphine was consumed as determined by LCMS. The organic phase was separated and the aqueous phase was extracted by $CH_2Cl_2$ (2×100 mL). Combined organic phase was washed by water (100 mL) and brine (100 mL) and dried over $Na_2SO_4$. All solvent was removed under reduced pressure on a rotary evaporator followed by the addition of EtOAc (40 mL) to precipitate triphenylphosphine oxide. After filtering and washing with $CH_2Cl_2$, the filtrate was concentrated. The crude product was purified by flash chromatography eluting with EtOAc/toluene (60/40; column 4×28 cm) to give desired product (3.41 g, 3.92 mmol, 76% yield). MS: m/z=869.1 (M+1).

Step C:

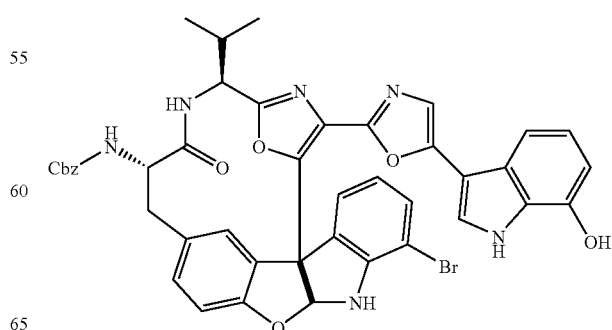

The compound synthesized in Step B above (1.50 g, 1.72 mmol) was dissolved in methanol (40 mL) and the solution was cooled in an ice bath. A solution of LiOH.H$_2$O (109 mg, 2.6 mmol) in water (2 mL) was added. After 1 h, the reaction mixture was diluted with water (60 mL) and acidified with 1 N aqueous HCl (4 mL). The resulting mixture was extracted with two portions of EtOAc (60 mL and 30 mL). The organic layers were washed in succession with saturated aqueous NaCl (30 mL), dried (Na$_2$SO$_4$), decanted, and evaporated to give 1.48 g of brittle tan foam. MS: m/z=826.7 (M+1).

Step D:

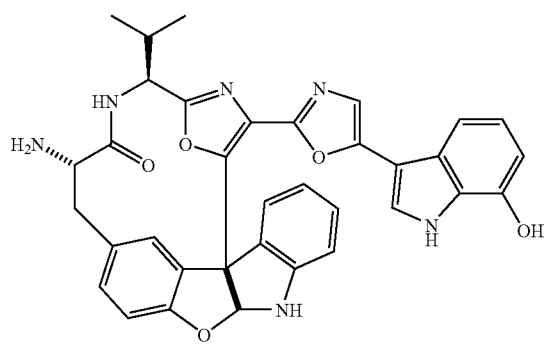

The compound synthesized in Step C above (250 mg, 0.302 mmol) was dissolved in methanol (15 mL) and 10% palladium on carbon (49 mg) was added. The mixture was stirred under an atmosphere of hydrogen for 5 h. The mixture was filtered through a 0.45 micron membrane and the catalyst was rinsed with additional methanol. The filtrate was evaporated and the residue was partitioned between EtOAc (25 mL) and saturated aqueous NaHCO$_3$ (15 mL) with added CH$_2$Cl$_2$ (10 mL). The organic layer was washed with saturated aqueous NaCl (10 mL), dried (Na$_2$SO$_4$), decanted, and evaporated to give 185 mg of pale tan solid. MS: m/z=614.8 (M+1).

Step E:

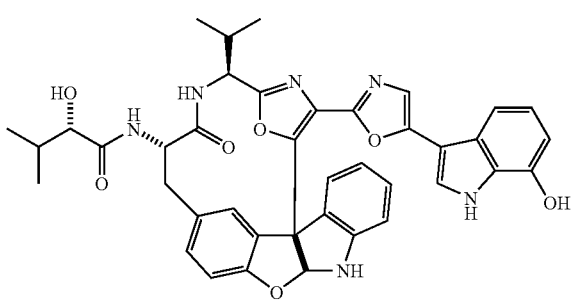

The coupling conditions for this reaction are similar to those described in Example 7. The compound synthesized in Step D above was served as the amine reactant, and (S)-2-hydroxy-3-methylbutyric acid was used in place of (S)-mandelic acid. MS: m/z=715.0 (M+1).

EXAMPLE 91

Step A:

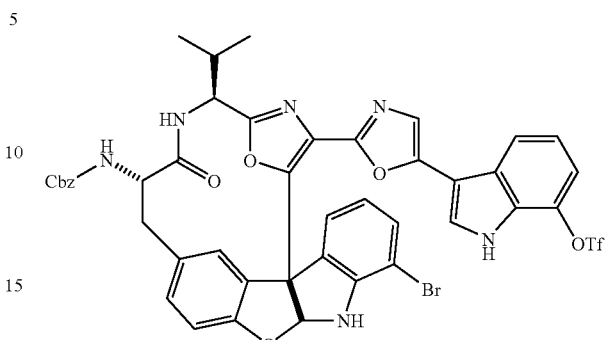

The compound synthesized in Step C of Example 90 (980 mg, 1.18 mmol) was dissolved in a mixture of CH$_2$Cl$_2$ (60 mL) and THF (6 mL) containing some 3A molecular sieve pellets. N,N-Diisopropylethylamine (0.62 mL, 460 mg, 3.56 mmol) was added and the mixture was cooled in an ice bath. A solution of triflic anhydride (0.22 mL, 370 mg, 1.3 mmol) in CH$_2$Cl$_2$ (7 mL) was added and the solution was stirred in the ice bath for 2 h. The reaction mixture was diluted with EtOAc (150 mL) and washed with 1 N aqueous HCl, saturated aqueous NaHCO$_3$, and saturated aqueous NaCl (50 mL of each). The organic layer was dried (Na$_2$SO$_4$), decanted and evaporated. The crude product was purified by flash column chromatography on silica gel, eluting with 7-60% EtOAc in CH$_2$Cl$_2$ to give 786 mg of product as a pale tan solid. MS: m/z=958.5 (M+1).

Step B:

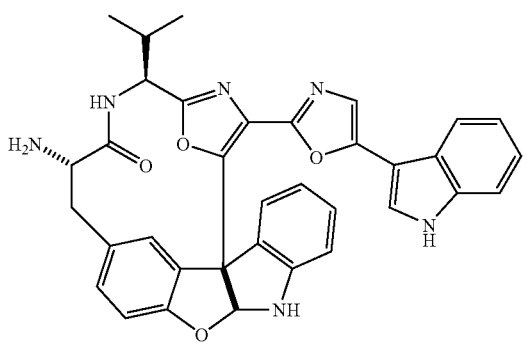

The compound synthesized in Step A above (786 mg, 0.819 mmol) was stirred with methanol (33 mL) and 10% palladium on carbon (78 mg) was added followed by diethylamine (0.400 mL, 283 mg, 3.87 mmol). The resulting suspension, which contained much undissolved starting material, was stirred overnight under an atmosphere of hydrogen. The mixture was then filtered through a plug of Celite, the catalyst was rinsed with ethanol, and the filtrate was evaporated. The crude product was combined with material similarly obtained from 54 mg of starting material and partitioned between EtOAc (75 mL) and saturated aqueous NaHCO$_3$ (20 mL), The organic layer was additional saturated aqueous NaHCO$_3$ (2×20 mL) and saturated aqueous NaCl (20 mL), dried (Na$_2$SO$_4$), decanted, and evaporated to give 503 mg of tan brittle glass. MS: m/z=598.8 (M+1).

Step C:

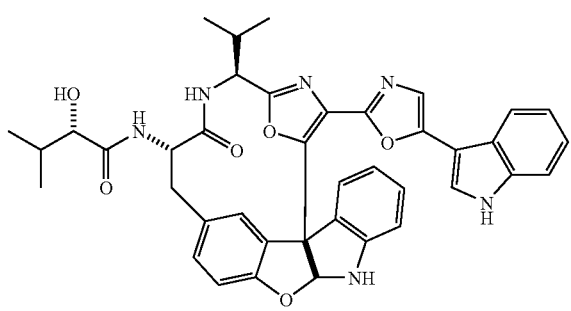

The coupling conditions for this reaction are similar to those described in Example 7. The compound synthesized in Step B above served as the amine reactant, and (S)-2-hydroxy-3-methylbutyric acid was used in place of (S)-mandelic acid. MS: m/z=699.2 (M+1).

EXAMPLE 92

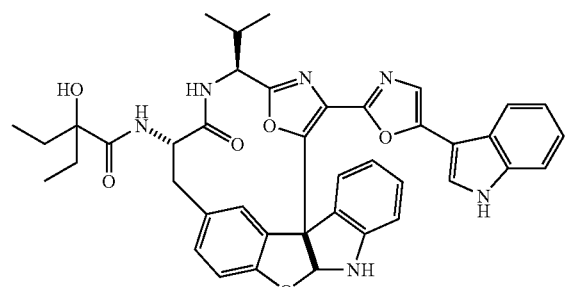

The compound synthesized in Step B of Example 91 (31 mg, 0.052 mmol) was dissolved in DMF (1.0 mL) with HOBt (8.1 mg, 0.060 mmol) and 2-ethyl-2-hydroxybutyric acid (7.9 mg, 0.060 mmol), Some 3A molecular sieve pellets were added, followed by EDC (13.5 mg, 0.071 mmol), and the mixture was stirred overnight at RT. The reaction mixture was then diluted into EtOAc (25 mL) and washed with 1 N aqueous HCl, saturated aqueous NaHCO$_3$, and saturated aqueous NaCl (10 mL of each). The organic layer was dried (Na$_2$SO$_4$), decanted, and evaporated. Purification by flash column chromatography on silica gel, eluting with 20% EtOAc in CH$_2$Cl$_2$, yielded the product as 16 mg of light tan powder. MS: m/z=713.2 (M+1).

EXAMPLE 93

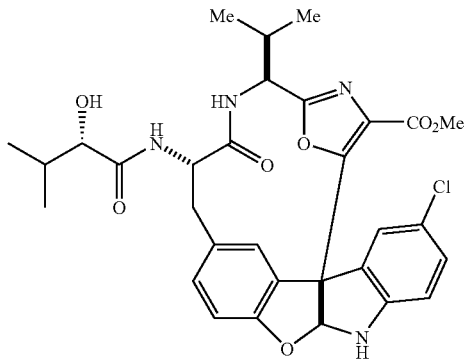

Chemical Formula: C$_{31}$H$_{33}$ClN$_4$O$_7$
Exact Mass: 608.20; Molecular Weight: 609.07

EXAMPLE 94

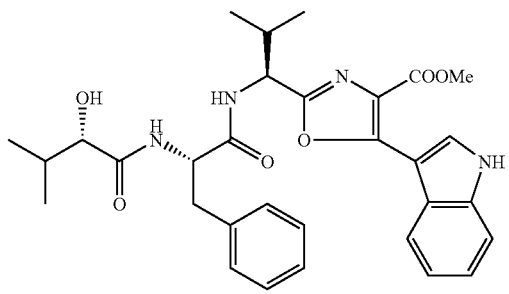

Chemical Formula: C$_{31}$H$_{36}$N$_4$O$_6$
Exact Mass: 560.26; Molecular Weight: 560.64

EXAMPLE 95

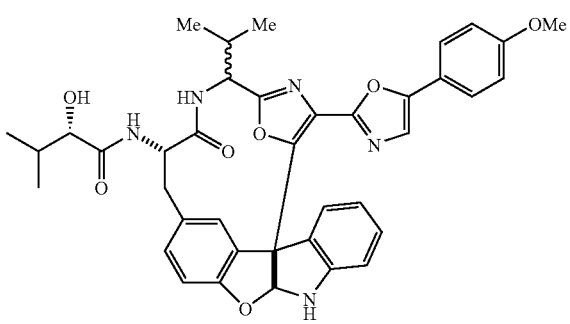

This compound was isolated as a by-product from Step D of Example 71. MS: m/z=689.8 (M+1).

EXAMPLE 96

Additional Compounds

The compounds shown in Table 1 are prepared by the methods described herein for structurally similar compounds.

TABLE 1

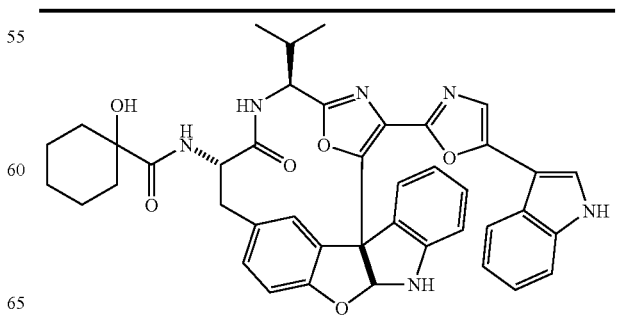

TABLE 1-continued
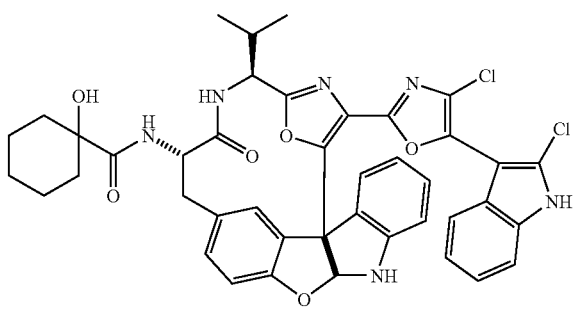
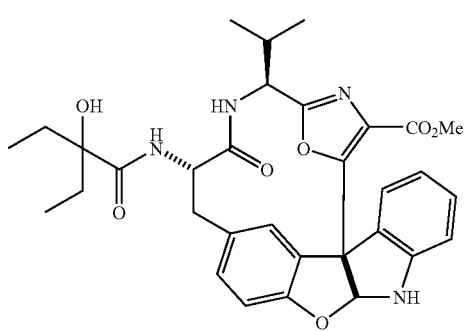
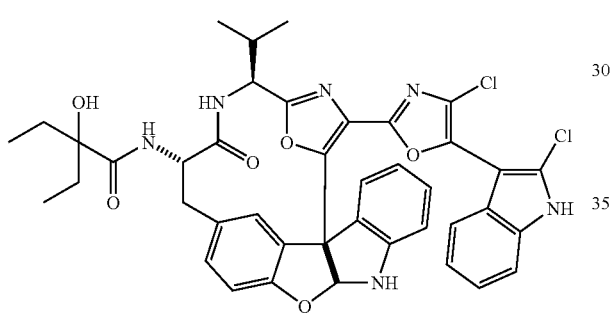
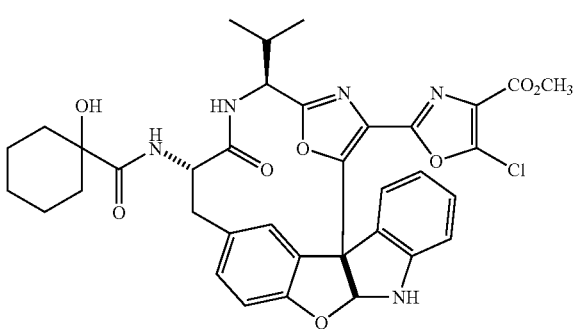
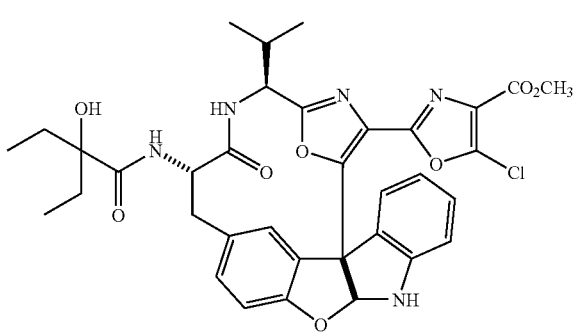
TABLE 1-continued
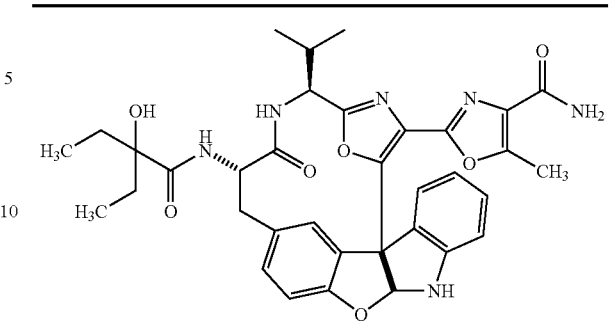
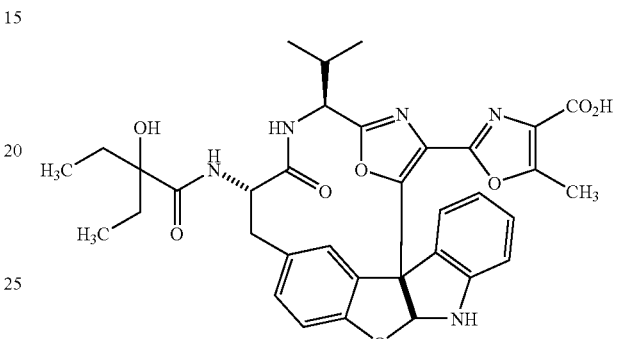
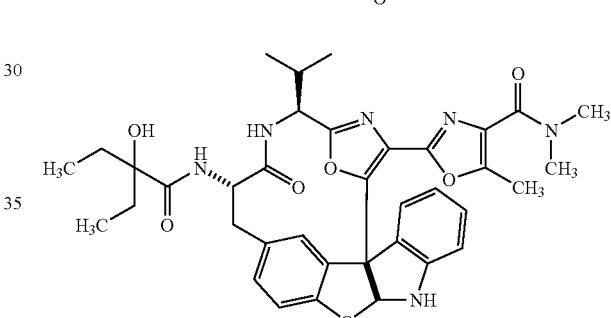
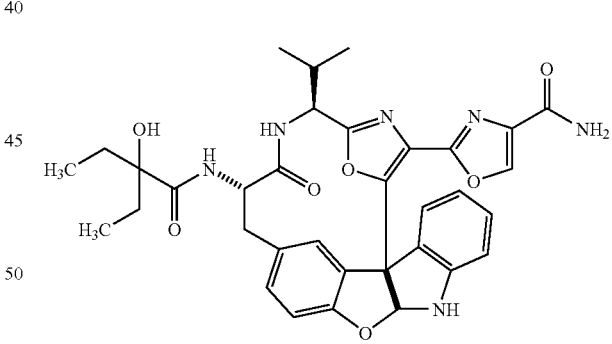
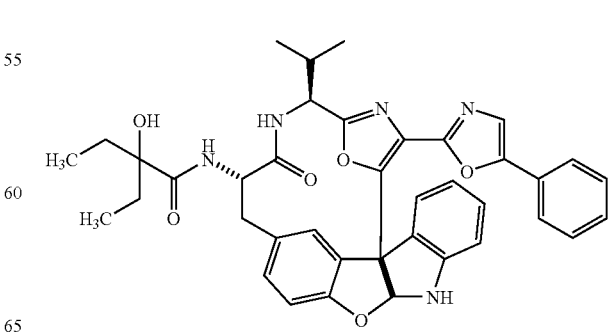

TABLE 1-continued
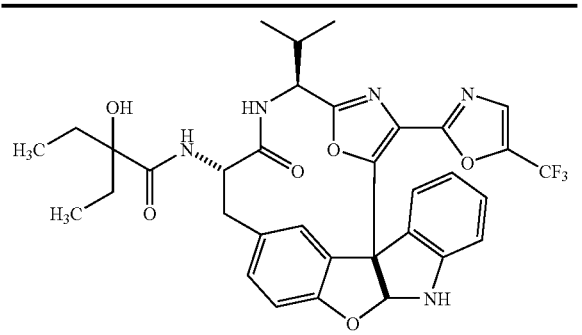
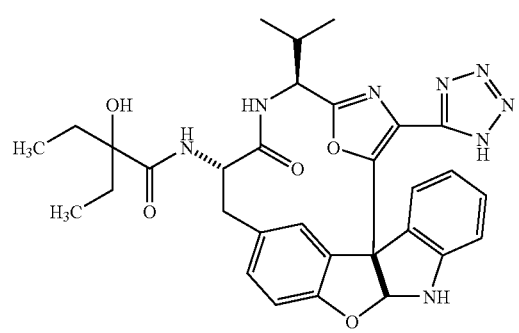
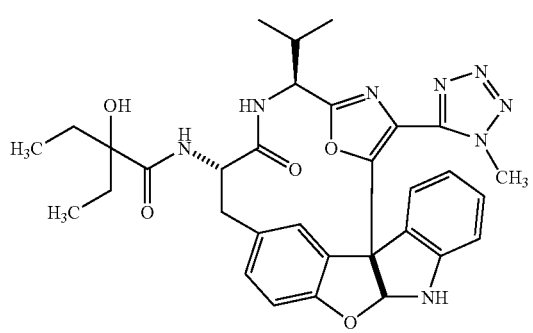
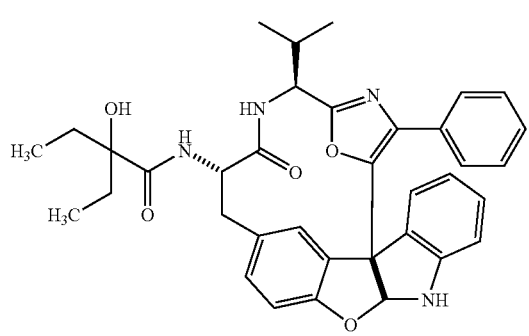
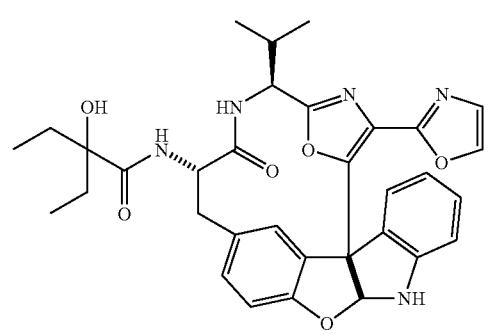
TABLE 1-continued
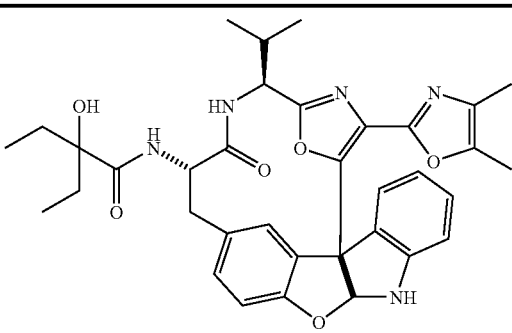
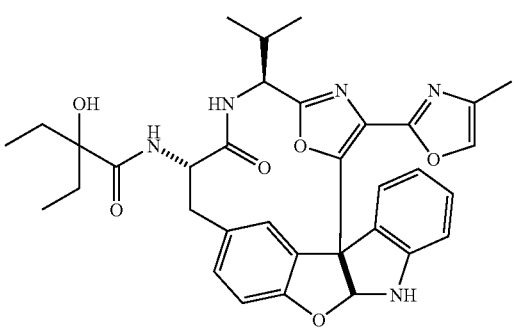
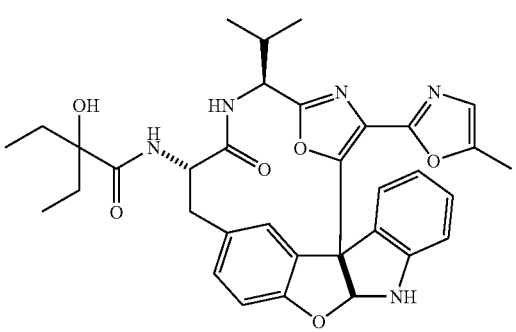
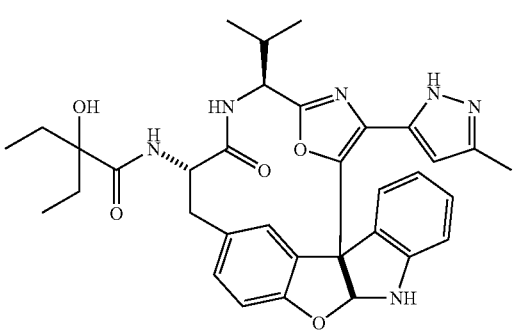
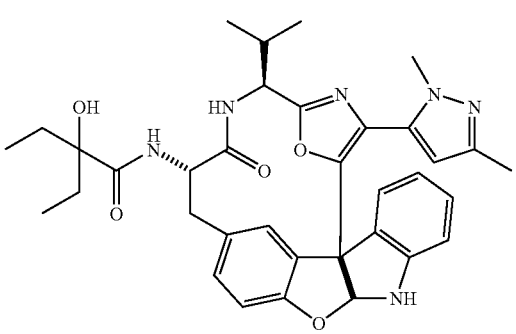

TABLE 1-continued

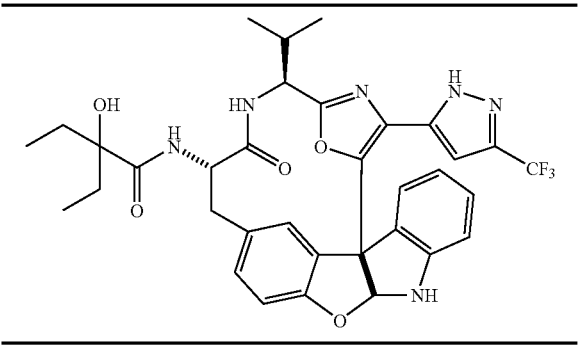

EXAMPLE 97

Cell Viability Assay Protocol

Cell viability assays were run using standard protocols known to those of skill in art. Cells were plated in 96 well plates at the density of 3,000-10,000 cells per well. Twenty four hours later, cells were treated with increasing concentration of test compounds (1 nM to 1 µM). After another 48 hour, cell survival was measured using CELL-TITER-GLO® reagent (Promega) following the protocol provided by the manufacture. The $IC_{50}$ value was determined as the concentration of test compound that kills 50% of the cell population.

EXAMPLE 98

Representative Biological Data

Cell viability data generated according to the protocol described in Example 97 was generated for representative compounds in A2058 and U937 cells. Data are provided below in Table 2.

A synthetic diazonamide analog ("Compound J") was used as a reference compound. Compound J has the structure:

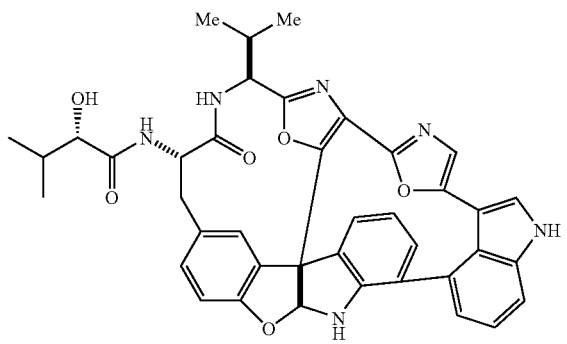

TABLE 2

| | Cell viability data in A2058 and U937 cells | |
|---|---|---|
| | $IC_{50}$ (µM) | |
| Ex. # | A2058 | U937 |
| Cpd J | 0.039 | 0.026 |
| 3 | >1 | >1 |
| 4 | >1 | >1 |

TABLE 2-continued

| | Cell viability data in A2058 and U937 cells | |
|---|---|---|
| | $IC_{50}$ (µM) | |
| Ex. # | A2058 | U937 |
| 6 | >1 | >1 |
| 7 | >1 | >1 |
| 8 | >1 | >1 |
| 9 | >1 | >1 |
| 10 | >1 | >1 |
| 11 | >1 | >1 |
| 12 | >1 | >1 |
| 13 | >1 | >1 |
| 14 | >1 | >1 |
| 15 | >1 | >1 |
| 16 | >1 | >1 |
| 17 | >1 | >1 |
| 18 | >1 | >1 |
| 19 | >1 | >1 |
| 20 | >1 | >1 |
| 21 | >1 | >1 |
| 22 | >1 | >1 |
| 23 | >1 | >1 |
| 24 | >1 | >1 |
| 25 | >1 | >1 |
| 26 | >1 | >1 |
| 27 | >1 | >1 |
| 28 | >1 | >1 |
| 29 | >1 | >1 |
| 30 | >1 | >1 |
| 31 | >1 | >1 |
| 32 | >1 | >1 |
| 33 | >1 | >1 |
| 34 | >1 | >1 |
| 35 | >1 | >1 |
| 36 | >1 | >1 |
| 37 | >1 | >1 |
| 38 | >1 | >1 |
| 39 | >1 | >1 |
| 40 | >1 | >1 |
| 41 | >1 | >1 |
| 42 | >1 | >1 |
| 43 | 0.533 | 0.697 |
| 44 | >1 | >1 |
| 45 | 0.329 | 0.185 |
| 46 | 0.044 | 0.013 |
| 47 | 0.077 | 0.019 |
| 48 | 0.058 | 0.039 |
| 49 | 0.049 | 0.040 |
| 50 | 0.075 | 0.040 |
| 51 | 0.056 | 0.040 |
| 52 | 0.108 | 0.028 |
| 53 | 0.357 | 0.068 |
| 54 | 0.164 | 0.063 |
| 55 | >1 | 0.900 |
| 56 | 0.841 | 0.736 |
| 57 | 0.313 | 0.111 |
| 58 | >1 | >1 |
| 59 | 0.514 | 0.604 |
| 60 | 0.636 | 0.562 |
| 61 | 0.883 | 0.793 |
| 62 | 0.243 | 0.192 |
| 63 | 0.247 | 0.162 |
| 64 | 0.184 | 0.184 |
| 65 | 0.553 | 0.235 |
| 66 | 0.363 | 0.218 |
| 67 | 0.047 | 0.024 |
| 68 | 0.066 | 0.057 |
| 69 | 0.170 | 0.081 |
| 70 | 0.080 | 0.065 |
| 71 | 0.639 | >1 |
| 72 | >1 | >1 |
| 73 | 0.093 | 0.037 |
| 74 | 0.292 | 0.110 |
| 75 | 0.226 | 0.229 |
| 76 | 0.114 | 0.127 |
| 77 | 0.080 | 0.018 |
| 78 | 0.154 | 0.052 |
| 79 | 0.174 | 0.071 |

TABLE 2-continued

Cell viability data in A2058 and U937 cells

| Ex. # | IC$_{50}$ (μM) A2058 | U937 |
|---|---|---|
| 80 | 0.021 | 0.0013 |
| 81 | 0.006 | 0.0014 |
| 82 | 0.126 | 0.066 |
| 83 | 0.433 | 0.252 |
| 84 | 0.487 | 0.315 |
| 85 | 0.337 | 0.234 |
| 86 | 0.179 | 0.064 |
| 87 | 0.479 | 0.164 |
| 88 | >1 | 0.700 |
| 89 | >1 | >1 |
| 90 | 0.994 | >1 |
| 91 | 0.475 | 0.579 |
| 93 | >1 | >1 |
| 94 | >1 | >1 |
| 95 | >1 | >1 |

EXAMPLE 99

Cell Profiling Data

The compound of Example 46 was profiled in tumor cell lines derived from a variety of origins. Data are provided in Table 3.

TABLE 3

Cell Profiling Data for Example 46

| Tumor Cell Line | Origin | IC$_{50}$ (μM) |
|---|---|---|
| U937 | Blood | 0.013 |
| BT474 | Breast | 0.006 |
| COLO205 | Colon | 0.147 |
| HCT116 | Colon | 0.731 |
| HT29 | Colon | 0.090 |
| LOVO | Colon | 0.148 |
| HCC1437 | Lung | 0.063 |
| HCC461 | Lung | 0.344 |
| NCI-H460 | Lung | 0.245 |
| OVCAR 3 | Ovarian | 0.032 |
| BxPC3 | Pancreas | 0.023 |
| DU145 | Prostate | 0.067 |
| A2058 | Skin | 0.044 |
| A375 | Skin | 0.099 |

EXAMPLE 100

Xenograft Tumor Models

The compound of Example 73 was tested in HCT116 human colon carcinoma xenograft and Miapaca pancreatic cancer xenograft tumor models in 5- to 6-week-old Harlan Athymic Nude-Foxn1nu mice.

Protocol:

Preparation of Tumor Cells

1. Tumor cells were cultured in complete RPMI medium and excluded any contamination
2. When cells are 70-80% confluent, medium was removed and cells were washed with serum free media, trypsinized, harvested and washed with serum free media for three times by centrifuge. After final washing, cells were counted and mixed with matrigel at 1:1 ration in volume. Cells were suspended in a volume that 200 μl contains required number of cells per injection.

Preparation of the Injection

1. Clean and sterilize the inoculation area of the mice with iodine solutions and ethanol.
2. Take cells with 1-cc syringe.
3. Inject tumor cells (1×10$^7$) subcutaneously (s.c.) into the lower flank of the mice.
4. When tumors reached 200-300 mm$^3$ in size, mice were randomized into treatment groups of five mice per group.
5. Mice were weighed and tumors measured using vernier calipers two times per week. Tumor volume in mm3 is calculated by the formula:

Volume (mm$^3$)=(length×width$^2$)/2.

Treatment

The compound of Example 73 was dissolved in cremophor/ethanol (1:1) at 20 mg/mL as the stock solution and then diluted in saline to 2.5 mg/mL. The compound and the vehicle (6.25% cremophor/6.25% ethanol in saline) were administered intravenously in a total volume of 0.2 mL three times a week for total six treatments.

In the HCT116 colon cancer xenograft model, animals were injected on days 9, 11, 14, 16, 18 and 21 post tumor-cell injection.

In the Miapaca pancreatic cancer xenograft model, animals were injected on days 6, 8, 11, 13, 15, and 18 post tumor-cell injection.

Results

The activity of Example 73 at 20 mpk in HCT 116 colon carcinoma xenograft model is provided in FIG. 1.

Figure 2:
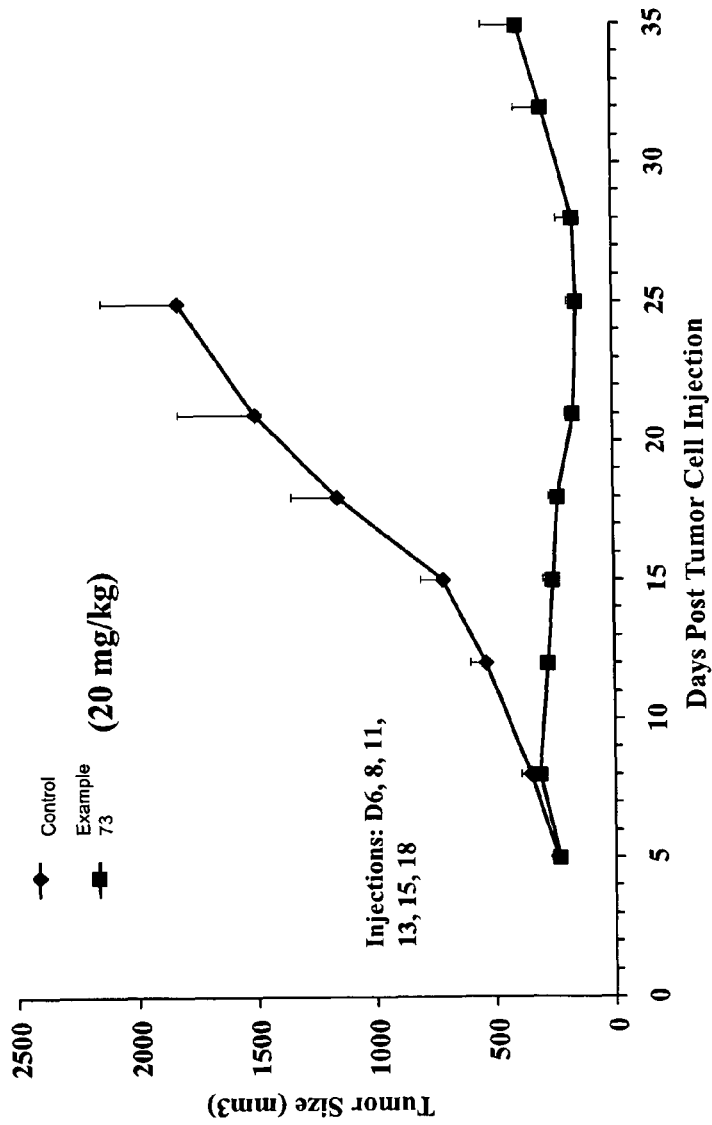
FIG. 2 shows data for compound of Example 73 in a Miapaca pancreatic cancer xenograft model in mice. The compound of Example 73 was administered at 20 mg/kg per dose. Injections were given at days 6, 8, 11, 13, 15 and 18 post tumor cell injection.

The activity of Example 73 at 20 mpk in Miapaca pancreatic cancer xenograft model is provided in FIG. 2.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

The invention claimed is:

1. A compound of formula (I):

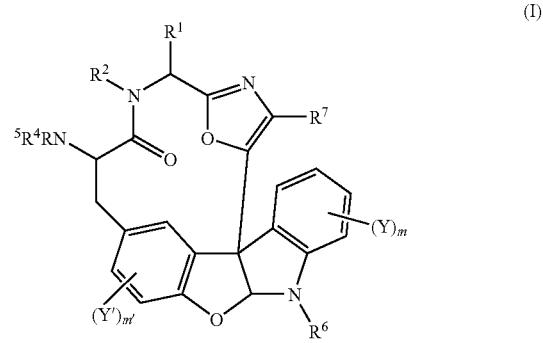

or a pharmaceutically acceptable salt,
wherein R$^1$ is H, or C1-C8 alkyl, C2-C8 alkenyl, C2-C8 alkynyl, C1-C8 heteroalkyl, C2-C8 heteroalkenyl, C2-C8 heteroalkynyl, C6-C12 aryl, C7-C14 arylalkyl, C5-C12 heteroaryl, or C6-C14 heteroarylalkyl, each of which may be optionally substituted;

$R^2$ is H, or C1-C8 alkyl, C1-C8 heteroalkyl, C7-C14 arylalkyl, C6-C14 heteroarylalkyl, each of which may be optionally substituted; or $R^1$ and $R^2$ may be taken together with the atoms to which they are attached to form an optionally substituted pyrrolidine, piperidine, homopiperidine, morpholine, thiomorpholine, piperazine, or homopiperazine;

$R^4$ is H, or C1-C4 alkyl;

$R^5$ is H, or C1-C8 alkyl, C2-C12 alkenyl, C3-C8 cycloalkyl, C4-C12 cycloalkylalkyl, C2-C12 alkynyl, C6-C12 aryl, C7-C14 arylalkyl, C5-C12 heteroaryl, C6-C14 heteroarylalkyl, alkylsulfonyl, or arylsulfonyl, or a heteroform of one of these, each of which may be optionally substituted; or $R^5$ is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or $R^4$ and $R^5$ may be taken together with nitrogen to form an optionally substituted 3- to 8-membered azacyclic ring, which may be saturated, unsaturated or aromatic, optionally containing an additional heteroatom as a ring member;

$R^6$ is H, or C1-C8 alkyl, C1-C8 heteroalkyl, C7-C14 arylalkyl, C6-C14 heteroarylalkyl, C1-C6 acyl, C6-C12 aroyl, alkylsulfonyl, or arylsulfonyl, each of which may be optionally substituted;

$R^7$ is an optionally substituted C6-C12 aryl, optionally substituted C5-C12 heteroaryl, or optionally substituted C5-C12 heterocyclyl ring;

m is 0-4;

m' is 0-3; and each Y and Y' is independently halo, OH, C1-C4 alkoxy, or C1-C8 alkyl, C2-C8 alkenyl, C2-C8 alkynyl, C6-C12 aryl, or C7-C14 arylalkyl, or a heteroform of one of these, each of which may be optionally substituted, wherein the term substituted is limited to the following substitutions:

when present on an alkyl, alkenyl, alkynyl or a heteroform thereof, the substitution is halo, OH, =O, =N—CN, =N—OR, =NR, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR', =NR', OR', NR'$_2$, SR', SOR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, optionally fluorinated C1-C8 alkyl, C2-C8 heteroalkyl, C1-C8 acyl, C2-C8 heteroacyl, C6-C12 aryl , C5-C12 heteroaryl, C5-C20 arylalkyl, or C5-C20 heteroarylalkyl;

when present on aryl or heteroaryl the substitution is halo, OH, OR, CH$_2$OH, CH$_2$OR, CH$_2$NR$_2$, NR$_2$, SR, SOR, SO$_2$R, SO$_2$NR$_2$, NRSO$_2$R, NRCONR$_2$, NRCOOR, NRCOR, CN, COOR, CONR$_2$, OOCR, C(O)R, and NO$_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as for alkyl; and when present on an arylalkyl or heteroarylalkyl the substitution is as alkyl if on an alkyl or heteroalkyl portion, and is aryl if on an aryl or heteroaryl portion;

wherein each of said heteroalkyl, heteroalkenyl, heteroalkynyl, heteroaryl, heteroarylalkyl and heterocyclyl, and heteroform contain one or two backbone heteroatoms selected from O, S and N and combinations thereof; and wherein cycloalkyl is a saturated or partially saturated, monocyclic or fused or spiro polycyclic, carbocycle that is connected via a ring carbon atom, cycloalkylalkyl is a carbocyclic non-aromatic group that is connected via an alkyl linker, heterocyclyl is a non-aromatic cyclic group that contains at least one heteroatom as a ring member and that is connected via a ring atom of the cyclic group, which may be C or N; and heterocyclylalkyl a heterocyclyl that is connected via an alkyl.

2. The compound of claim 1, having the formula:

(III)

or a pharmaceutically acceptable salt, wherein $R^1$ is H, or C1-C8 alkyl, C2-C8 alkenyl, C2-C8 alkynyl, C1-C8 heteroalkyl, C2-C8 heteroalkenyl, C2-C8 heteroalkynyl, C6-C12 aryl, C7-C14 arylalkyl, C5-C12 heteroaryl, or C6-C14 heteroarylalkyl, each of which may be optionally substituted;

$R^2$ is H, or C1-C8 alkyl, C1-C8 heteroalkyl, C7-C14 arylalkyl, C6-C14 heteroarylalkyl, each of which may be optionally substituted; or $R^1$ and $R^2$ may be taken together with the atoms to which they are attached to form an optionally substituted pyrrolidine, piperidine, homopiperidine, morpholine, thiomorpholine, piperazine, or homopiperazine;

$R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted;

$R^6$ is H, or C1-C8 alkyl, C1-C8 heteroalkyl, C7-C14 arylalkyl, C6-C14 heteroarylalkyl, C1-C6 acyl, C6-C12 aroyl, alkylsulfonyl, or arylsulfonyl, each of which may be optionally substituted;

$R^7$ is an optionally substituted C6-C12 aryl, optionally substituted C5-C12 heteroaryl, or optionally substituted C5-C12 heterocyclyl ring;

m is 0-4; and each Y is independently halo, OH, C1-C4 alkoxy, or C1-C8 alkyl, C2-C8 alkenyl, C2-C8 alkynyl, C6-C12 aryl, or C7-C14 arylalkyl, or a heteroform of one of these, each of which may be optionally substituted, wherein the term substituted is limited to the following substitutions:

when present on an alkyl, alkenyl, alkynyl or a heteroform thereof, the substitution is halo, OH, =O, =N—CN, =N—OR, =NR, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR', =NR', OR', NR'$_2$, SR', SOR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, optionally fluorinated C1-C8 alkyl, C2-C8 heteroalkyl, C1-C8 acyl, C2-C8 heteroacyl, C6-C12 aryl, C5-C12 heteroaryl, C5-C20 arylalkyl, or C5-C20 heteroarylalkyl;

when present on aryl or heteroaryl the substitution is halo, OH, OR, CH$_2$OH, CH$_2$OR, CH$_2$NR$_2$, NR$_2$, SR, SOR, SO$_2$R, SO$_2$NR$_2$, NRSO$_2$R, NRCONR$_2$, NRCOOR, NRCOR, CN, COOR, CONR$_2$, OOCR, C(O)R, and NO$_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as for alkyl; and when present on an arylalkyl or heteroarylalkyl the substitution is as alkyl if on an alkyl or heteroalkyl portion, and is aryl if on an aryl or heteroaryl portion;

wherein each of said heteroalkyl, heteroalkenyl, heteroalkynyl, heteroaryl, heteroarylalkyl and heterocyclyl, and heteroform contain one or two backbone heteroatoms selected from O, S and N and combinations thereof; and wherein cycloalkyl is a saturated or partially saturated, monocyclic or fused or spiro polycyclic, carbocycle that is connected via a ring carbon atom, cycloalkylalkyl is a carbocyclic non-aromatic group that is connected via an alkyl linker, heterocyclyl is a non-aromatic cyclic group that contains at least one heteroatom as a ring member and that is connected via a ring atom of the cyclic group, which may be C or N; and heterocyclylalkyl a heterocyclyl that is connected via an alkyl.

3. The compound of claim 1, wherein R$^7$ is an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole, or tetrazole ring; or an optionally substituted phenyl, naphthyl, benzimidazole, benzoxazole, benzthiazole, pyridinyl, pyrimidinyl, pyrazinyl or pyridazinyl ring.

4. A compound of formula (V) or formula (VI):

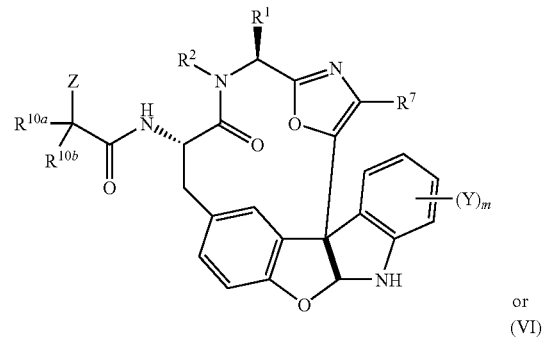

(V)

or

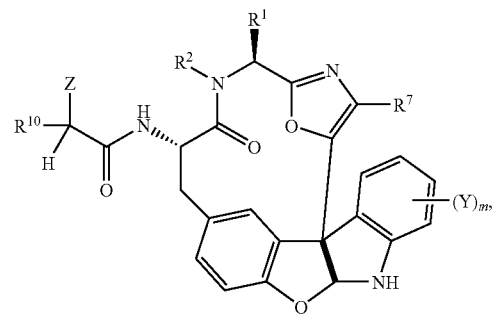

(VI)

or a pharmaceutically acceptable salt;

wherein R$^1$ is H, or C1-C8 alkyl, C2-C8 alkenyl, C2-C8 alkynyl, C1-C8 heteroalkyl, C2-C8 heteroalkenyl, C2-C8 heteroalkynyl, C6-C12 aryl, C7-C14 arylalkyl, C5-C12 heteroaryl, or C6-C14 heteroarylalkyl, each of which may be optionally substituted;

R$^2$ is H, or C1-C8 alkyl, C1-C8 heteroalkyl, C7-C14 arylalkyl, C6-C14 heteroarylalkyl, each of which may be optionally substituted; or R$^1$ and R$^2$ may be taken together with the atoms to which they are attached to form an optionally substituted pyrrolidine, piperidine, homopiperidine, morpholine, thiomorpholine, piperazine, or homopiperazine;

R$^7$ is an optionally substituted C6-C12 aryl, optionally substituted C5-C12 heteroaryl, or optionally substituted C5-C12 heterocyclyl ring;

m is 0-4;

each Y is independently halo, OH, C1-C4 alkoxy, or C1-C8 alkyl, C2-C8 alkenyl, C2-C8 alkynyl, C6-C12 aryl, or C7-C14 arylalkyl, or a heteroform of one of these, each of which may be optionally substituted;

Z is OH, OR, CH$_2$OR, SR, and NR$_2$, where each R is independently H, optionally fluorinated C1-C4 alkyl, or optionally fluorinated C1-C4 acyl; and each of R$^{10}$, R$^{10a}$ and R$^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C14 arylalkyl, or a heteroform of one of these, each of which may be optionally substituted; or R$^{10a}$ and R$^{10b}$ may be taken together with the carbon to which they are attached to form a C3-C8 cycloalkyl or a C3-C8 heterocyclyl ring, which may be optionally substituted, wherein the term substituted is limited to the following substitutions:

when present on an alkyl, alkenyl, alkynyl or a heteroform thereof, the substitution is halo, OH, =O, =N—CN, =N—OR, =NR, OR, NR$_2$, SR, SOR, SO$_2$R, SO$_2$NR$_2$, NRSO₂R, NRCONR₂, NRCOOR, NRCOR, CN, COOR, CONR₂, OOCR, COR, and NO₂, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR', =NR', OR', NR'₂, SR', SOR', SO₂R', SO₂NR'₂, NR'SO₂R', NR'CONR'₂, NR'COOR', NR'COR', CN, COOR', CONR'₂, OOCR', COR', and NO₂, wherein each R' is independently H, optionally fluorinated C1-C8 alkyl, C2-C8 heteroalkyl, C1-C8 acyl, C2-C8 heteroacyl, C6-C12 aryl, C5-C12 heteroaryl, C5-C20 arylalkyl, or C5-C20 heteroarylalkyl;

when present on aryl or heteroaryl the substitution is halo, OH, OR, CH₂OH, CH₂OR, CH₇NR₂, NR₂, SR, SOR, SO₂R, SO₂NR₂, NRSO₂R, NRCONR₂, NRCOOR, NRCOR, CN, COOR, CONR₂, OOCR, C(O)R, and NO₂, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as for alkyl; and when present on an arylalkyl or heteroarylalkyl the substitution is as alkyl if on an alkyl or heteroalkyl portion, and is aryl if on an aryl or heteroaryl portion;

wherein each of said heteroalkyl, heteroalkenyl, heteroalkynyl, heteroaryl, heteroarylalkyl and heterocyclyl, and heteroform contain one or two backbone heteroatoms selected from O, S and N and combinations thereof; and wherein cycloalkyl is a saturated or partially saturated, monocyclic or fused or spiro polycyclic, carbocycle that is connected via a ring carbon atom, cycloalkylalkyl is a carbocyclic non-aromatic group that is connected via an alkyl linker, heterocyclyl is a non-aromatic cyclic group that contains at least one heteroatom as a ring member and that is connected via a ring atom of the cyclic group, which may be C or N; and heterocyclylalkyl a heterocyclyl that is connected via an alkyl.

5. The compound of claim 4, wherein $R^7$ is an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole, or tetrazole ring; or an optionally substituted phenyl, naphthyl, benzimidazole, benzoxazole, benzthiazole, pyridinyl, pyrimidinyl, pyrazinyl or pyridazinyl ring.

6. The compound of claim 4, wherein $R^7$ is an optionally substituted heterocyclic or heteroaromatic ring of the formula:

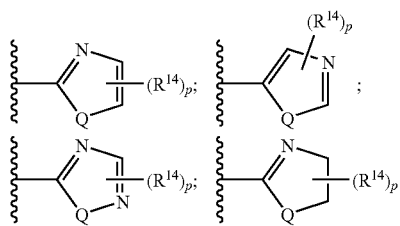

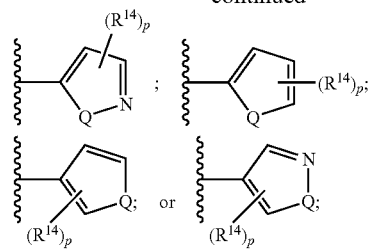

wherein Q is O, S or $NR^{13}$, where $R^{13}$ is H or C1-C4 alkyl;
each $R^{14}$ is independently halo, nitro, cyano, or optionally fluorinated C1-C4 alkyl, optionally fluorinated C1-C4 alkoxy, $COOR^{8'}$, $CONR^{9'}{}_2$, C6-C12 aryl or C5-C12 heteroaryl, each of which may be optionally substituted;
where $R^{8'}$ is H, or C1-C8 alkyl, C2-C8 alkenyl, C6-C12 aryl, or C7-C14 arylalkyl, or a heteroform of one of these, each of which may be optionally substituted; and
each $R^{9'}$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^{9'}$ on the same N can cyclize to form an optionally substituted 3- to 8-membered azacyclic ring, which may be saturated, unsaturated or aromatic, optionally containing an additional heteroatom selected from N, O, and S as a ring member;
p is 0-3; and
q is 0 to 4.

7. The compound of claim 4, having the formula:

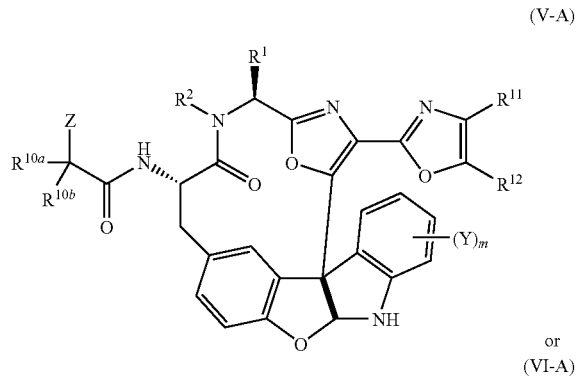

(V-A)

or (VI-A)

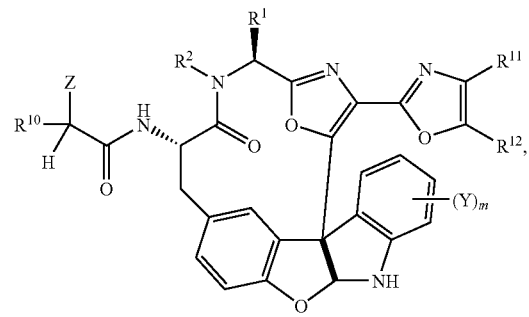

or a pharmaceutically acceptable salt;
wherein $R^1$, $R^2$, $R^{10a}$, $R^{10b}$, Y and m are as defined for compounds V and VI in claim 4;

wherein each of R[11] and R[12] is independently H, halo, nitro, cyano, or optionally fluorinated C1-C4 alkyl, optionally fluorinated C1-C4 alkoxy, COOR[8'], CONR[9']$_2$, C6-C12 aryl or C5-C12 heteroaryl, each of which may be optionally substituted;

where R[8'] is H, or C1-C8 alkyl, C2-C8 alkenyl, C6-C12 aryl, or C7-C14 arylalkyl, or a heteroform of one of these, each of which may be optionally substituted; and each R[9'] is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two R[9'] on the same N can cyclize to form an optionally substituted 3- to 8-membered azacyclic ring, which may be saturated, unsaturated or aromatic, optionally containing an additional heteroatom selected from N, O, and S as a ring member, wherein the term substituted is limited to the following substitutions:

when present on an alkyl, alkenyl, alkynyl or a heteroform thereof, the substitution is halo, OH, =O, =N—CN, =N—OR, =NR, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR', =NR', OR', NR'$_2$, SR', SOR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, optionally fluorinated C1-C8 alkyl, C2-C8 heteroalkyl, C1-C8 acyl, C2-C8 heteroacyl, C6-C12 aryl, C5-C12 heteroaryl, C5-C20 arylalkyl, or C5-C20 heteroarylalkyl;

when present on aryl or heteroaryl the substitution is halo, OH, OR, CH$_2$OH CH$_2$OR, CH$_2$NR$_2$, NR$_2$, SR, SOR, SO$_2$R, SO$_2$NR$_2$, NRSO$_2$R, NRCONR$_2$, NRCOOR, NRCOR, CN, COOR, CONR$_2$, OOCR, C(O)R, and NO$_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as for alkyl; and when present on an arylalkyl or heteroarylalkyl the substitution is as alkyl if on an alkyl or heteroalkyl portion, and is aryl if on an aryl or heteroaryl portion;

wherein each of said heteroalkyl, heteroalkenyl, heteroalkynyl, heteroaryl, heteroarylalkyl and heterocyclyl, and heteroform contain one or two backbone heteroatoms selected from O, S and N and combinations thereof; and wherein cycloalkyl is a saturated or partially saturated, monocyclic or fused or spiro polycyclic, carbocycle that is connected via a ring carbon atom, cycloalkylalkyl is a carbocyclic non-aromatic group that is connected via an alkyl linker, heterocyclyl is a non-aromatic cyclic group that contains at least one heteroatom as a ring member and that is connected via a ring atom of the cyclic group, which may be C or N; and heterocyclylalkyl a heterocyclyl that is connected via an alkyl.

8. The compound of claim 7, wherein R[12] is H.

9. The compound of claim 8, wherein R[11] is COOR[8'] or CONR[9']$_2$; or is C6-C12 aryl or C5-C12 heteroaryl, each of which may be optionally substituted.

10. The compound of claim 1 in the form of a pharmaceutically acceptable salt.

11. A pharmaceutical composition comprising the compound of claim 1 and at least one pharmaceutically acceptable excipient.

12. A compound selected from the group consisting of:

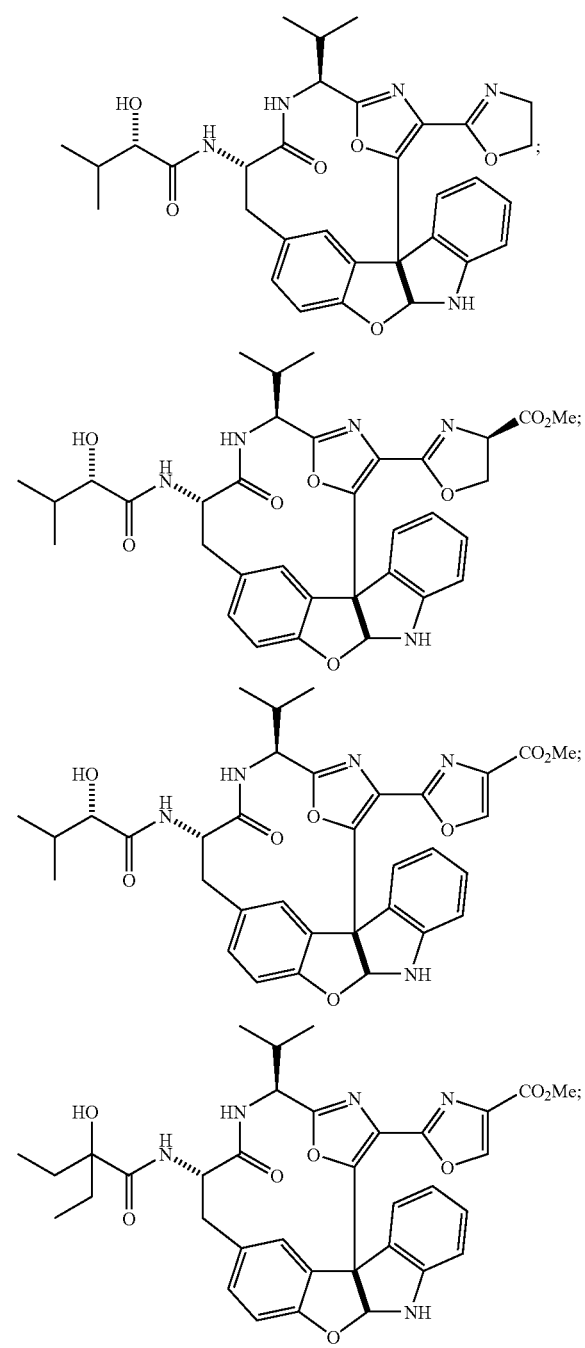

119
-continued
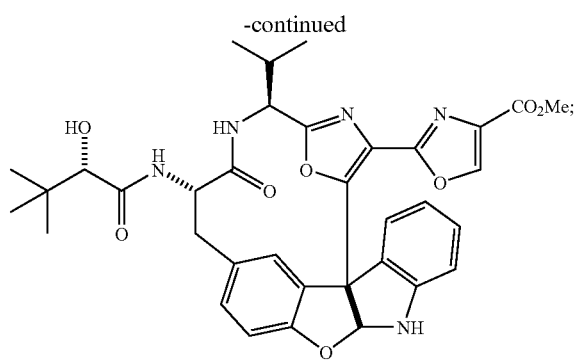
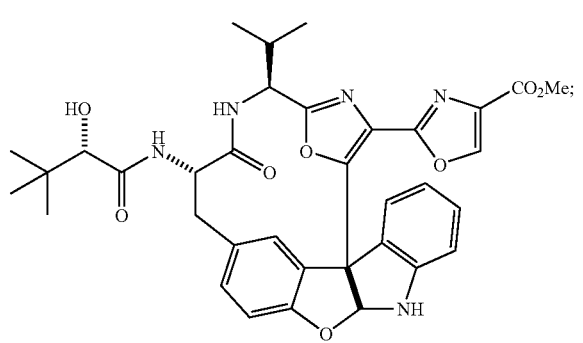
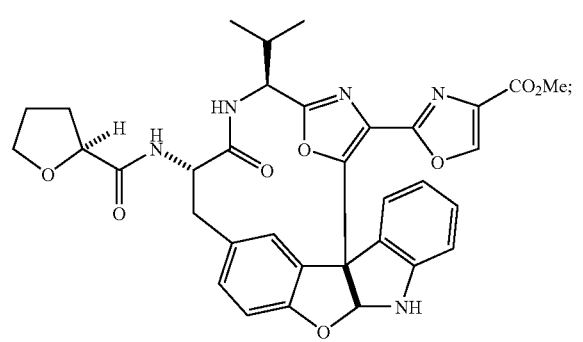
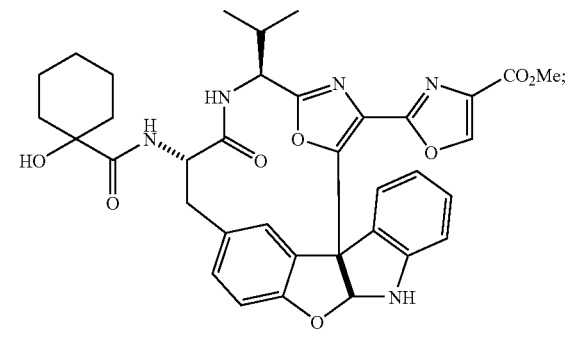
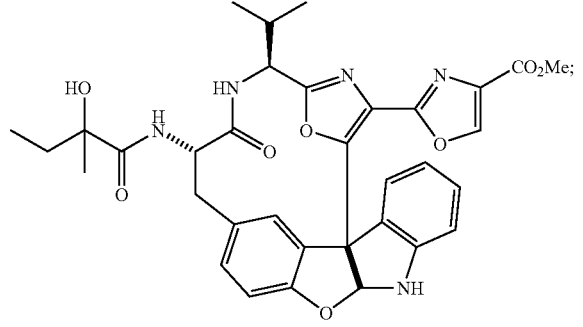
120
-continued
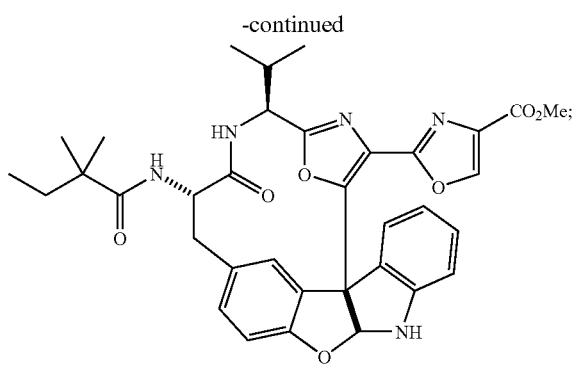
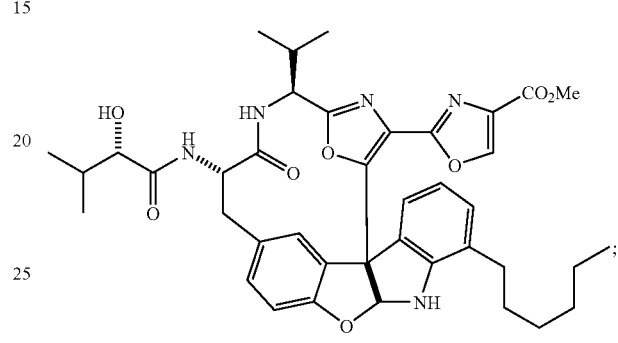
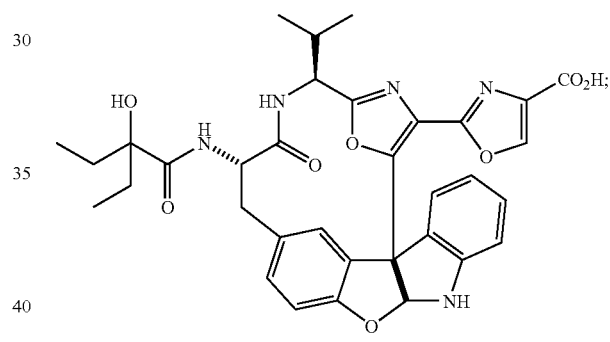
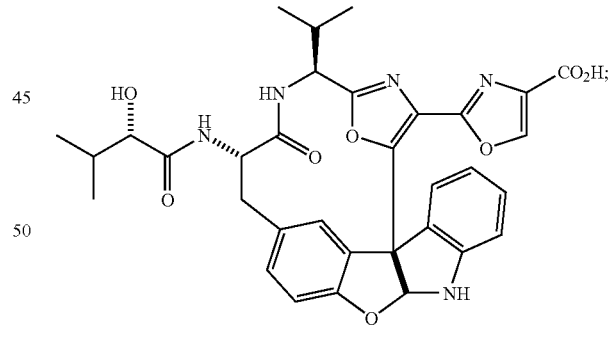
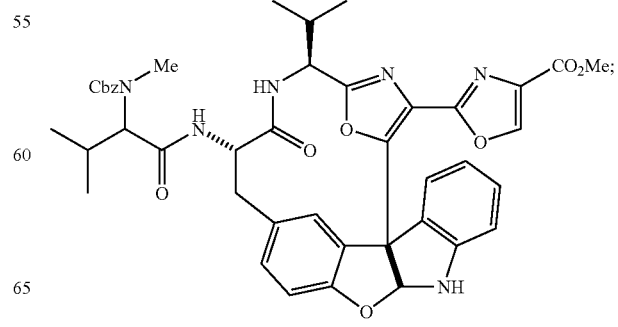

121
-continued
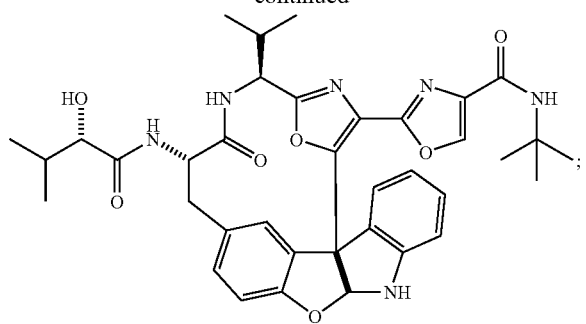
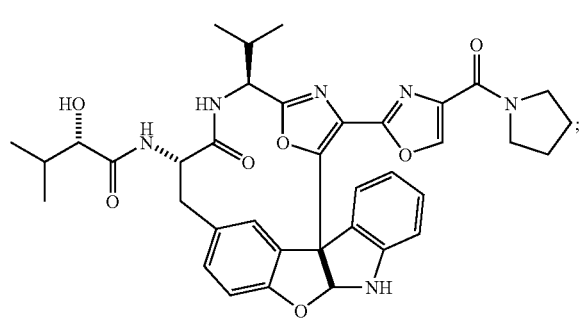
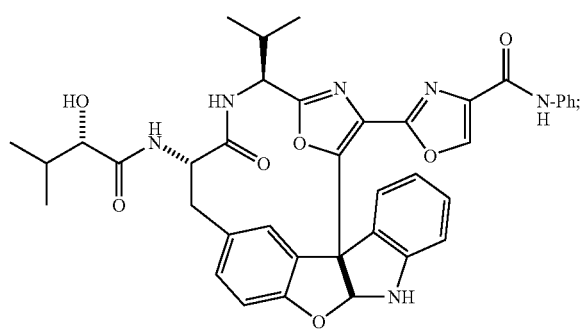
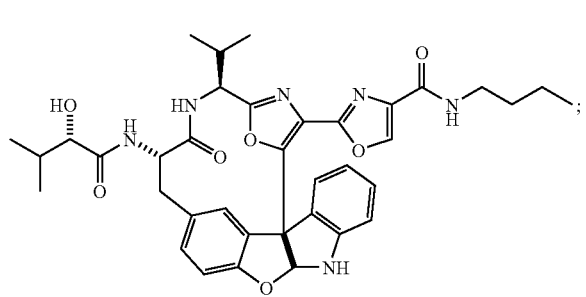
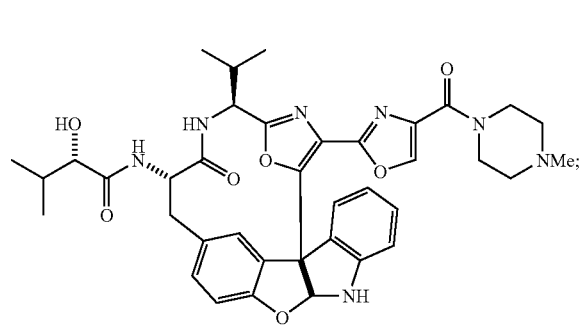
122
-continued
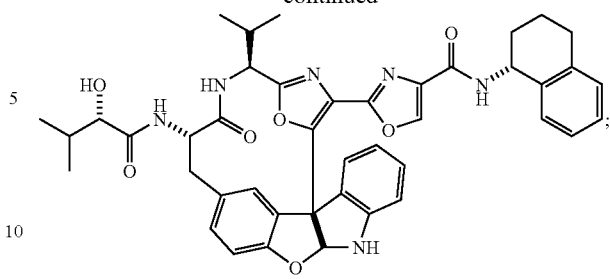
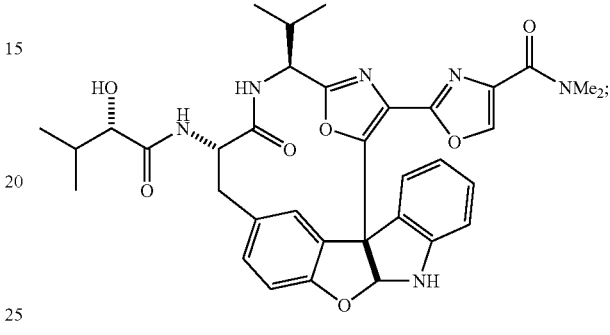
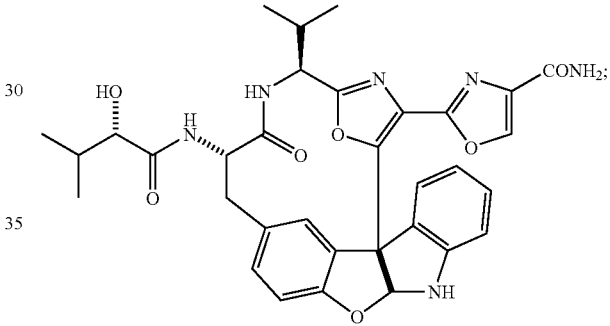
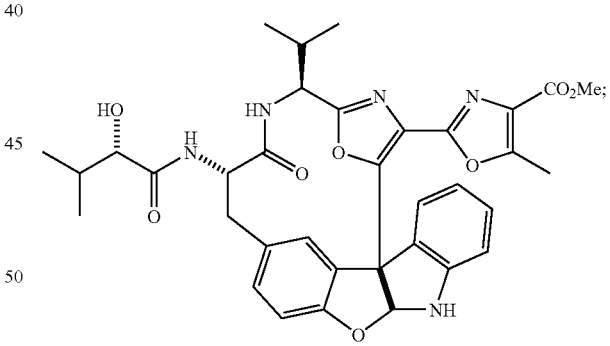
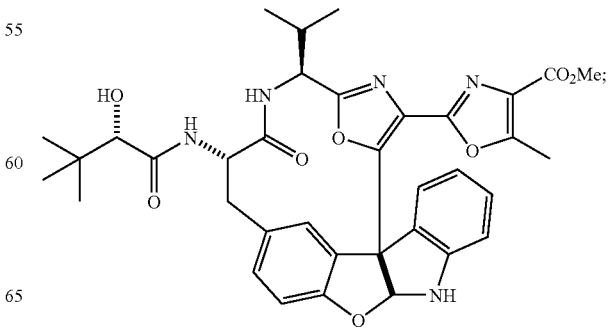

| 123 -continued | 124 -continued |
|---|---|
| 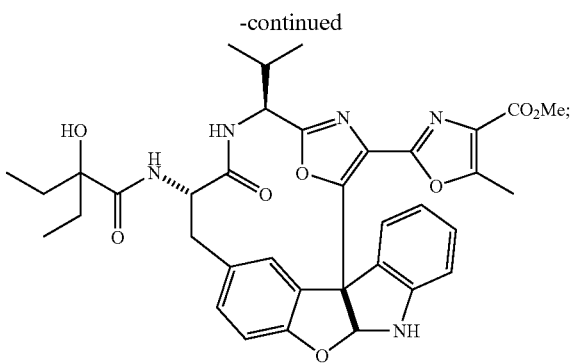 | 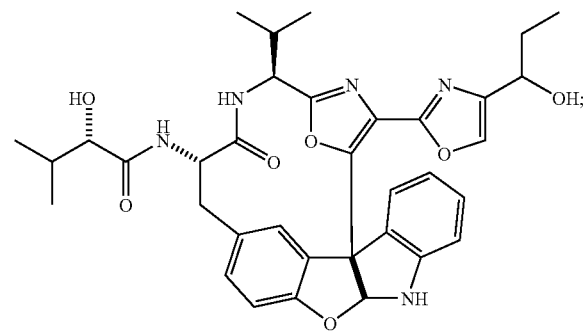 |
| 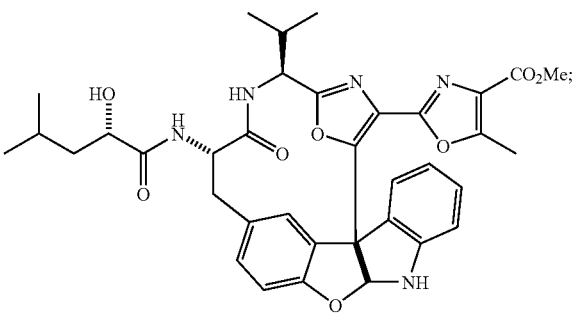 | 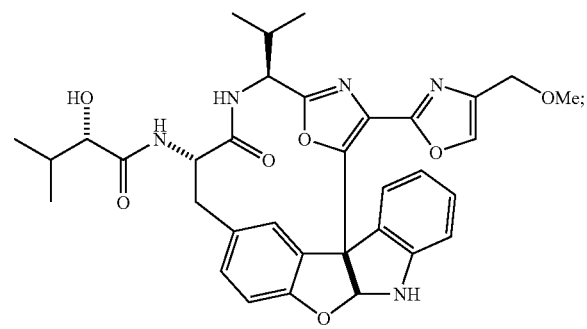 |
| 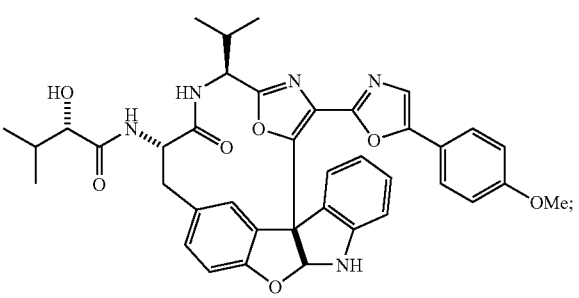 | 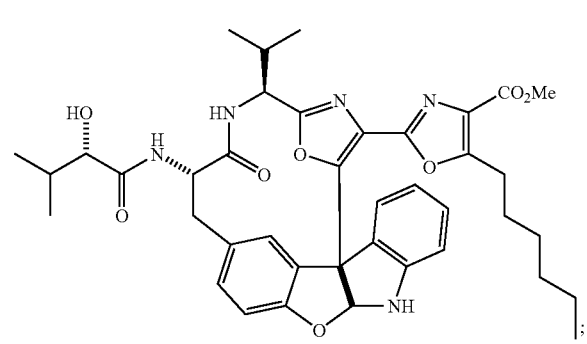 |
| 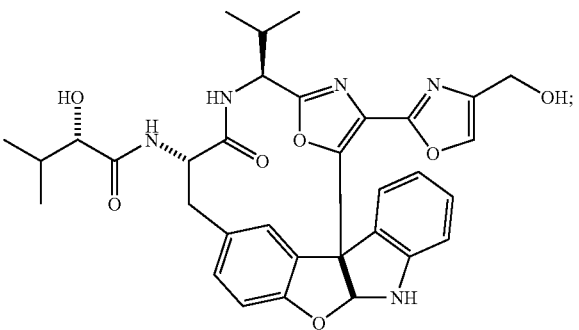 | 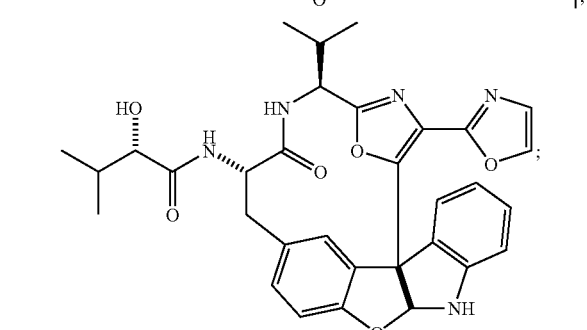 |
| 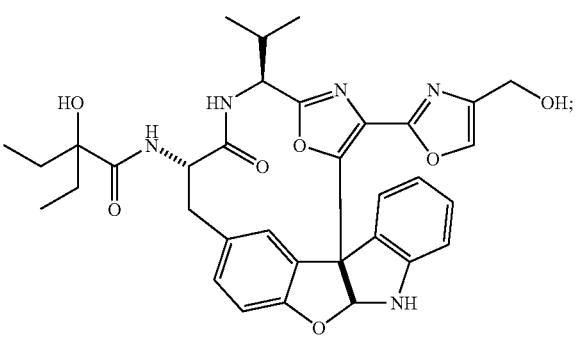 | 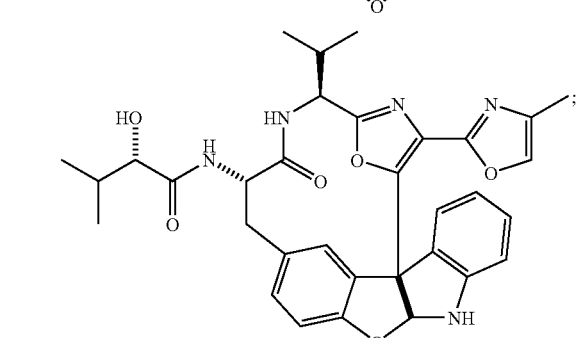 |

125
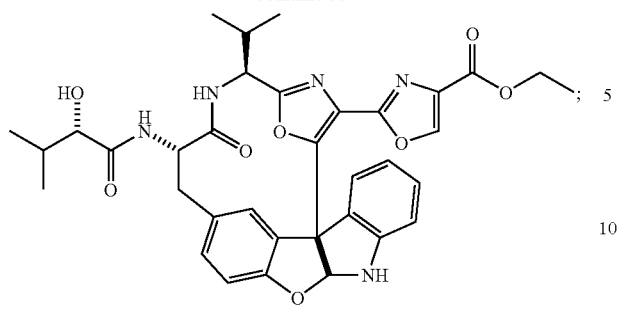
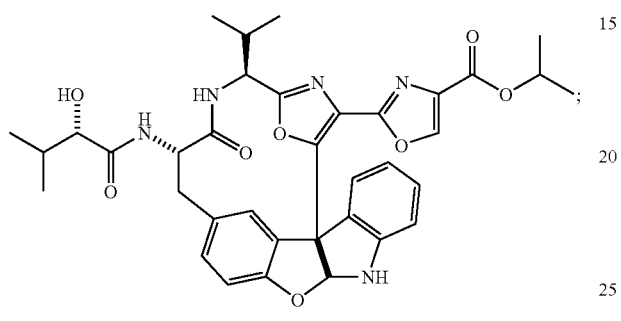
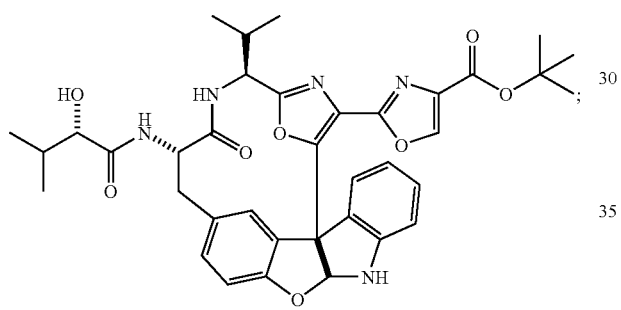
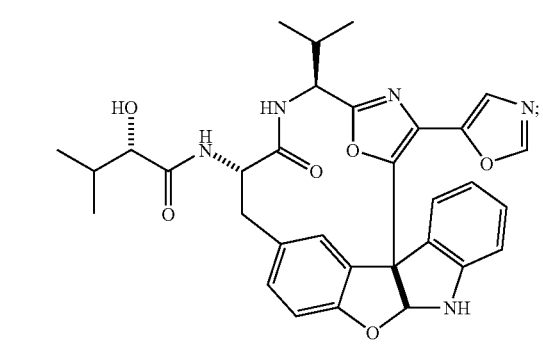
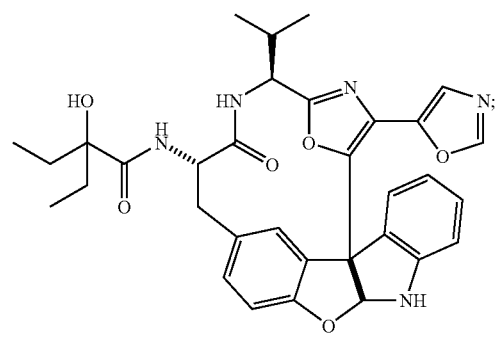
126
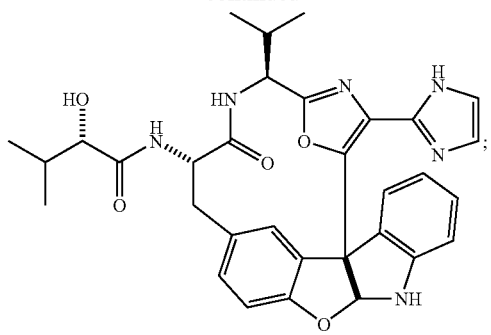
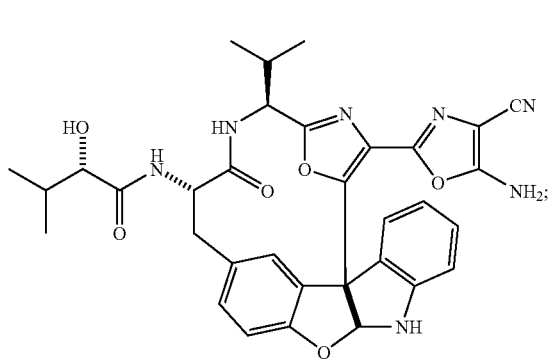
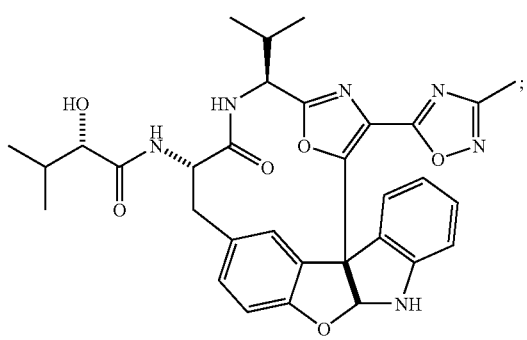
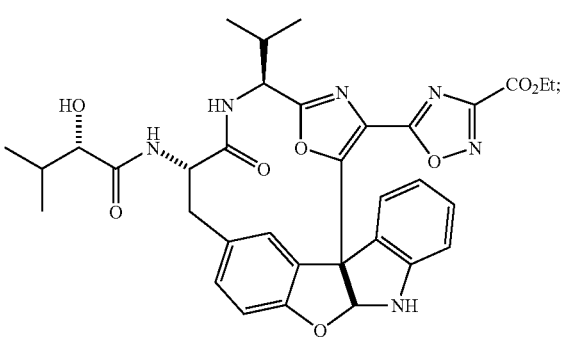
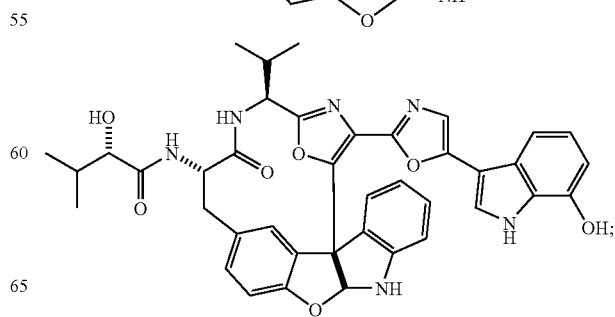

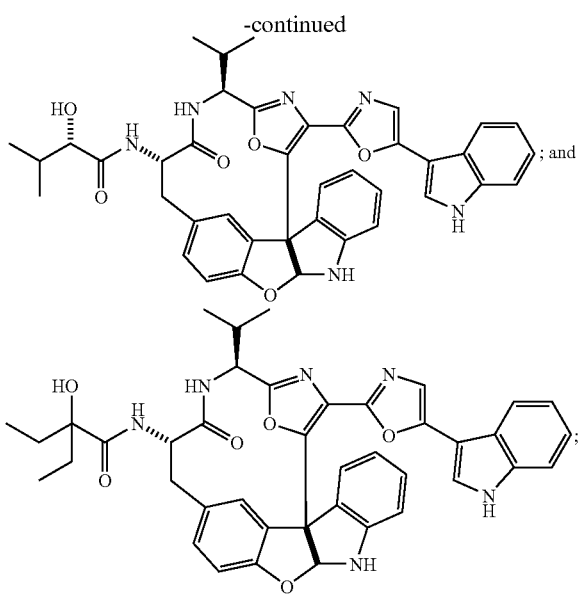

or a pharmaceutically acceptable salt thereof.

13. The compound of claim 1, wherein $R^7$ is an optionally substituted oxazole ring.

14. The compound of claim 2, wherein $R^7$ is an optionally substituted oxazole ring.

15. The compound of claim 4, wherein $R^7$ is an optionally substituted oxazole ring.

16. The compound of claim 1 wherein:

R1 is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C7-C14 arylalkyl, C6-C14 heteroarylalkyl, each of which may be optionally substituted;

$R^4$ is H or C1-C4 alkyl;

$R^5$ is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; and $R^6$ is H.

17. The compound of claim 1 wherein:

$R^1$ is an optionally substituted C1-C4 alkyl;

$R^2$ is H, or methyl;

$R^4$ is H;

$R^5$ is —C(=O)$R^3$ where $R^3$ is C1-C8 alkyl, C2-C10 alkenyl, C3-C8 cycloalkyl, C4-C9 cycloalkylalkyl, or C7-C14 arylalkyl, each of which may be optionally substituted; and $R^6$ is H.

18. The compound of claim 1 wherein:

$R^1$ is isopropyl;

$R^2$ is H;

$R^4$ is H;

$R^5$ is —C(=O)$R^3$ where $R^3$ is a C1-C8 straight chain, branched, or cycloalkyl group, each of which is substituted on the carbon atom adjacent to the carbonyl group that is part of $R^5$ with OH, OMe, OAc, NH$_2$, NHMe, CH$_2$OH or NHAc; and $R^6$ is H.

* * * * *